United States Patent
Kluge et al.

(10) Patent No.: US 10,968,172 B2
(45) Date of Patent: Apr. 6, 2021

(54) USP30 INHIBITORS

(71) Applicant: Mitobridge, Inc., Cambridge, MA (US)

(72) Inventors: Arthur Kluge, Lincoln, MA (US); Bharat Lagu, Acton, MA (US); Pranab Maiti, Bangalore (IN); Sunil Kumar Panigrahi, Hyderabad (IN)

(73) Assignee: Mitobridge, Inc., Cambridge, MA (US)

( * ) Notice: Subject to any disclaimer, the term of this patent is extended or adjusted under 35 U.S.C. 154(b) by 0 days.

(21) Appl. No.: 16/606,817

(22) PCT Filed: May 14, 2018

(86) PCT No.: PCT/US2018/032486
§ 371 (c)(1),
(2) Date: Oct. 21, 2019

(87) PCT Pub. No.: WO2018/213150
PCT Pub. Date: Nov. 22, 2018

(65) Prior Publication Data
US 2020/0131121 A1    Apr. 30, 2020

Related U.S. Application Data

(60) Provisional application No. 62/506,216, filed on May 15, 2017.

(51) Int. Cl.
| | |
|---|---|
| *C07C 311/16* | (2006.01) |
| *C07D 333/38* | (2006.01) |
| *C07D 309/08* | (2006.01) |
| *C07D 213/81* | (2006.01) |
| *C07D 233/96* | (2006.01) |
| *C07D 277/56* | (2006.01) |
| *C07D 307/24* | (2006.01) |
| *C07D 333/24* | (2006.01) |
| *C07D 237/24* | (2006.01) |
| *C07D 213/56* | (2006.01) |
| *C07D 263/34* | (2006.01) |
| *C07D 309/06* | (2006.01) |
| *C07D 233/64* | (2006.01) |

(52) U.S. Cl.
CPC .......... *C07C 311/16* (2013.01); *C07D 213/56* (2013.01); *C07D 213/81* (2013.01); *C07D 233/64* (2013.01); *C07D 233/96* (2013.01); *C07D 237/24* (2013.01); *C07D 263/34* (2013.01); *C07D 277/56* (2013.01); *C07D 307/24* (2013.01); *C07D 309/06* (2013.01); *C07D 309/08* (2013.01); *C07D 333/24* (2013.01); *C07D 333/38* (2013.01)

(58) Field of Classification Search
CPC ... C07C 311/16; C07D 213/56; C07D 213/81; C07D 233/64; C07D 233/96; C07D 237/24; C07D 263/34; C07D 277/56; C07D 307/24; C07D 309/06; C07D 309/08; C07D 333/24; C07D 333/38
USPC ........................................ 514/256
See application file for complete search history.

(56) References Cited

FOREIGN PATENT DOCUMENTS

| WO | 2016/156816 A1 | 10/2016 |
| WO | 2017/009650 A1 | 1/2017 |

OTHER PUBLICATIONS

Kluge et al., Novel highly selective inhibitors of ubiquitin specific protease 30 (USP30) accelerate mitophagy. Bioorg Med Chem Lett. Aug. 15, 2018;28(15):2655-2659. Pre-publication edition.
International Search Report and Written Opinion for Application No. PCT/US2018/032486, dated Aug. 29, 2018, 15 pages.

*Primary Examiner* — Kristin A Vajda
(74) *Attorney, Agent, or Firm* — McCarter & English, LLP; Steven G. Davis; Wei Song

(57) ABSTRACT

The application relates to phenyl- or naphthylsulfonamide derivatives of the structural formula (I). The compounds are described as inhibitors of USP30 (ubiquitin specific peptidase 30) useful for the treatment of conditions involving mitochondrial defects including neurodegenerative diseases such as Alzheimer's and Parkinson's or a neoplastic disease such as leukemia.

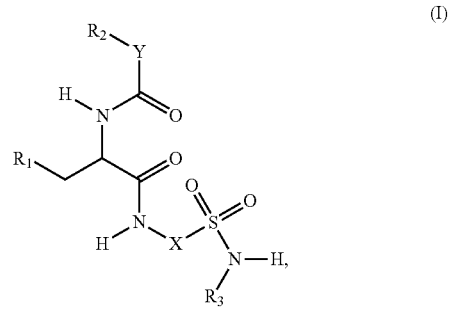

20 Claims, No Drawings

USP30 INHIBITORS

CROSS-REFERENCES TO RELATED APPLICATIONS

This application is a U.S. national stage filing, under 35 U.S.C. § 371(c), of International Application No. PCT/US2018/032,486, filed on May 14, 2018, which claims the benefit of U.S. Provisional Application No. 62/506,216, filed on May 15, 2017. The entire teachings of the aforementioned applications are incorporated herein by reference.

FIELD OF THE INVENTION

This application is directed to inhibitors of USP30, and methods for their use, such as to treat or prevent conditions involving mitochondrial defects.

BACKGROUND OF THE INVENTION

The smooth functioning of mitochondria in cells is controlled by the coordination of the four processes of biogenesis, fission, fusion and autophagy. Autophagy (mitophagy) is upregulated when mitochondria are damaged, as for example by the action of reactive oxygen species, hypoxia or nutrient deprivation. In such cases, cells attempt to repair damage by targeting the damaged mitochondria for lysosomal degradation through labeling mitochondrial proteins with ubiquitin. This process is initiated by the localization of protein kinase PINK2 and the E3 ubiquitin ligase Parkin on damaged mitochondria, and leads to the ubiquitination of over forty mitochondrial proteins.

USP30, a mitochondria-localized deubiquitinase (DUB) is an antagonist of Parkin-meditated mitophagy. USP30, through its deubiquitinase activity, counteracts ubiquitination and degradation of damaged mitochondria, and inhibition of USP30 rescues mitophagy defects caused by mutant Parkin. Further, inhibition of USP30 decreases oxidative stress and provides protection against the mitochondrial toxin, rotenone. Since damaged mitochondria are more likely to accumulate Parkin, USP30 inhibition should preferentially clear unhealthy mitochondria. In addition to neurons (such as substantia nigra neurons, which are especially vulnerable to mitochondria dysfunction in Parkinson's disease), long-lived metabolically active cells such as cardiomyocytes also rely on an efficient mitochondria quality control system. In this context, Parkin has been shown to protect cardiomyocytes against ischemia/reperfusion injury through activating mitophagy and clearing damaged mitochondria in response to ischemic stress. Thus, inhibitors of USP30 are provided for use in treating a conditions involving mitochondrial defects, including neurological conditions, cardiac conditions, and systemic conditions.

Deubiquinating enzymes function to oppose the action of the ubiquitinating enzymes in post-translational modification of cellular proteins. USP30 is a deubiquitinase that is localized to mitochondria and has been shown in expression studies to oppose the action of Parkin-mediated ubiquination and clearance of damaged mitochondria. Accordingly, there remains a need in the art for novel compounds capable of effectively and reliably inhibiting USP30 in vitro and in vivo. The present invention addresses these and other such needs.

SUMMARY OF THE INVENTION

Provided herein, inter alia, are compounds and compositions comprising such compounds that are useful for inhibiting USP30 activity (see, e.g., Example 1). In particular, disclosed herein are methods for modulating the activity of USP30 for the treatment of diseases, developmental delays, and symptoms related to mitochondrial dysfunction. For example, the disclosed compounds and compositions are useful in the treatment of mitochondrial diseases, such as Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, retinitis pigmentosa, and Pearson Syndrome. Alternatively, the disclosed compounds and compositions are useful in the treatment of other USP30-related diseases, such as cardiovascular disease, kidney disease, ophthalmic conditions, cancer, cognitive disease, and other related conditions.

In one embodiment, provided herein is a compound represented by the following structural Formula (I):

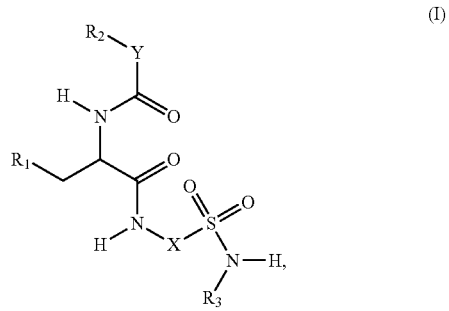

or a pharmaceutically acceptable salt thereof, wherein:

X is phenyl or naphthyl;

Y is absent, a methylene group, an ethylene group, or an ethenylene group;

$R_1$ is ($C_1$-$C_4$)alkyl, 3-7 membered cycloalkyl, 5-6 membered heterocyclyl, 6-10 membered aryl, or 5-6 membered heteroaryl, each of which is independently optionally substituted with one or more substituents selected from the group consisting of halogen, —CN, —$CO_2$H, hydroxyl, ($C_1$-$C_4$)alkyl, halo($C_1$-$C_4$)alkyl, ($C_1$-$C_4$)alkoxy, halo($C_1$-$C_4$)alkoxy, methylenedioxy, phenyl, —$NO_2$, —$OR^c$, —$NR^aR^b$, —S(O)$_i$$R^a$, —$NR^a$S(O)$_i$$R^b$, —S(O)$_i$$NR^aR^b$, —C(=O)$OR^a$, —OC(=O)$OR^a$, —C(=S)$OR^a$, —O(C=S)$R^a$, —C(=O)$NR^aR^b$, —$NR^a$C(=O)$R^b$, —C(=S)$NR^aR^b$, —$NR^a$C(=S)$R^b$, —$NR^a$(C=O)$OR^b$, —O(C=O)$NR^aR^b$, —$NR^a$(C=S)$OR^b$, —O(C=S)$NR^aR^b$, —$NR^a$(C=O)$NR^aR^b$, —$NR^a$(C=S)$NR^aR^b$, —C(=S)$R^a$, and —C(=O)$R^a$;

$R_2$ is 3-7 membered cycloalkyl, 5-6 membered heterocyclyl, 6-10 membered aryl, 5-6 membered heteroaryl, or bridged 5-10 membered cycloalkyl; each of which is independently optionally substituted with one or more substituents selected from the group consisting of halogen, CN, —$CO_2$H, hydroxyl, ($C_1$-$C_4$)alkyl, halo($C_1$-$C_4$)alkyl, ($C_1$-$C_4$)alkoxy, halo($C_1$-$C_4$)alkoxy, ($C_1$-$C_4$)alkylthio, —$NO_2$, —$OR^c$, —$NR^aR^b$, —S(O)$_i$$R^a$, —$NR^a$S(O)$_i$$R^b$, —S(O)$_i$$NR^aR^b$, —C(=O)$OR^a$, —OC(=O)$OR^a$, —C(=S)$OR^a$, —O(C=S)$R^a$, —C(=O)$NR^aR^b$, —$NR^a$C(=O)$R^b$, —C(=S)$NR^aR^b$, —$NR^a$C(=S)$R^b$, —$NR^a$(C=O)$OR^b$, —O(C=O)$NR^aR^b$, —$NR^a$(C=S)$OR^b$, —O(C=S)$NR^aR^b$, —$NR^a$(C=O)$NR^aR^b$, —$NR^a$(C=S)$NR^aR^b$, —C(=S)$R^a$, and —C(=S)$R^a$;

R$_3$ is isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl;

each R$^a$ and each R$^b$ are independently selected from —H and (C$_1$-C$_5$)alkyl, optionally substituted with hydroxyl or (C$_1$-C$_3$)alkoxy;

R$^c$ is —H, (C$_1$-C$_5$)haloalkyl or (C$_1$-C$_5$)alkyl, wherein the (C$_1$-C$_5$)alkyl is optionally substituted with hydroxyl or (C$_1$-C$_3$)alkoxy; and i is 0,1 or 2.

Pharmaceutical compositions of compounds of the invention also are disclosed herein. Particular embodiments comprise a pharmaceutically acceptable carrier or excipient and one or more of the disclosed compounds, or a pharmaceutically acceptable salt thereof. The pharmaceutical compositions of the invention can be used in therapy, e.g., for treating a USP30-related disease or condition in a subject.

Another embodiment comprises treating a USP30-related disease or condition in a subject by administering to the subject an effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, for the preparation of a medicament for the treatment of a USP30-related disease or condition.

In another embodiment, provided herein the disclosed compounds, or a pharmaceutically acceptable salt thereof, or a pharmaceutical composition comprising one or more of the disclosed compounds are for use in treating a USP30-related disease or condition.

DETAILED DESCRIPTION

The invention is directed to USP30 inhibitors represented by Formula (I). USP30 inhibitor refers to any chemical entity that blocks the activity of USP30. Substances can be tested for activity against USP30 by exposing USP30 cell free preparations or cells expressing USP30 to the compounds and detecting the USP30 activity by biochemical, biophysical, functional, imaging, or other indicators of USP30 activity (see, e.g., Example 4).

USP30 sequences (OMIM 612492) are publically available, for example, from GenBank® sequence database (e.g., NP_001288104 (human, protein, partial) and NM_001301175 (human, nucleic acid)).

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. (C$_1$-C$_5$)alkyl. As used herein, a "(C$_1$-C$_5$)alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "(C$_1$-C$_4$)alkoxy" includes methoxy, ethoxy, propoxy, and butoxy.

The terms "haloalkyl" and "haloalkoxy" means alkyl or alkoxy, as the case may be, substituted with one or more halogen atoms.

"Alkylene" refers to a bivalent straight-chained saturated hydrocarbon, such as methylene —(CH$_2$)— or ethylene —(CH$_2$CH$_2$)—. "Alkenylene" refers to a bivalent straight-chained hydrocarbon with at least one double bond, such as ethenylene —(CH═CH)—.

The term "cycloalkyl" refers to a monocyclic saturated hydrocarbon ring system. For example, a C$_{3-7}$ cycloalkyl includes cyclopropyl, cyclobutyl, cyclopentyl, cyclohexyl and cycloheptyl. Unless otherwise described, a "cycloalkyl" has from three to six carbon atoms.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to monocyclic aromatic ring groups having five or six ring atoms (i.e., "5-6 membered") selected from carbon and at least one (typically to 4, more typically 1 or 2) heteroatoms (e.g., oxygen, nitrogen or sulfur).

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl.

The term "heterocyclyl" refers to a monocyclic non-aromatic ring radical containing from 5-6 ring atoms (i.e., "5-6 membered") selected from carbon and 1 or 2 heteroatoms. Each heteroatom is independently selected from nitrogen, quaternary nitrogen, oxidized nitrogen (e.g., NO); oxygen; and sulfur, including sulfoxide and sulfone. Representative heterocyclyl groups include morpholinyl, thiomorpholinyl, pyrrolidinonyl, pyrrolidinyl, piperidinyl, piperazinyl, tetrahydrofuranyl, tetrahydropyranyl, tetrahydropyridyl, tetrahydropyrimidinyl, tetrahydrothiophenyl, tetrahydrothiopyranyl, and the like. A "substituted heterocylyl group" is substituted at any one or more substitutable ring atom, which is a ring carbon or ring nitrogen atom bonded to a hydrogen.

As used herein, many moieties (e.g., alkyl, alkylene, cycloalkyl, aryl, heteroaryl, or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Suitable substituents are those which do not have a significant adverse effect on the ability of the compound to inhibit USP30. Where suitable substituents are not specifically enumerated, exemplary substituents include, but are not limited to: (C$_1$-C$_5$)alkyl, (C$_1$-C$_5$)hydroxyalkyl, (C$_1$-C$_5$) haloalkyl, (C$_1$-C$_5$) alkoxy, (C$_1$-C$_5$) haloalkoxy, halogen, hydroxyl, cyano, amino, —CN, —NO$_2$, —NR$^a$R$^b$, —S(O)$_i$R$^a$, —NR$^a$S(O)$_i$R$^b$, —S(O)$_i$NR$^a$R$^b$, —C(═O)OR$^a$, —OC(═O)OR$^a$, —C(═S)OR$^a$, —O(C═S)R$^a$, —C(═O)

$NR^aR^b$, $-NR^aC(=O)R^b$, $-C(=S)NR^aR^b$, $-NR^aC(=S)R^b$, $-NR^a(C=O)OR^b$, $-O(C=)NR^aR^b$, $-NR^a(C=S)OR^b$, $-O(C=S)NR^aR^b$, $-NR^a(C=O)$ $NR^aR^b$, $-NR^a(C=S)NR^aR^b$, $-C(=S)R^a$, $-C(=O)R^a$, phenyl, or 5-6 membered heteroaryl. Each $R^a$ and each $R^b$ are independently selected from —H and ($C_1$-$C_5$)alkyl, optionally substituted with hydroxyl or ($C_1$-$C_3$)alkoxy; $R^c$ is —H, ($C_1$-$C_5$) haloalkyl or ($C_1$-$C_5$)alkyl, wherein the ($C_1$-$C_5$) alkyl is optionally substituted with hydroxyl or ($C_1$-$C_3$)alkoxy.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers, including essentially pure stereo or geometric isomers, as well as combination thereof.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "Geometric isomers" are stereoisomers that differ in the orientation of substituent atoms in relationship to a carbon-carbon double bond, to a carbocyclyl ring, or to a bridged bicyclic system.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure (also referred to as "enantiomerically pure"). Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and, e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds having basic amine groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S.

M. Berge, et al. describes pharmacologically acceptable salts in *J. Pharm. Sci.*, 1977, 66:1-19.

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

For example, disclosed compounds can be administered alone or in combination with one or more other mitodondrial-modulating compounds, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (−)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments;

anti-obesity agents; anti-inflammatory active ingredients; active ingredients for treating malignant tumors; anti-thrombotic active ingredients; active ingredients for treating high blood pressure; active ingredients for treating heart failure, and combinations thereof.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "an effective amount" means an amount when administered to the subject which results in beneficial or desired results, including clinical results, e.g., inhibits, suppresses or reduces the symptoms of the condition being treated in the subject as compared to a control. For example, an effective amount can be given in unit dosage form (e.g., from 1 mg to about 50 g per day, e.g., from 1 mg to about 5 grams per day).

The particular mode of administration and the dosage regimen will be selected by the attending clinician, taking into account the particulars of the case (e.g., the subject, the disease, the disease state involved and the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a USP30-related disease using the disclosed USP30 inhibitors for guidance.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

Compounds of the Invention

Disclosed herein are embodiments of a compound having the general structure of Formula (I).

In a 1$^{st}$ embodiment, the compound of Formula (I) is represented by structural formula (Ia):

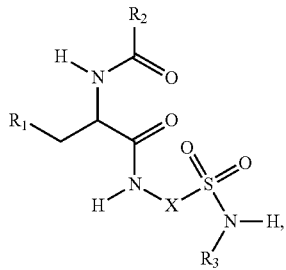

(Ia)

or a pharmaceutically acceptable salt thereof, and the remaining variables are the same as defined for Formula (I). $R^{a-c}$ are preferably independently H or methyl.

In a 2$^{nd}$ embodiment, the compound of Formula (I) is represented by structural formula (Ib):

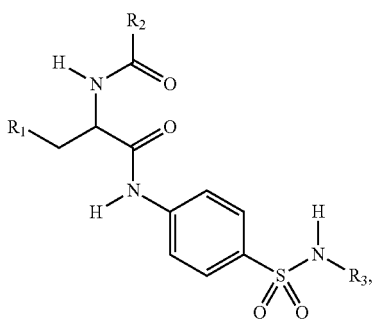

(Ib)

or a pharmaceutically acceptable salt thereof, and the remaining variables are as defined for Formula (I) or in the 1$^{st}$ embodiment.

In a 3$^{rd}$ embodiment, the compound of Formula (I) is represented by structural formula (Ic):

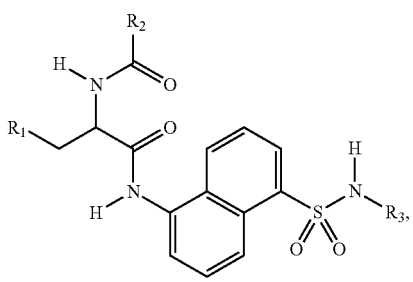

(Ic)

or a pharmaceutically acceptable salt thereof, and the remaining variables are as defined for Formula (I) or in the 1$^{st}$ embodiment.

In a 4$^{th}$ embodiment, the compound has the structure of Formula (I), (Ia), (Ib) or (Ic), wherein $R_2$ is 3-7 membered cycloalkyl optionally substituted with one or more substituents selected from the group consisting of $(C_1-C_4)$alkyl, $(C_1-C_4)$alkoxy, $(C_1-C_4)$alkylthio, hydroxyl, halogen, and halo$(C_1-C_4)$alkyl; phenyl optionally substituted with one or more substituents selected from the group consisting of halogen, CN, —CO$_2$H, —CO$_2$Me, $(C_1-C_4)$alkyl, halo$(C_1$-$C_4)$alkyl, $(C_1-C_4)$alkoxy, and hydroxyl; 5-6 membered heterocyclyl optionally substituted with one or more substituents selected from the group consisting of $(C_1-C_4)$alkyl, halo$(C_1-C_4)$alkyl, and $(C_1-C_4)$alkoxy; 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy; or adamantyl; and the remaining variables are as defined for Formula (I) and in the 1$^{st}$, 2$^{nd}$, and/or 3$^{rd}$ embodiment(s).

In a 5$^{th}$ embodiment, the compound has the structure of Formula (I), (Ia), (Ib) or (Ic), or a pharmaceutically acceptable salt thereof, wherein $R_1$ is $(C_1-C_4)$alkyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 3-7 membered cycloalkyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 5-6 membered heterocyclyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; phenyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, methylenedioxy, and phenyl; or 5-6 membered heteroaryl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; and the remaining variables are as defined for Formula (I) and in the 1$^{st}$, 2$^{nd}$, 3$^{rd}$, and/or 4$^{th}$ embodiment(s).

In a 6$^{th}$ embodiment, the compound has the structure of Formula (I), (Ia), (Ib) or (Ic), wherein $R_2$ is 3-7 membered cycloalkyl optionally substituted with one or more substituents selected from the group consisting of halogen and $(C_1-C_4)$alkyl; phenyl optionally substituted with one or more substituents selected from the group consisting of halogen, CN, —CO$_2$H, —CO$_2$Me, $(C_1-C_4)$alkyl, halo$(C_1$-$C_4)$alkyl, $(C_1-C_4)$alkoxy, and hydroxyl; 5-6 membered heterocyclyl selected from tetrahydrofuranyl or tetrahydro-2H-pyranyl; 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy, wherein the heteroaryl is pyridyl, pyridazinyl, pyrimidinyl, thiazolyl, oxazolyl, furanyl, pyrrolyl, or thiophenyl; and the remaining variables are as defined for Formula (I) and in the 1$^{st}$, 2$^{nd}$, 3$^{rd}$, 4$^{th}$, and/or 5$^{th}$ embodiment(s).

In a 7$^{th}$ embodiment, the compound has the structure of Formula (I), (Ia), (Ib) or (Ic), or a pharmaceutically acceptable salt thereof, wherein $R_1$ is $(C_1-C_4)$alkyl; 3-7 membered cycloalkyl; tetrahydro-2H-pyranyl; phenyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and phenyl; 5-6 membered heteroaryl selected from pyridyl, imidazolyl, and thiophenyl; and the remaining variables are as defined for Formula (I) and in the 1$^{st}$, 2$^{nd}$, 3$^{rd}$, 4$^{th}$, 5$^{th}$, and/or 6$^{th}$ embodiment(s).

In an 8th embodiment, the compound has the structure of Formula (I), (Ia), (Ib) or (Ic), or a pharmaceutically acceptable salt thereof, wherein $R_3$ is t-butyl; and the remaining variables are as defined for Formula (I) and in the 1st, 2nd, 3rd, 4th, 5th, 6th, and/or 7th embodiment(s).

In a 9th embodiment, the compound has the structure of Formula (I), (Ia), (Ib) or (Ic), or a pharmaceutically acceptable salt thereof, wherein $R_1$ is $(C_1-C_4)$alkyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; a 3-7 membered cycloalkyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 5-6 membered heterocyclyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 6-10 membered aryl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, methylenedioxy, and phenyl; 5-6 membered heteroaryl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; or a 5-10 membered bicycloalkyl selected from the group consisting of bicyclo[2.2.2]oct-1-yl, bicyclo[2.2.2]oct-2-yl, bicyclo[2.2.1]hept-1-yl, bicyclo[2.2.1]hept-2-yl; bicyclo[1.1.1]pentan-1-yl;

$R_2$ is a 3-7 membered cycloalkyl optionally substituted with one or more substituents selected from the group consisting of $(C_1-C_4)$alkyl, $(C_1-C_4)$alkoxy, $(C_1-C_4)$alkylthio, hydroxyl, halogen, and halo$(C_1-C_4)$alkyl; a 6-10 membered aryl optionally substituted with one or more substituents selected from the group consisting of halogen, CN, —$CO_2H$, —$CO_2Me$, $(C_1-C_4)$alkyl, halo$(C_1-C_4)$alkyl, $(C_1-C_4)$alkoxy, and hydroxyl; a 5-6 membered heterocyclyl optionally substituted with one or more substituents selected from the group consisting of $(C_1-C_4)$alkyl, halo$(C_1-C_4)$alkyl, $(C_1-C_4)$alkoxy; or a 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy;

and the remaining variables are as defined for Formula (I) and in the 1st and/or 2nd embodiment(s).

Methods of Treatment

Methods of treating a USP30-related disease or condition in a subject are disclosed. The methods can include administering to the subject an effective amount of one or more compounds or compositions provided herein.

In one embodiment, the USP30-related disease is a mitochondrial disease. Examples of mitochondrial diseases include, but are not limited to, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the USP30-related disease is a vascular disease (such as a cardiovascular disease or any disease that would benefit from increasing vascularization in tissues exhibiting impaired or inadequate blood flow). In other embodiments, the USP30-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the USP30-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the USP30-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the USP30-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the USP30-related disease is a neuronal activation disorder, Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the USP30-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the USP30-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the USP30-related disease is a beta oxidation disease. Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of (β-oxidation (RR-MADD).

In some embodiments, the USP30-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the USP30-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the USP30-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the USP30-related disease is a metabolic disease. Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer's disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the USP30-related disease is cancer. Examples of cancer include, but are not limited to, cancers of the colon, large intestine, skin, breast, prostate, ovary, and/or lung.

In other embodiments, the USP30-related disease is an ischemic injury. Examples of ischemic injuries include, but are not limited to, cardiac ischemia, such as myocardial infarction; brain ischemia (e.g., acute ischemic stroke; chronic ischemic of the brain, such as vascular dementia; and transient ischemic attack (TIA); bowel ischemia, such as ischemic colitis; limb ischemia, such as acute arm or leg ischemia; subcutaneous ischemia, such as cyanosis or gangrene; and ischemic organ injury, such as ischemic renal injury (IRI).

In still other embodiments, the USP30-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury (also known as acute renal failure), chronic renal failure, diabetic nephropathy, or Bartter's syndrome.

EXEMPLIFICATION

Abbreviations
Ac acetyl
DAST diethylaminosulfur trifluoride
DCM dichloromethane
DIPEA Diisopropylethylamine
DMF N,N-dimethylformamide
DMSO dimethylsulfoxide
EDC 1-ethyl-3-(3-dimethylaminopropyl)carbodiimide
Et ethyl
HOBt N-hydroxybenzotriazole
Me methyl
rt room temperature
TBAB tetrabutylammonium bromide
THF tetrahydrofuran General Scheme-1: Synthesis of compounds 4a-z.

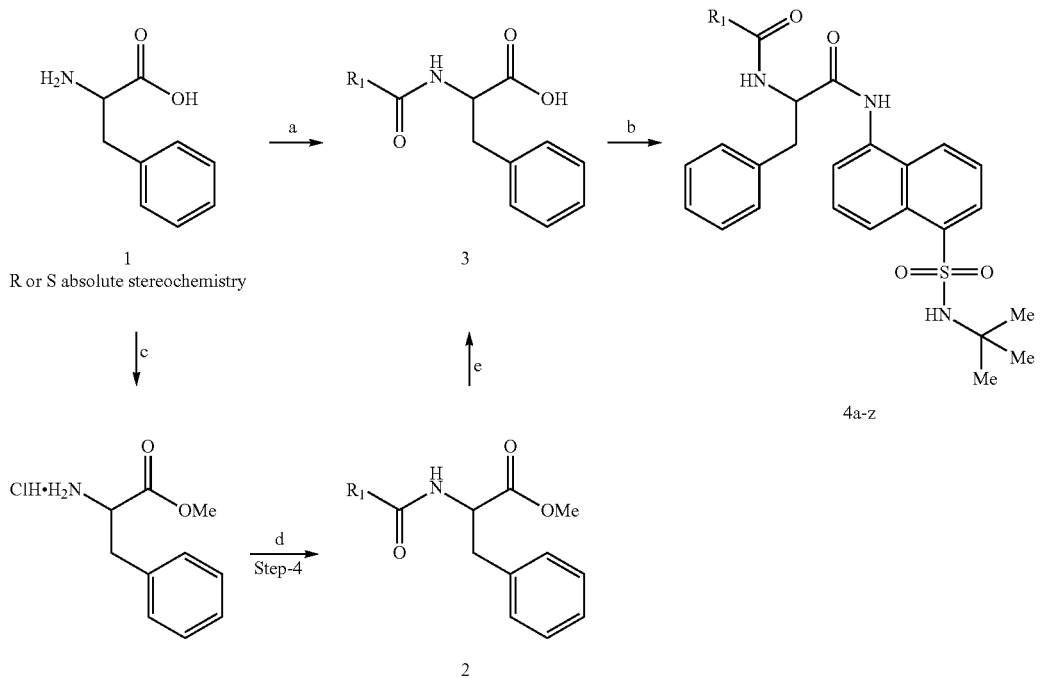

Reagents and conditions: a) Acid chloride, aq. NaOH (2 N), 0-5° C., 2 h; b) 5-amino-N-(tert-butyl)naphthalene-1-sulfonamide (3aa), EDC•HCl, HOBt, DMF, 0° C. - rt, 16 h. c) SOCl$_2$ MeOH, reflux, 16 h; d) corresponding acid, EDC•HCl, HOBt, DIPEA, dry DMF, rt, 16 h; e) LiOH•H$_2$O, THF, MOH, H$_2$O, rt, 6 h;

Scheme-1a: Synthesis of 5-amino-N-(tert-butyl)naphthalene-1-sulfonamide (3aa)
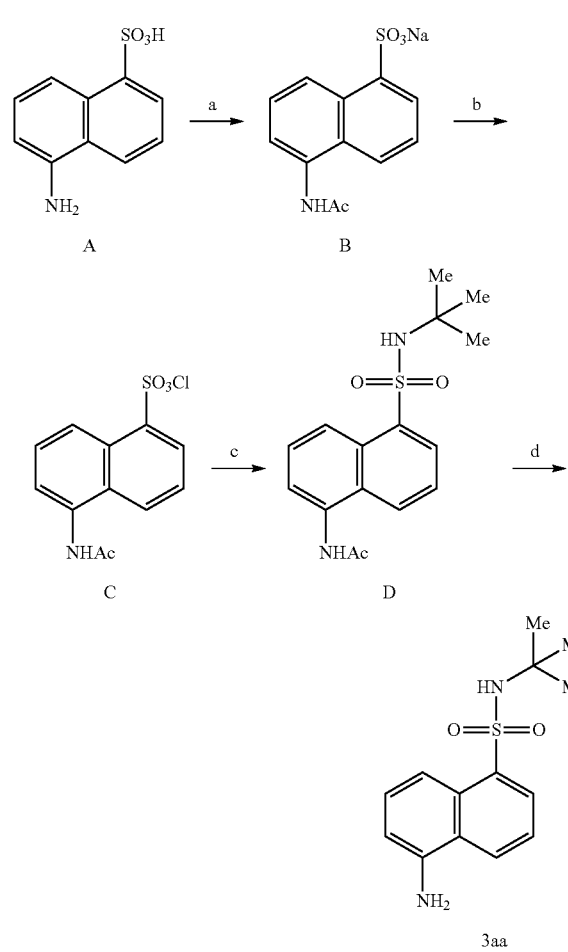
Reagents and conditions: a) aq. NaOH (2 N); Ac₂O, 100° C., 2 h; b) Chlorosulfuric acid, rt, 2.5 h; c) 2-methylpropan-2-amine, Et₃N, dry THF, rt, 16 h; d) aq. NaOH (5 N), MeOH, 80° C., 16 h.
Scheme-1b: Synthesis of 4b
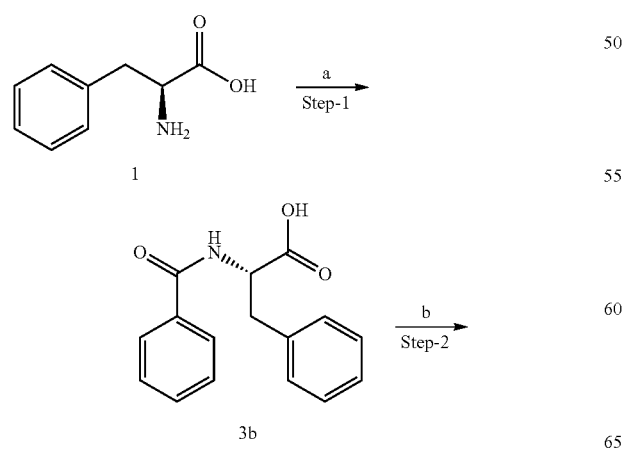
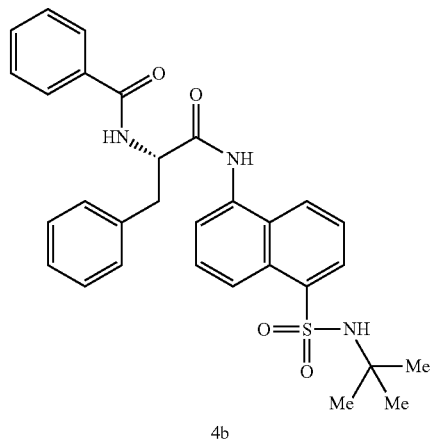
Reagents and conditions: a) Benzoyl chloride, aq. NaOH (2 N), 0-5° C., 2h; b) 5-amino-N-(tert-butyl)naphthalene-1-sulfonamide (3aa), EDC·HCl, HOBt, DMF, 0° C. - rt, 16 h.
Scheme-1c
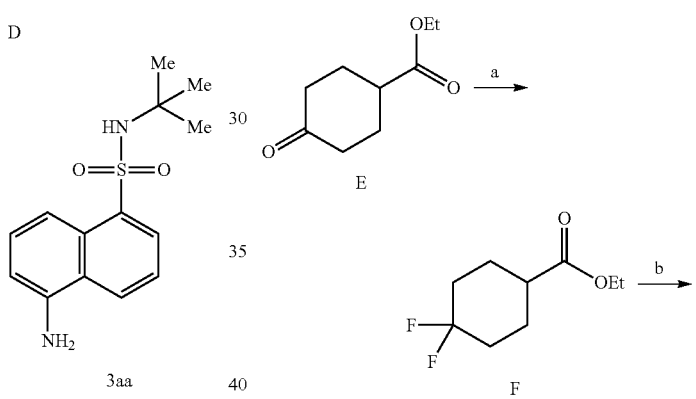
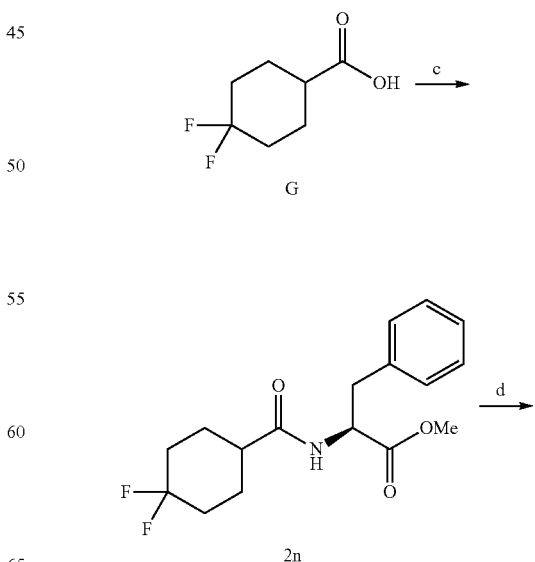

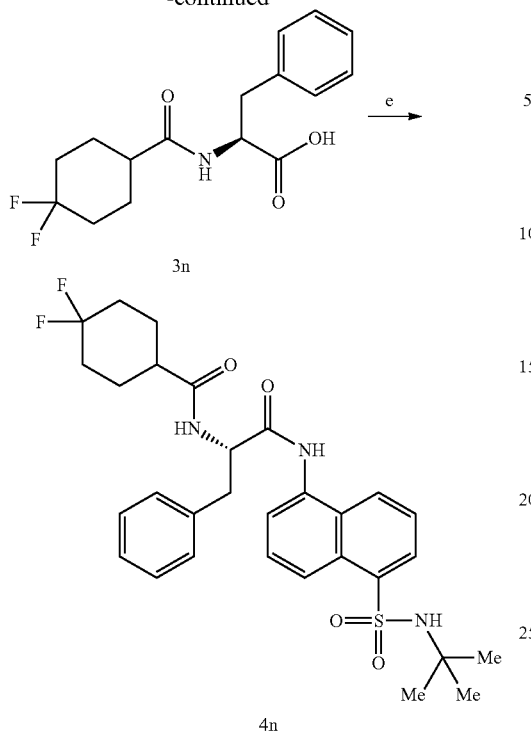

3n

4n

Reagents and conditions: a) DAST, carbon tetrachloride, rt, 16 h; b) aq. NaOH (2N), EtOH, rt, 2 h; c) Methyl-L-phenylalaninate hydrochloride, EDC•HCl, HOBt, DIPEA, dry DMF, rt, 16 h; d) LiOH•H$_2$O, THF, MeOH, H$_2$O, rt, 6 h; e) 5-amino-N-(tert-butyl) naphthalene-1-sulfonamide (3aa), EDC•HCl, HOBt, dry DMF, rt, 48 h.

General Scheme-2: Synthesis of compound 7a-n. (Compounds 7a and 7c-n were synthesized using (b) while compound 7b was synthesized using conditions (b) and (c)).

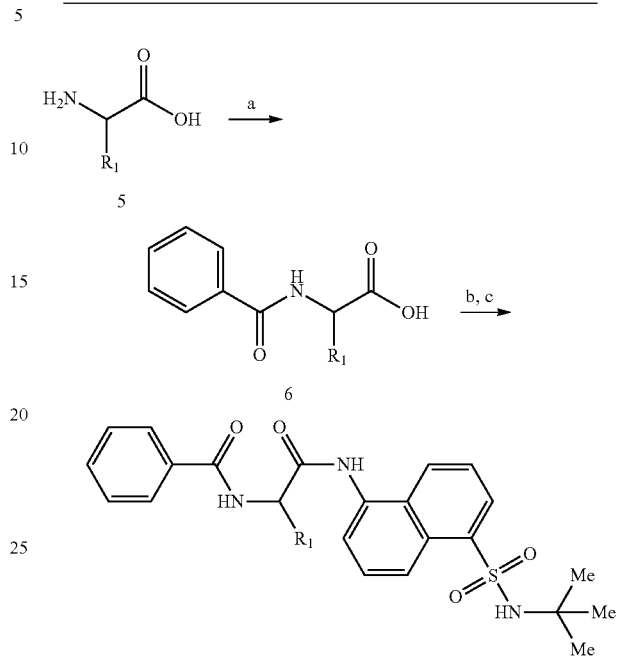

7a-n

Reagents and conditions: a) Benzoyl chloride, aq. NaOH (2 N), 0-5° C., 2 h; b) 5-amino-N-(tert-butyl)naphthalene-1-sulfonamide (3aa), EDC•HCl, HOBt, DMF, 0° C. - rt. 16 h; c). 6ba, aq. NaOH (2 N), DMF, rt, 2 h (only for compound 7b).

General Scheme-3: Synthesis of copounds 10a-j (Compounds 10a-e, 10g and 10j were synthesised using condition(b); compound 10f was synthesized from compound 10g using conditions (b) and (e); compound 10i was synthesised using conditions (b) and (c)).

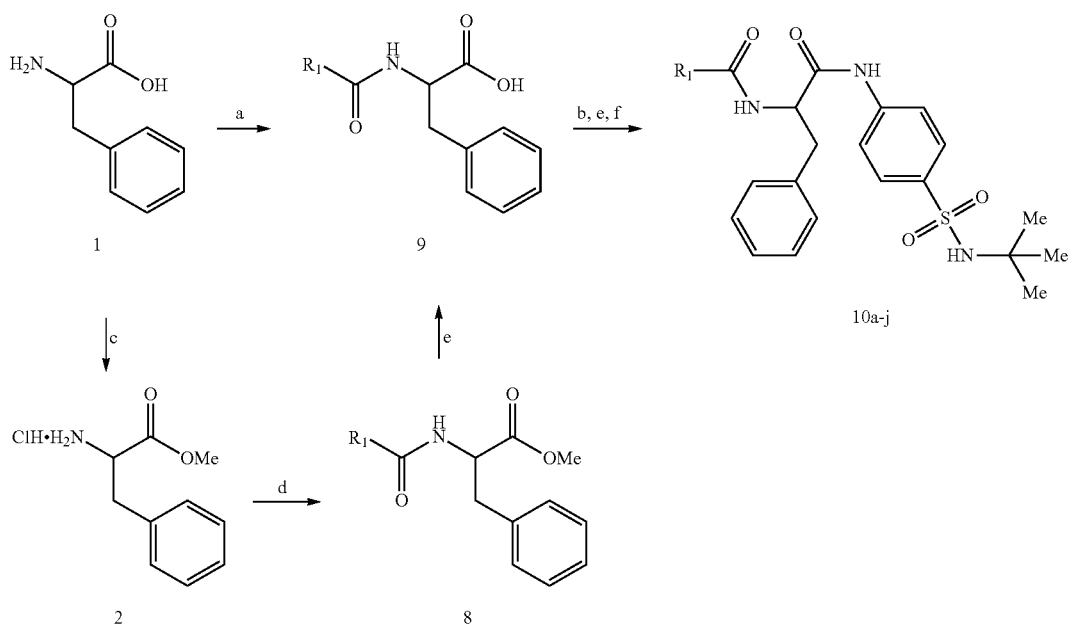

Reagents and conditions: a) Acid chloride, aq. NaOH (2 N), 0-5° C., 2 h; b) 4-amino-N-(tert-butyl)benzenesulfonamide (3ab), EDC•HCl, HOBt, DMF, 0° C. - rt, 16 h. c) SOCl$_2$, MeOH, reflux, 16 h; d) corresponding acid, EDC•HCl, HOBt, DIPEA, dry DMF, rt, 16 h; e) 10g. LiOH•H$_2$O, THF, MOH, H$_2$O, rt, 6 h (for compound 10f). f) 9ca, 10% Pd/C, H$_2$, MeOH, rt, 2 h (for compound 10i).

Scheme-3a: Synthesis of 4-amino-N-(tert-butyl)benzenesulfonamide (3ab)

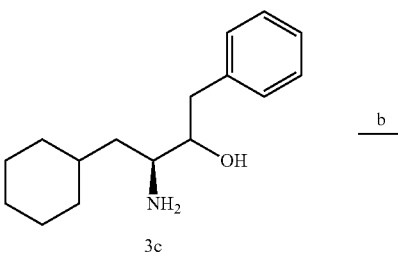

Reagents and conditions: a) Chlorosulfuric acid, 60° C., 2 h; b) 2-methylpropan-2-amine, Et₃N, dry DMF, 110° C., 16 h; c) aq. NaOH (2 N), MeOH, 100° C., 8 h.

Scheme-3b: Synthesis of (S)-N-(1-((4-(N-(tert-butyl)sulfamoyl)phenyl)amino)-1-oxo-3-phenylpropan-2-yl)cyclohexanecarboxamide (10b)

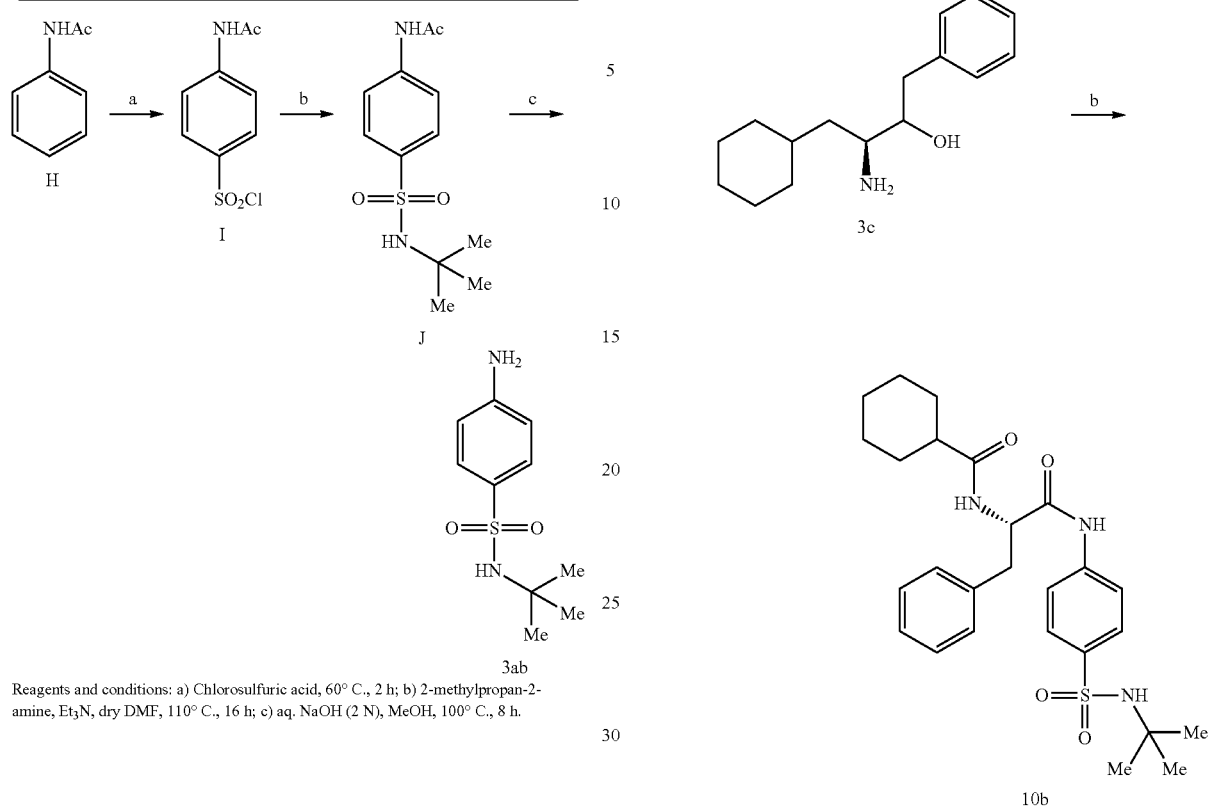

Reagents and conditions: a) Cyclohexanecarbonyl chloride, aq. NaOH (2 N), rt, 2h; b) 4-amino-N-(tert-butyl)benzenesulfonamide, EDC•HCl, HOBt, dry DMF, rt, 48 h;

General Scheme-4: Synhtesis of compounds 14a-j.

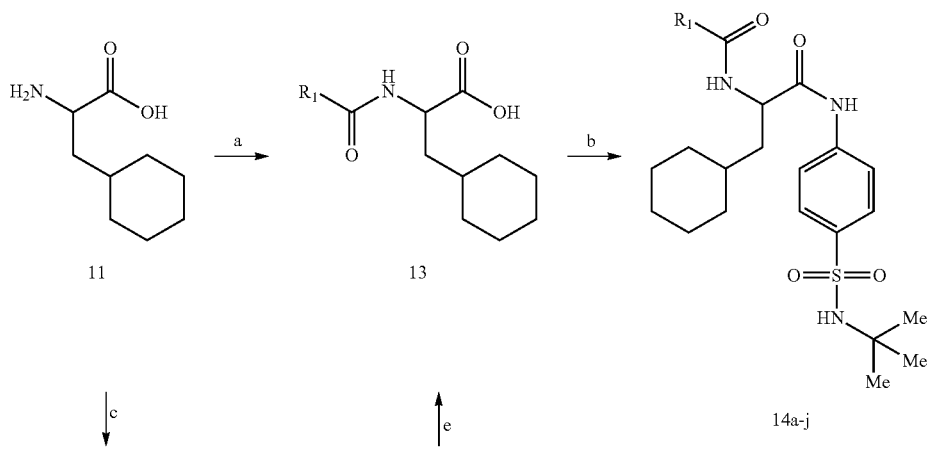

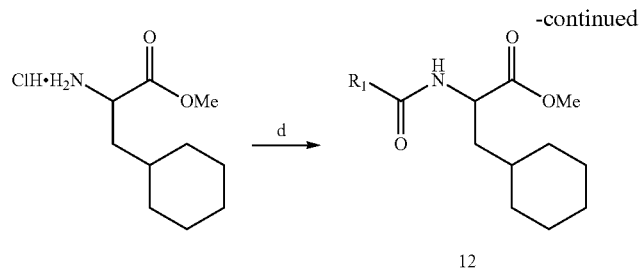

12

Reagents and conditions: a) Acid chloride, aq. NaOH (2 N), 0-5° C., 2 h; b) 4-amino-N-(tert-butyl)benzenesulfonamide (3ab), EDC•HCl, HOBt, DMF, 0° C. - rt, 16 h. c) SOCl₂, MeOH, reflux, 16h; d) corresponding acid, EDC.HCl, HOBt, DIPEA, dry DMF, rt, 16h; e) LiOH.H₂O, THF, MeOH, H₂O, rt, 6h;

General Scheme-5: Synthesis of 19a-z, 19aa-af.

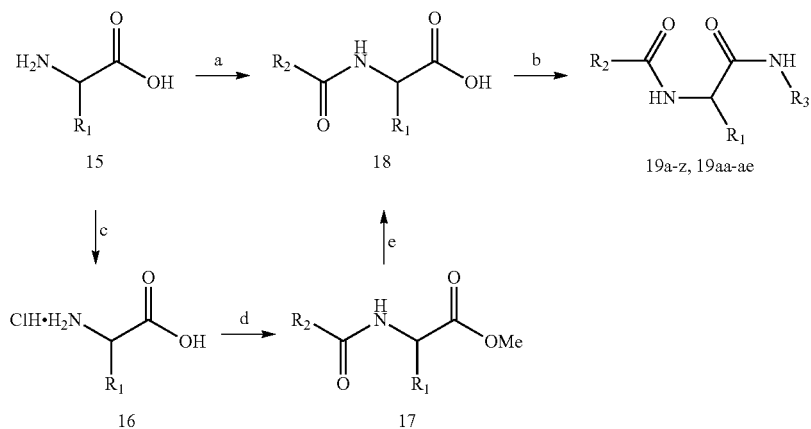

Reagents and conditions: a) Acid chlorine, aq. NaOH (2 N), 0-5° C., 2 h; b) 3aa (for compound 19p, 19q), 3ab (for compound 19a-c, 19e-g, 19i-l, 19n, 19o, 19s-z, 19aa-ae), 3ad (for compound 19d), 3ae (for compound 19m), or 3af (for compound 19h), EDC•HCl, HOBt, DMF, 0° C. - rt, 16 h. c) SOCl₂, MeOH, reflux, 16 h; d) corresponding acid, EDC•HCl, HOBt, DIPEA, dry DMF, rt, 16 h; e) LiOH•H₂O, THF, MeOH, H₂O, rt, 6 h;

Scheme 5a: Synthesis of compounds 3ad-af.

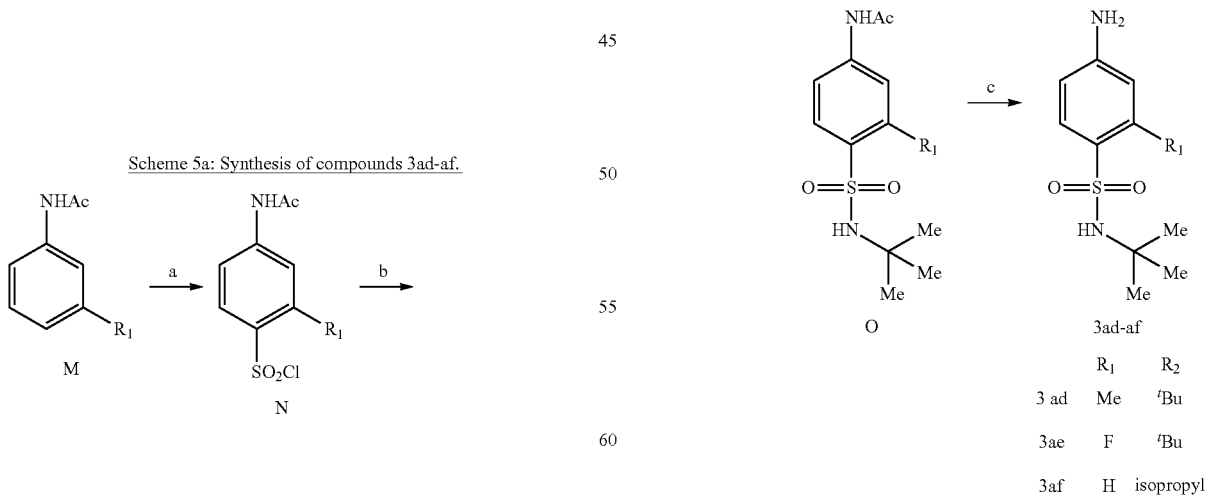

|     | R₁ | R₂        |
|-----|----|-----------|
| 3ad | Me | ᵗBu       |
| 3ae | F  | ᵗBu       |
| 3af | H  | isopropyl |

Reagents and conditions: a) Chlorosulfuric acid, 60° C., 2 h; b) 2-methylpropan-2-amine (for compound 3ad, 3ae) or propan-2-amine (for compound 3af), Et₃N, dry DMF, 110° C., 5 h; c) aq. NaOH (2 N), MeOH, 100° C., 8 h.

Synthesis of compound 3ad-3af: Compounds 3ad-af were synthesized following same method as described for compound 3ab.

Scheme 5b: Synthesis of 3-(3-cyanophenyl)-2-(cyclohexanecarboxamido)propanoic acid (18x)

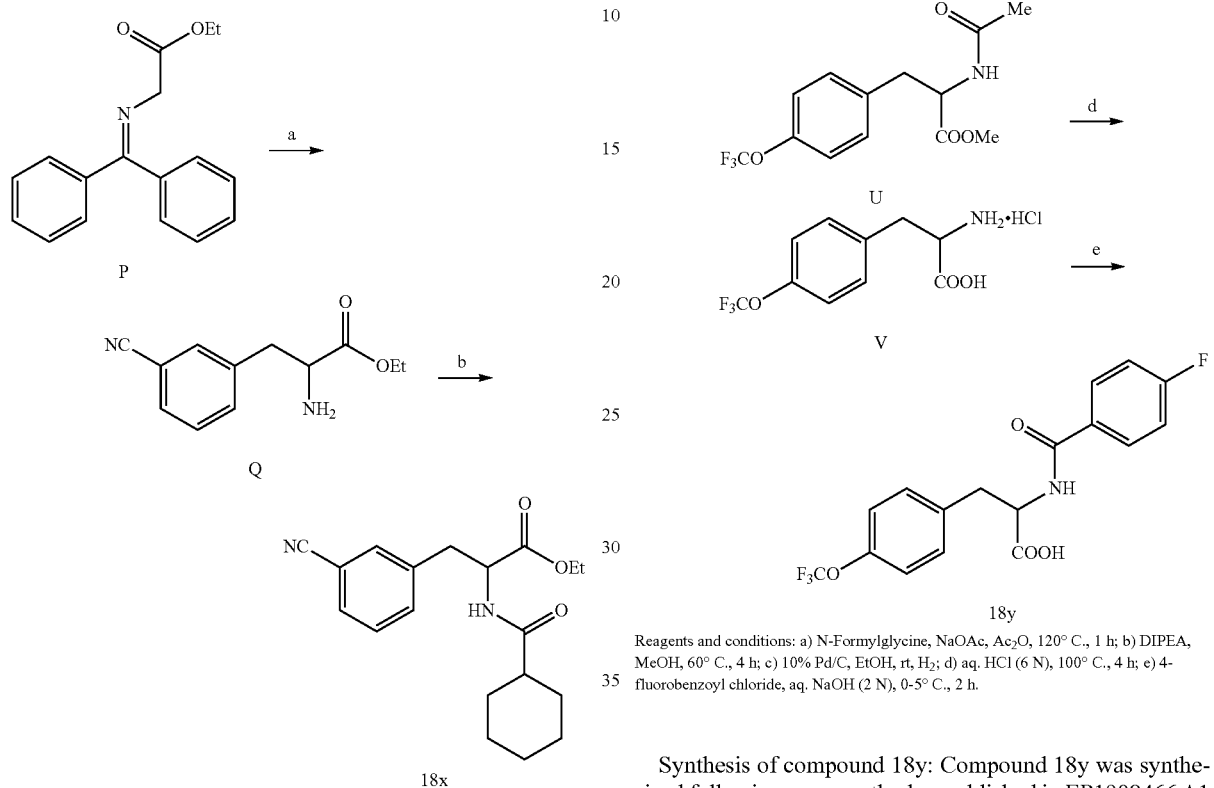

Reagents and conditions: a) 3-(bromomethyl)benzonitrile, TBAB, K$_2$CO$_3$, MeCN, 85° C., 6 h; b) cyclohexanecarbonyl chloride, aq. NaOH (2 N), -5° C., 2 h.

Synthesis of compound 18x: Compound 18x was synthesized following same method as published in U.S. Pat. No. 5,750,520 A1 (1998) and similar to the ones described in Scheme 5.

Scheme 5c: Synthesis of 2-(4-fluorobenzamido)-3-(4-(trifluoromethoxy)phenyl)propanoic acid (18y)

Reagents and conditions: a) N-Formylglycine, NaOAc, Ac$_2$O, 120° C., 1 h; b) DIPEA, MeOH, 60° C., 4 h; c) 10% Pd/C, EtOH, rt, H$_2$; d) aq. HCl (6 N), 100° C., 4 h; e) 4-fluorobenzoyl chloride, aq. NaOH (2 N), 0-5° C., 2 h.

Synthesis of compound 18y: Compound 18y was synthesized following same method as published in EP1908466 A1 and similar to steps described in Scheme 5.

Example-1

Synthesis of (S)—N-(1-((5-(N-(tert-butyl)sulfamoyl)naphthalen-1-yl)amino)-1-oxo-3-phenylpropan-2-yl)benzamide (4b)

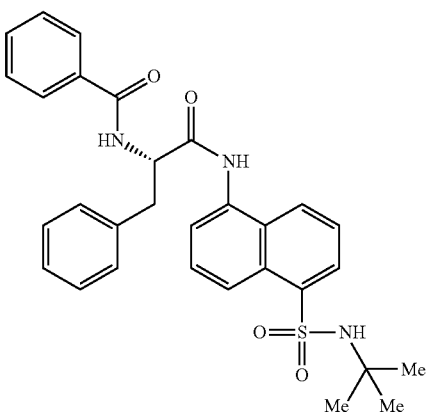 [SMILES: CC(C)(C)NS(=O)(=O)c1cccc2c(NC(=O)[C@H](Cc3ccccc3)NC(=O)c3ccccc3)cccc12]

Synthesis of Sodium 5-acetamidonaphthalene-1-sulfonate (B)

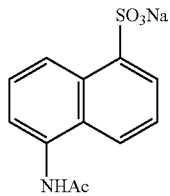

5-Aminonaphthalene-1-sulfonic acid (6.0 g, 26 mmol) was dissolved in water (20 mL) and was cooled to 0° C. 5 N NaOH (11 mL) was added dropwise, stirred for 10 min and reaction solvent was removed by rotary evaporator and washed with toluene to obtain the sodium salt. Acetic anhydride (50 mL) was then added and the reaction mixture was stirred at 100° C. for 2 h. After cooling to room temperature, reaction mixture was poured onto ethanol. The crude product was precipitated out. The solid was filtered, washed with cold ethanol and dried under vacuum to afford B (5.4 g, 70%) as a white solid: $^1$H NMR (400 MHz, DMSO-$d_6$): δ 9.89 (brs, 1H), 8.72 (d, J=8.3 Hz, 1H), 8.03 (d, J=8.9 Hz, 1H), 7.96 (d, J=6.8 Hz, 1H), 7.58 (d, J=7.3 Hz, 1H), 7.47 (t, J=8.05 Hz, 2H), 2.16 (s, 3H).

Synthesis of 5-acetamidonaphthalene-1-sulfonyl chloride (C)

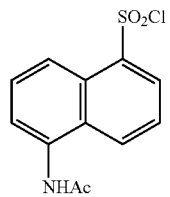 [SMILES: CC(=O)Nc1cccc2c(S(=O)(=O)Cl)cccc12]

A solution of sodium 5-acetamidonaphthalene-1-sulfonate (7 g, 24 mmol) in chlorosulfuric acid (40 mL) was stirred at rt for 16 h. The reaction mixture was poured onto ice water under stirring and the crude product was precipitated out. The precipitate was filtered and dried under vacuum to give C (5 g, 72%) as a white solid: $^1$H NMR (400 MHz, DMSO-$d_6$): δ 9.89 (brs, 1H), 8.71 (d, J=8.4 Hz, 1H), 8.03 (d, J=8.3 Hz, 1H), 7.96 (d, J=7.3 Hz, 1H), 7.59 (d, J=6.5 Hz, 1H), 7.47 (t, J=7.8 Hz, 2H), 2.16 (s, 3H); LCMS (ESI+, m/z): 284 (M+H)$^+$.

Synthesis of N-(5-(N-(tert-butyl)sulfamoyl)naphthalen-1-yl)acetamide (D)

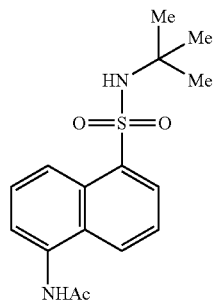 [SMILES: CC(=O)Nc1cccc2c(S(=O)(=O)NC(C)(C)C)cccc12]

Triethylamine (4.1 g, 42 mmol) and 2-methylpropan-2-amine (3.0 g, 42 mmol) were added dropwise to a solution of 5-acetamidonaphthalene-1-sulfonyl chloride (6.0 g, 21.1 mmol) in dry THF (20 mL) at 0° C. Once the addition was complete, the mixture was warmed to rt and was stirred for 16 h. Following slow addition to ice water, the mixture was extracted with ethyl acetate (20 mL) and the extract was washed with saturated aq. NH$_4$Cl solution (2×10 mL), water (1×20 mL) and brine (1×20 mL). The organic layer was dried over anhydrous Na$_2$SO$_4$ and was concentrated in vacuo. The product was purified by CombiFlash using dichloromethane and methanol to obtain the title compound D (4 g, 59%) as a yellow fluffy solid: $^1$H NMR (400 MHz, DMSO-$d_6$): δ 10.03 (brs, 1H), 8.53 (d, J=8.4 Hz, 1H), 8.32 (d, J=8.4 Hz, 1H), 8.20 (d, J=7.2 Hz, 1H), 7.77-7.73 (m, 2H), 7.67 (t, J=8.1 Hz, 2H), 2.10 (s, 3H), 1.05 (s, 9H); LCMS (ESI+, m/z): 321.2 (M+H)$^+$.

Synthesis of 5-amino-N-(tert-butyl)naphthalene-1-sulfonamide (3aa)

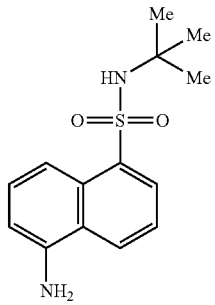 [SMILES: CC(C)(C)NS(=O)(=O)c1cccc2c(N)cccc12]

To a solution of N-(5-(N-(tert-butyl)sulfamoyl)naphthalen-1-yl)acetamide (4 g, 12.5 mmol) in methanol (50 mL) was added with 5 N NaOH (22 mL). The reaction mixture was stirred for 2 h at 100° C. Following removal of most of the solvent in vacuo, the mixture was neutralized with 2 N aq.HCl to give 3aa, which was collected by filtration and dried under vacuum. The title compound (3.2 g, 92%) was obtained as a light brown solid: $^1$H NMR (400 MHz, DMSO-$d_6$): δ 8.33 (d, J=8.8 Hz, 1H), 8.08 (d, J=6.8 Hz, 1H), 7.84(d, J=8.8 Hz, 1H), 7.54 (s, 1H), 7.44 (t, J=7.8 Hz, 1H), 7.36 (t, J=8.3 Hz, 1H), 6.77 (d, J=7.2 Hz, 1H), 5.94 (brs, 2H), 1.03 (s, 9H); LCMS (ESI+, m/z): 279.1 (M+H)$^+$.

Synthesis of benzoyl-L-phenylalanine (3b)

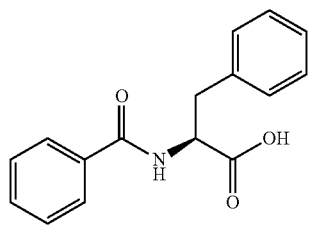 [SMILES: O=C(N[C@@H](Cc1ccccc1)C(=O)O)c1ccccc1]

Benzoyl chloride (1.4 g, 9.9 mmol) was added at ice bath temperature to a stirred suspension of 2 N NaOH solution (11 mL) and L-phenylalanine (1.65 g, 9.9 mmol). The reaction mixture was stirred at rt for 2 h (monitored by TLC). The pH of the reaction mixture was lowered to 5-6 with 2 N aq. HCl. The resultant precipitate was filtered, was washed with water until pH was neutral and was dried under high vacuum to give 3b (2.3 g, 86%) as a white solid: $^1$H NMR (400 MHz, DMSO-$d_6$): δ 12.74 (s, 1H), 8.68 (d, J=7.6 Hz, 1H), 7.79 (d, J=6.8 Hz, 2H), 7.53-7.42 (m, 3H), 7.32-7.15 (m, 5H), 4.64-4.58 (m, 1H), 3.21-3.16 (dd, J=1.1, 14.0 Hz, 1H), 3.09-3.03 (dd, J=10.8, 13.6 Hz, 1H); LCMS (ESI+, m/z): 270.2 (M+H)$^+$.

Synthesis of (S)—N-(1-((5-(N-(tert-butyl)sulfamoyl)naphthalen-1-yl)amino)-1-oxo-3-phenylpropan-2-yl)benzamide (4b)

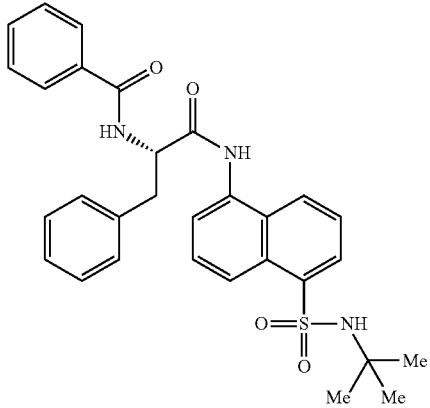 [SMILES: CC(C)(C)NS(=O)(=O)c1cccc2c(NC(=O)[C@H](Cc3ccccc3)NC(=O)c3ccccc3)cccc12]

N-benzoyl-L-phenylalanine (0.2 g, 0.72 mmol) was dissolved in dry DMF (6 mL) and cooled to 0° C. To that solution were added EDC.HCl (0.15 g, 0.72 mmol), and HOBt (0.08 g, 0.54 mmol) and the resultant mixture was stirred for 30 minutes under $N_2$ atmosphere. 5-Amino-N-(tert-butyl)naphthalene-1-sulfonamide (3aa) (0.1 g, 0.37 mmol) was added and the reaction mixture was stirred for 16 h at rt. The reaction mixture was extracted with ethyl acetate (50 mL) and the extract was washed with saturated aq. bicarbonate solution (2×50 mL), water (1×50 mL) and brine (1×50 mL). The organic layer was dried over anhydrous $Na_2SO_4$ and was concentrated under vacuum. The product was isolated by CombiFlash using MeOH in DCM to obtain 4b (0.02 g, 10%) as an off-white solid and was characterized by $^1$H NMR & LC-MS analysis.

Synthesis of compounds 4a, 4c-l: Compounds 4a, 4c-l were synthesized following same procedure as described for synthesis of compound 4b (Scheme-1b).

Example-2

Synthesis of (S)—N-(1(5-(N-(tert-butyl) sulfamoyl) naphthalen-1-yl) amino)-1-oxo-3-phenylpropan-2-yl)-4,4-difluorocyclohexane-1-carboxamide (4n)

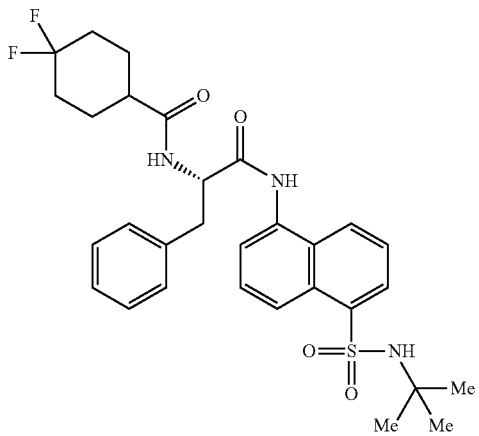 [SMILES: CC(C)(C)NS(=O)(=O)c1cccc2c(NC(=O)[C@H](Cc3ccccc3)NC(=O)C3CCC(F)(F)CC3)cccc12]

Synthesis of ethyl 4,4-difluorocyclohexane-1-carboxylate (F)

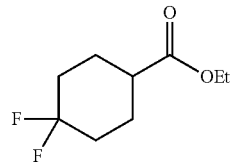 [SMILES: CCOC(=O)C1CCC(F)(F)CC1]

A solution of ethyl 4-oxocyclohexane-1-carboxylate (5 g, 29 mmol) in carbon tetrachloride (150 mL) was slowly added dropwise with DAST (7.7 g, 29 mmol) at rt. The reaction was stirred for 16 h at rt. The mixture was diluted with water and was extracted with ethyl acetate. The organic layer was separated and the aqueous layer was re-extracted with ethyl acetate (3×50 mL). The combined organic layer was washed with water (1×100 mL), brine (1×100 mL), dried over anhydrous $Na_2SO_4$ and concentrated under vacuum to obtain F (3 g, 53%) as a gummy solid: $^1$H NMR (400 MHz, DMSO-$d_6$): δ 4.07 (q, J=7.2 Hz, 2H), 2.26-2.15 (m, 1H), 2.03-1.99 (m, 2H), 1.98-1.90 (m, 2H), 1.87-1.79 (m, 2H), 1.77-1.56 (m, 2H), 1.18 (t, J=7.6 Hz, 3H).

Synthesis of 4,4-difluorocyclohexane-1-carboxylic acid (G)

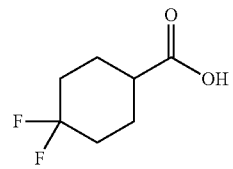

To a stirred solution of ethyl 4,4-difluorocyclohexane-1-carboxylate (3 g, 16 mmol) in ethanol (15 mL) was added a solution of 2 N NaOH (10 mL) at ice bath temperature. The reaction mixture was stirred at rt for 2 h at which point the pH was adjusted to 5-6 with aq. HCl (2 N). The mixture was extracted with EtOAc (3×50 mL) and the combined organic extract was washed with water (1×100 mL), was dried over anhydrous $Na_2SO_4$ and was concentrated under reduced pressure to obtain the title compound G (1.3 g, 51%) as a pale yellow gummy solid: $^1$H NMR (400 MHz, DMSO-$d_6$): δ 12.34 (brs, 1H), 2.18-1.99 (m, 1H), 1.98-1.90 (m, 2H), 1.88-1.81 (m, 2H), 1.78-1.60 (m, 2H), 1.57-1.54 (m, 2H).

Synthesis of methyl (4,4-difluorocyclohexane-1-carbonyl)-L-phenylalaninate (2n)

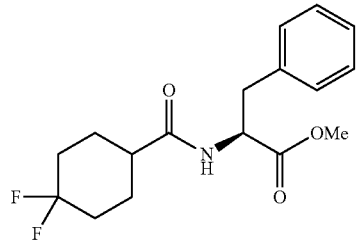 [SMILES: COC(=O)[C@H](Cc1ccccc1)NC(=O)C1CCC(F)(F)CC1]

4,4-Difluorocyclohexane-1-carboxylic acid (0.5 g, 3 mmol) was dissolved in dry DMF (3 mL) and cooled to 0° C. EDC.HCl (1 g, 5.5 mmol), HOBt (0.9 g, 5.5 mmol) and DIPEA (1.1 mL, 7.6 mmol) were added. The reaction mixture was stirred for 20 minutes and then methyl L-phenylalaninate hydrochloride (0.52 g, 2.43 mmol) was added and the mixture was stirred for 16 h at room temperature. The reaction mixture was diluted with ethyl acetate (20 mL) and was washed with saturated aq. NH$_4$Cl solution (1×20 mL), water (1×20 mL) and brine (1×20 mL). The organic layer was dried over anhydrous Na$_2$SO$_4$ and was concentrated under vacuum. The product was isolated by Combi-Flash chromatography using hexane: EtOAc to afford the title compound (0.6 g, 76%) as a light yellow gummy liquid. The product was confirmed by $^1$H NMR and LC-MS analysis. $^1$H NMR (400 MHz, DMSO-d$_6$): δ 8.31 (d, J=7.6 Hz, 1H), 7.29-7.20 (m, 5H), 4.46 (q, J=8.8 Hz, 1H), 3.60 (s, 3H), 3.07-3.02 (m, 1H), 2.91-2.85 (m, 1H), 2.27-2.24 (m, 1H), 1.83-1.42 (m, 8H); LCMS (ESI+, m/z): 326.2 (M+H)$^+$.

Synthesis of (4,4-difluorocyclohexane-1-carbonyl)-L-phenylalanine (3n)

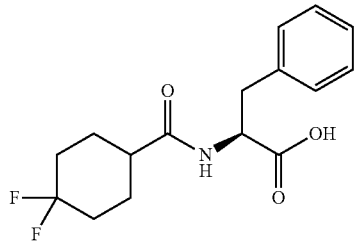 [SMILES: O=C(N[C@@H](Cc1ccccc1)C(=O)O)C1CCC(F)(F)CC1]

Methyl (4,4-difluorocyclohexane-1-carbonyl)-L-phenylalaninate (0.60 g, 1.8 mmol) was taken up in a mixture of THF (4 mL) and MeOH (2 mL). To the reaction mixture, lithium hydroxide monohydrate (0.4 g, 9.2 mmol) dissolved in 2 mL of water was added and stirred at rt for 1 h. The pH of the reaction mixture was adjusted to 2-3 by dropwise addition of 2 N aq.HCl solution. The organic layer was separated and the aqueous layer was extracted with EtOAc (3×50 mL). The combined organic layer was washed with water (1×50 mL), brine (1×50 mL), dried over anhydrous Na$_2$SO$_4$ and concentrated under vacuum to obtain 3n (0.3 g, 52%) as a light yellow gummy solid: $^1$H NMR (400 MHz, DMSO-d$_6$): δ 12.6 (brs, 1H), 8.15 (d, J=8.0 Hz, 1H), 7.28-7.17 (m, 5H), 4.45-4.40 (m, 1H), 3.07 (dd, J=14.0, 4.4 Hz, 1H), 2.86 (dd, J=13.2, 4.0 Hz, 1H), 2.4-2.2 (m, 1H), 1.98-1.57 (m, 8H); LCMS (ESI+, m/z): 312.2 (M+H)$^+$;

Synthesis of (S)—N-(1-((5-(N-(tert-butyl)sulfamoyl)naphthalen-1-yl)amino)-1-oxo-3-phenylpropan-2-yl)-4,4-difluorocyclohexane-1-carboxamide (4n)

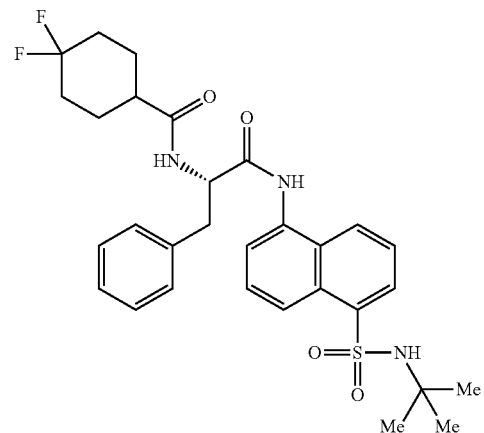 [SMILES: CC(C)(C)NS(=O)(=O)c1cccc2c(NC(=O)[C@H](Cc3ccccc3)NC(=O)C3CCC(F)(F)CC3)cccc12]

(4,4-Difluorocyclohexane-1-carbonyl)-L-phenylalanine (0.3 g, 0.96 mmol) was dissolved in dry DMF (2 mL) and cooled to 0° C. To this solution were added EDC.HCl (0.37 g, 1.92 mmol), and HOBt (0.3 g, 1.92 mmol). The reaction mixture was stirred for 0.5 h and then 5-amino-N-(tert-butyl) naphthalene-1-sulfonamide (0.135 g, 0.49 mmol) was added. The reaction mixture was stirred for 48 h at rt. The reaction mixture was diluted with ethyl acetate (40 mL) and was washed with saturated aq. NH$_4$Cl solution (2×10 mL), water (1×20 mL) and brine (1×20 mL). The organic layer was dried over anhydrous Na$_2$SO$_4$ and was concentrated under vacuum. The product was isolated by CombiFlash using hexane: EtOAc to obtain 4n (0.06 g, 11%) as an off-white solid. The structure of the product was confirmed by $^1$H NMR and LCMS analysis.

Synthesis of Compound 4m, 4o-z: Compound 4m, 4o-z were synthesized following same procedure as described for compound 4n (Scheme-1c).

TABLE 1

4a-z

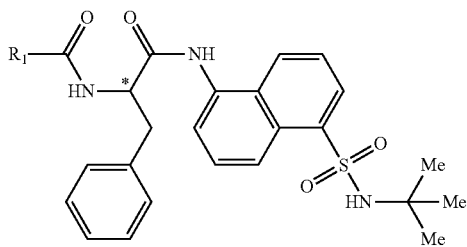

| Compound No. (chirality) | R$_1$ | Analytical Data |
|---|---|---|
| 4a (R) | 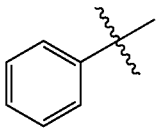 [SMILES: *c1ccccc1] | $^1$H NMR (400 MHz, DMSO-d$_6$): δ 10.29 (s, 1H), 8.82 (d, J = 8.9 Hz, 1H), 8.56 (d, J = 8.3 Hz, 1H), 8.19 (d, J = 6.9 Hz, 1H), 8.13 (d, J = 8.8 Hz, 1H), 7.88 (d, J = 7.3 Hz, 2H), 7.78 (s, 1H), 7.69-7.45 (m, 8H), 7.33 (t, J = 7.3 Hz, 2H), 7.25-7.22 (m, 1H), 5.04-5.02 (m, 1H), 3.25-3.19 (m, 1H), 1.05 (s, 9H); LCMS (ESI+, m/z): 530.3 (M + H). |

TABLE 1-continued 4a-z

[Structure: R₁-C(=O)-NH-CH(*)(CH₂-phenyl)-C(=O)-NH-naphthalene-SO₂-NH-C(Me)(Me)(Me)]

| Compound No. (chirality) | R₁ | Analytical Data |
|---|---|---|
| 4b (S) | phenyl-CH< | ¹H NMR (400 MHz, DMSO-d6): δ 10.29 (s, 1H), 8.82 (d, J = 7.0 Hz, 1H), 8.57 (d, J = 8.4 Hz, 1H), 8.19 (d, J = 6.8 Hz, 1H), 8.13 (d, J = 8.8 Hz, 1H), 7.89 (d, J = 6.8 Hz, 2H), 7.78 (s, 1H), 7.69-7.60 (m, 3H), 7.52-7.42 (m, 5H), 7.32-7.00 (m, 3H), 5.05-5.0 (q, J = 8.98 Hz, 1H), 3.25-3.19 (m, 1H), 1.05 (s, 9H); LCMS (ESI+, m/z): 530.2 (M + H)+. |
| 4c (S) | cyclohexyl-CH< | ¹H NMR (400 MHz, DMSO-d₆): δ 10.12 (s, 1H), 8.55 (d, J = 8.8 Hz, 1H), 8.18 (d, J = 8.4 Hz, 1H), 8.13 (d, J = 7.8 Hz, 1H), 8.02 (d, J = 8.8 Hz, 1H), 7.78 (s, 1H), 7.68-7.64 (m, 1H), 7.61-7.57 (m, 2H), 7.36-7.24 (m, 5H), 4.83-4.81 (m, 1H), 3.16-3.13 (m, 1H), 3.02-2.98 (m, 1H), 2.67 (t, J = 1.2 Hz, 1H), 1.69-1.57 (m, 5H), 1.33-1.07 (m, 5H), 1.05 (s, 9H). LCMS (ESI+, m/z): 536.3 (M + H)⁺. |
| 4d (S) | cyclopropyl-CH< | ¹H NMR (400 MHz, DMSO-d₆): δ 10.16 (s, 1H), 8.58-8.53 (m, 2H), 8.18 (d, J = 7.3 Hz, 1H), 7.94 (d, J = 8.8 Hz, 1H), 7.77 (s, 1H), 7.65-7.55 (m, 3H), 7.38-7.26 (m, 5H), 4.86-4.85 (m, 1H), 3.13-3.11 (m, 1H), 3.04-3.02 (m, 1H), 1.73-1.70 (m, 1H), 1.05 (s, 9H), 0.68-.067 (m, 4H); LCMS (ESI+, m/z): 494.2 (M + H)⁺. |
| 4e (S) | phenyl-CH₂-CH< | ¹H NMR (400 MHz, DMSO-d₆): δ 10.20 (s, 1H), 8.58 (t, J = 7.9 Hz, 2H), 8.19 (d, J = 7.2 Hz, 1H), 7.97 (d, J = 8.0 Hz, 1H), 7.77 (s, 1H), 7.68 (t, J = 7.9 Hz, 1H), 7.58-7.53 (m, 2H), 7.35-7.17 (m, 10H), 4.89-4.83 (m, 1H), 3.54-3.44 (m, 2H), 3.19-3.14 (m, 1H), 3.0-2.98 (m, 1H), 1.05 (s, 9H); LCMS (ESI+, m/z): 544.2 (M + H)⁺. |
| 4f (S) | phenyl-CH₂-CH₂-CH< | ¹H NMR (400 MHz, DMSO-d₆): δ 10.18 (s, 1H), 8.56 (d, J = 8.8 Hz, 1H), 8.38 (d, J = 7.2 Hz, 1H), 8.19 (d, J = 7.2 Hz, 1H), 7.98 (d, J = 8.8 Hz, 1H), 7.77 (s, 1H), 7.68 (t, J = 7.7 Hz, 1H), 7.57-7.56 (m, 2H), 7.31-7.25 (m, 4H), 7.23-7.12 (m, 6H), 4.90-4.85 (m, 1H), 3.14-3.09 (m, 1H), 3.0-2.95 (m, 1H), 2.80 (t, J = 7.6 Hz, 2H), 2.47-2.43 (m, 2H), 1.05 (s, 9H). LCMS (ESI+, m/z): 558.3 (M + H)⁺. |
| 4g (S) | 4-chlorophenyl-CH< | ¹H NMR (400 MHz, DMSO-d₆): δ 10.30 (s, 1H), 8.94 (d, J = 7.6 Hz, 1H), 8.57 (d, J = 8.2 Hz, 1H), 8.20 (d, J = 7.6 Hz, 1H), 8.12 (d, J = 8.8 Hz, 1H), 7.92 (d, J = 8.2 Hz, 2H), 7.78 (s, 1H), 7.69-7.60 (m, 3H), 7.56 (d, J = 8.4 Hz, 2H), 7.45 (d, J = 7.6 Hz, 2H), 7.34 (t, 2H, J = 7.6 Hz), 7.25-7.22 (m, 1H), 5.03-4.97 (m, 1H), 3.23-3.17 (m, 1H), 1.05 (s, 9H); LCMS (ESI+, m/z): 564.2 (M + H)⁺. |
| 4h (S) | 2-thienyl-CH< | ¹H NMR (400 MHz, DMSO-d₆): δ 10.30 (s, 1H), 8.87 (d, J = 7.6 Hz, 1H), 8.57 (d, J = 8.0 Hz, 1H), 8.20 (d, J = 7.6 Hz, 1H), 8.08 (d, J = 8.0 Hz, 1H), 7.93 (d, J = 3.6 Hz, 1H), 7.78-7.75 (m, 2H), 7.68-7.59 (m, 3H), 7.45 (d, J = 7.2 Hz, 2H), 7.34 (t, J = 7.2 Hz, 2H), 7.25-7.21 (m, 1H), 7.17 (t, J = 4.2 Hz, 1H), 5.03-4.97 (m, 1H), 3.21-3.16 (m, 2H), 1.05 (s, 9H); LCMS (ESI+, m/z): 536.2 (M + H)⁺. |
| 4i (S) | 4-methylphenyl-CH< | ¹H NMR (400 MHz, DMSO-d₆): δ 10.25 (s, 1H), 8.73 (d, J = 8.0 Hz, 1H), 8.57 (d, J = 8.4 Hz, 1H), 8.20 (d, J = 7.2 Hz, 1H), 8.13 (d, J = 8.4 Hz, 1H), 7.81-7.78 (m, 3H), 7.67-7.60 (m, 3H), 7.46 (d, J = 7.2 Hz, 2H), 7.33-7.23 (m, 5H), 5.09-4.97 (m, 1H), 3.27-3.22 (m, 2H), 2.35 (s, 3H), 1.05 (s, 9H); LCMS (ESI+, m/z): 544.2 (M + H)⁺. |

TABLE 1-continued 4a-z

| Compound No. (chirality) | R₁ | Analytical Data |
|---|---|---|
| 4j (S) | 4-fluorophenyl | ¹H NMR (400 MHz, DMSO-d₆): δ 10.30 (s, 1H), 8.87 (d, J = 7.2 Hz, 1H), 8.56 (d, J = 8.4 Hz, 1H), 8.19 (d, J = 7.2 Hz, 1H), 8.12 (d, J = 8.8 Hz, 1H), 7.97 (t, J = 6.6 Hz, 2H), 7.78 (s, 1H), 7.67-7.60 (m, 3H), 7.45 (d, J = 8.0 Hz, 2H), 7.34-7.21 (m, 5H), 5.04 (q, J = 8.0 Hz, 1H), 3.23 (m, 2H), 1.05 (s, 9H); LCMS (ESI+, m/z): 548.2 (M + H)⁺. |
| 4k (S) | tetrahydropyran-4-yl | ¹H NMR (400 MHz, DMSO-d₆): δ 10.15 (s, 1H), 8.56 (d, J = 8.4 Hz, 1H), 8.24 (d, J = 8.0 Hz, 1H), 8.20 (d, J = 7.2 Hz, 1H), 8.03 (d, J = 8.0 Hz, 1H), 7.78 (s, 1H), 7.68 (t, J = 8.0 Hz, 1H), 7.61-7.58 (m, 2H), 7.36-7.24 (m, 5H), 4.85-4.83 (m, 1H), 3.85 (t, J = 12.6 Hz, 2H), 3.19-3.14 (m, 3H), 3.02-2.99 (m, 1H), 1.57-1.48 (m, 5H), 1.05 (s, 9H); LCMS (ESI+, m/z): 538.2 (M + H)⁺. |
| 4l (S) | cyclopentyl | ¹H NMR (500 MHz, DMSO-d₆): δ 10.17 (s, 1H), 8.55 (d, J = 8.8 Hz, 1H), 8.24 (d, J = 7.7 Hz, 1H), 8.18 (d, J = 7.3 Hz, 1H), 8.01 (d, J = 8.5 Hz, 1H), 7.81 (s, 1H), 7.66 (t, J = 8.0 Hz, 1H), 7.59-7.57 (m, 2H), 7.36-7.24 (m, 5H), 4.84 (q, J = 6.6 Hz, 1H), 3.14-3.13 (m, 1H), 3.01-2.99 (m, 1H), 2.66-2.64 (m, 1H), 1.71-1.58 (m, 5H), 1.49-1.47 (m, 3H), 1.05 (s, 9H); LCMS (ESI+, m/z): 522.3 (M + H)⁺. |
| 4m (S) | 6-methylpyridin-2-yl | ¹H NMR (400 MHz, DMSO-d₆): δ 10.35 (s, 1H), 8.72 (d, J = 8.3 Hz, 1H), 8.56 (d, J = 8.3 Hz, 1H), 8.19 (d, J = 6.8 Hz, 1H), 8.01 (d, J = 8.3 Hz, 1H), 7.91-7.85 (m, 2H), 7.78 (s, 1H), 7.69-7.59 (m, 3H), 7.57-7.48 (m, 1H), 7.37-7.24 (m, 5H), 5.15 (q, J = 7.3 Hz, 1H), 3.34-3.27 (m, 2H), 2.57 (s, 3H), 1.05 (s, 9H); LCMS (ESI+, m/z): 545.2 (M + H)⁺. |
| 4n (S) | 4,4-difluorocyclohexyl | 1H NMR (400 MHz, DMSO-d₆): δ 10.22 (brs, 1H), 8.55 (d, J = 8.8 Hz, 1H), 8.36 (d, J = 7.2 Hz, 1H), 8.19 (d, J = 6.8 Hz, 1H), 8.03 (d, J = 8.4 Hz, 1H), 7.82 (s, 1H), 7.69-7.61 (m, 1H), 7.59-7.58 (m, 2H), 7.36-7.30 (m, 4H), 7.26-7.24 (m, 1H), 4.85 (q, J = 8.4 Hz, 1H), 3.20-3.15 (m, 1H), 3.02-2.96 (m, 1H), 2.44-2.33 (m, 1H), 2.2-1.48 (m, 8H), 1.05 (s, 9H); LCMS (ESI+, m/z): 572.3 (M + H)+. |
| 4o (S) | pyrimidin-2-yl | ¹H NMR (400 MHz, DMSO-d₆): δ 10.36 (s, 1H), 9.03-8.98 (m, 3H), 8.57 (d, J = 8.4 Hz, 1H), 8.20 (d, J = 7.6 Hz, 1H), 8.08 (d, J = 8.8 Hz, 1H), 7.82 (s, 1H), 7.72-7.59 (m, 4H), 7.38 (d, J = 7.6 Hz, 2H), 7.33 (t, J = 7.6 Hz, 2H), 7.26 (d, J = 7.2 Hz, 1H), 5.15 (q, J = 7.2 Hz, 1H), 3.34-3.31 (m, 2H), 1.04 (s, 9H); LCMS (ESI+, m/z): 532.3 (M + H)⁺. |
| 4p (S) | cycloheptyl | ¹H NMR (400 MHz, DMSO-d₆): δ 10.15 (s, 1H), 8.55 (d, J = 8.8 Hz, 1H), 8.17 (t, J = 7.8 Hz, 2H), 8.01 (d, J = 8.3 Hz, 1H), 7.81 (s, 1H), 7.67 (t, J = 8.0 Hz, 1H), 7.60-7.56 (m, 2H), 7.36-7.22 (m, 5H), 4.81 (q, J = 6.9 Hz, 1H), 3.17-3.12 (m, 1H), 3.01-2.95 (m, 1H), 2.40-2.35 (m, 1H), 1.74-1.43 (m, 12H), 1.05 (s, 9H); LCMS (ESI+, m/z): 550.3 (M + H)⁺. |
| 4q (S) | thiazol-2-yl | ¹H NMR (400 MHz, DMSO-d₆): δ 10.32 (s, 1H), 8.85 (d, J = 7.9 Hz, 1H), 8.57 (d, J = 8.3 Hz, 1H), 8.21 (d, J = 6.9 Hz, 1H), 8.11 (d, J = 8.3 Hz, 1H), 8.05 (d, J = 7.9 Hz, 2H), 7.85 (s, 1H), 7.78-7.6 (m, 3H), 7.39 (d, J = 7.4 Hz, 2H), 7.33-7.21 (m, 3H), 5.06 (q, J = 7.3 Hz, 1H), 3.34 (s, 2H), 1.04 (s, 9H); LCMS (ESI+, m/z): 537.2 (M + H)⁺. |

TABLE 1-continued 4a-z

| Compound No. (chirality) | R₁ | Analytical Data |
|---|---|---|
| 4r (S) | 4-cyanophenyl | ¹H NMR (400 MHz, DMSO-d₆): δ 10.32 (s, 1H), 9.13 (d, J = 7.9 Hz, 1H), 8.57 (d, J = 8.3 Hz, 1H), 8.20 (d, J = 7.4 Hz, 1H), 8.11 (d, J = 8.8 Hz, 1H), 8.03 (d, J = 8.4 Hz, 2H), 7.97 (d, J = 8.3 Hz, 2H), 7.79 (s, 1H), 7.69-7.60 (m, 3H), 7.45 (d, J = 7.4 Hz, 2H), 7.33 (t, J = 7.3 Hz, 2H), 7.24 (t, J = 7.3 Hz, 1H), 5.04 (q, J = 6.9 Hz, 1H), 2.49-2.33 (m, 2H), 1.05 (s, 9H); LCMS (ESI+, m/z): 555.2 (M + H)⁺. |
| 4s (S) | 1-adamantyl | ¹H NMR (400 MHz, DMSO-d₆): δ 10.09 (s, 1H), 8.55 (d, J = 8.4 Hz, 1H), 8.19 (d, J = 6.9 Hz, 1H), 8.08 (d, J = 8.3 Hz, 1H), 7.78 (s, 1H), 7.69-7.61 (m, 3H), 7.53 (d, J = 7.9 Hz, 1H), 7.36-7.29 (m, 4H), 7.24 (d, J = 6.3 Hz, 1H), 4.83 (q, J = 6.4 Hz, 1H), 3.25-3.12 (m, 1H), 1.95 (s, 4H), 1.75 (s, 6H), 1.65 (s, 6H), 1.05 (s, 9H); LCMS (ESI+, m/z): 588.3 (M + H)⁺. |
| 4t (S) | 4-methylcyclohexyl | ¹H NMR (400 MHz, DMSO-d₆): δ 10.12 (s, 1H), 8.55 (d, J = 8.3 Hz, 1H), 8.19-8.13 (m, 1H), 8.07-8.00 (m, 1H), 7.66 (t, J = 8.0 Hz, 1H), 7.61 (t, J = 8.1 Hz, 3H), 7.36-7.31 (m, 4H), 7.29-7.22 (m, 1H), 4.87-4.81 (m, 1H), 3.26-3.18 (m, 1H), 3.16-2.98 (m, 1H), 2.67-2.55 (m, 1H), 1.72-1.58 (m, 3H), 1.40-1.20 (m, 5H), 1.05 (s, 9H), 0.84 (d, J = 7.4 Hz, 4H); LCMS (ESI+, m/z): 550.3 (M + H)⁺. |
| 4u (S) | tetrahydrofuran-2-yl | ¹H NMR (400 MHz, DMSO-d₆): δ 10.24 (s, 0.41H), 10.20 (s, 0.53H), 8.58-8.55 (m, 1H), 8.21-8.19 (m, 1H), 8.11 (d, J = 8.4 Hz, 0.4H), 8.05 (d, J = 8.8 Hz, 0.56 H), 7.90-7.85 (m, 1H), 7.79 (s, 1H), 7.70-7.58 (m, 3H), 7.33-7.19 (m, 5H), 4.94-4.85 (m, 1H), 4.27-4.23 (m, 1H), 3.91-3.70 (m, 2H), 3.26-3.10 (m, 2H), 2.12-1.99 (m, 1H), 1.80-1.71 (m, 2H), 1.69-1.61 (m, 0.7H + 0.6H), 1.05 (s, 9H); LCMS (ESI+, m/z): 524.2 (M + H)⁺ |
| 4v (S) | 4-methoxyphenyl | ¹H NMR (400 MHz, DMSO-d₆): δ 10.27 (s, 1H), 8.66 (d, J = 7.8 Hz, 1H), 8.55 (d, J = 8.3 Hz, 1H), 8.19 (d, J = 6.9 Hz, 1H), 8.12 (d, J = 8.8 Hz, 1H), 7.88 (d, J = 8.8 Hz, 2H), 7.78 (s, 1H), 7.69-7.59 (m, 3H), 7.45 (d, J = 7.3 Hz, 2H), 7.32 (t, J = 7.6 Hz, 2H), 7.23 (t, J = 6.7 Hz, 1H), 7.00 (d, J = 8.3 Hz, 2H), 5.00 (q, J = 6.9 Hz, 1H), 3.80 (s, 3H), 3.28-3.21 (m, 2H), 1.05 (s, 9H); LCMS (ESI+, m/z): 560.2 (M + H)⁺. |
| 4w (S) | 4-hydroxyphenyl | ¹H NMR (400 MHz, DMSO-d₆): δ 10.24 (brs, 1H), 9.96 (s, 1H), 8.53 (t, J = 8.0 Hz, 2H), 8.18 (d, J = 7.4 Hz, 1H), 8.11 (d, J = 8.4 Hz, 1H), 7.75 (d, J = 7.9 Hz, 3H), 7.67-7.58 (m, 3H), 7.43 (d, J = 7.3 Hz, 2 H), 7.31 (d, J = 7.3 Hz, 2H), 7.28-7.19 (m, 1H), 6.78 (d, J = 8.8 Hz, 2H), 4.99-4.94 (m, 1H), 3.25-3.16 (m, 2 H), 1.04 (s, 9 H); LCMS (ESI+, m/z): 546.2 (M + H)⁺. |
| 4x (S) | pyridin-2-yl | ¹H NMR (400 MHz, DMSO-d₆): δ 10.34 (s, 1H), 8.86 (d, J = 8.0 Hz, 1H), 8.68 (d, , J = 4.4 Hz, 1H), 8.58 (d, , J = 8.4 Hz, 1H), 8.20 (d, J = 7.2 Hz, 1H), 8.07-8.0 (m, 3H), 7.78 (s, 1H), 7.69-7.58 (m, 4H), 7.37-7.22 (m, 5H), 5.17-5.12 (m, 1H), 3.41-3.33 (m, 2H), 1.05 (s, 9H); LCMS (ESI+, m/z): 531.2 (M + H)⁺. |
| 4y (S) | 1H-pyrrol-2-yl | ¹H NMR (400 MHz, DMSO-d₆): δ 11.47 (s, 1H), 10.25 (s, 1H), 8.55 (d, J = 8.4 Hz, 1H), 8.32 (d, J = 7.6 Hz, 1H), 8.18 (d, J = 6.8 Hz, 1H), 8.08 (d, J = 8.0 Hz, 1H), 7.77 (s, 1H), 7.68-7.57 (m, 3H), 7.43 (d, J = 7.2 Hz, 2H), 7.31 (t, J = 7.2 Hz, 2H), 7.24 (d, J = 7.2 Hz, 1H), 6.91 (s, 1H), 6.86 (s, 1H), 6.09 (s, 1H), 4.99 (q, J = 6.4 Hz, 1H), 3.27-3.13 (m, 2H), 1.05 (s, 9H); LCMS (ESI+, m/z): 519.2 (M + H)⁺. |

TABLE 1-continued 4a-z

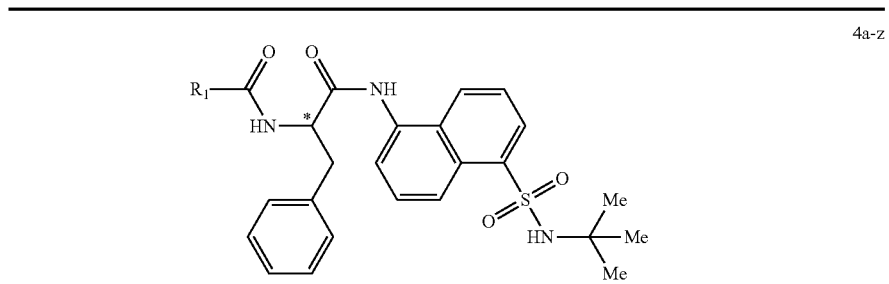

| Compound No. (chirality) | R₁ | Analytical Data |
|---|---|---|
| 4z (S) | 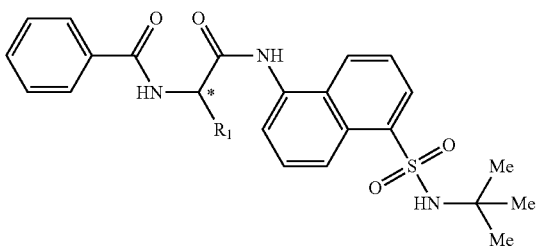 | ¹H NMR (400 MHz, DMSO-d₆): δ 10.25 (s, 1H), 8.62 (d, J = 8.0 Hz, 1H), 8.57 (d, , J = 8.0 Hz, 1H), 8.20 (d, , J = 7.6 Hz, 1H), 8.09 (d, J = 8.4 Hz, 1H), 7.85 (s, 2H), 7.68-7.59 (m, 3H), 7.42 (d, J = 7.2 Hz, 2H), 7.33-7.20 (m, 4H), 6.62 (s, 1H), 5.01-4.99 (m, 1H), 3.27-3.31 (m, 2H), 1.05 (s, 9H); LCMS (ESI+, m/z): 520.2 (M + H)⁺; |

Synthesis of compounds 7a-n: Compounds 7a-n were synthesized following same procedure as described in Scheme 1b.

TABLE 2

7a-n

| Compound No and chirality | R₁ | Analytical Data |
|---|---|---|
| 7a (S) | 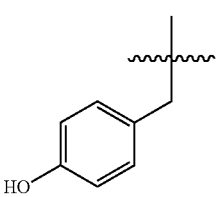 | ¹H NMR (400 MHz, DMSO-d₆): δ 10.24 (s, 1H), 8.68 (d, J = 7.6 Hz, 1H), 8.57 (d, J = 7.6 Hz, 1H), 8.31 (d, J = 8.4 Hz, 1H), 8.20 (d, J = 7.2 Hz, 1H), 7.96 (d, J = 7.6 Hz, 2H), 7.78 (s, 1H), 7.76-7.66 (m, 3H), 7.57-7.46 (m, 3H), 4.80-4.78 (m, 1H), 1.94-1.76 (m, 3H), 1.05 (s, 9H), 1.02-0.89 (m, 6H); LCMS (ESI+, m/z): 496.2 (M + H)⁺. |
| 7b (S) | | ¹H NMR (400 MHz, DMSO-d₆): δ 10.27 (s, 1H), 9.23 (s, 1H), 8.77 (d, J = 7.2 Hz, 1H), 8.56 (d, J = 8.4 Hz, 1H), 8.19 (d, , J = 7.2 Hz, 1H), 8.10 (d, J = 8.8 Hz, 1H), 7.89 (d, J = 7.6 Hz, 2H) 7.80 (s, 1H), 7.69-7.60 (m, 3H), 7.54-7.46 (m, 3H), 7.24 (d, J = 7.8 Hz, 2H) 6.70 (d, J = 8.4 Hz, 2H), 4.94-4.92 (m, 1H), 3.17-3.10 (m, 2H), 1.05 (s, 9H); LCMS (ESI+, m/z): 546.3 (M + H)⁺. |
| 7c (S) | 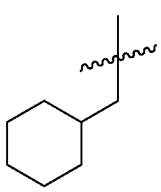 [SMILES: *CC1CCCCC1] | ¹H NMR (400 MHz, DMSO-d₆): δ 10.26 (s, 1H), 8.69 (d, J = 7.2 Hz, 1H), 8.57 (d, J = 8.0 Hz, 1H), 8.32 (d, J = 8.4 Hz, 1H), 8.20 (d, J = 7.2 Hz, 1H), 7.96 (d, J = 7.2 Hz, 2H), 7.81 (s, 1H), 7.69-7.66 (m, 3H), 7.56-7.47 (m, 3H), 4.90-4.80 (m, 1H), 1.85-1.79 (m, 4H), 1.70-1.64 (m, 3H), 1.55-1.49 (m, 1H), 1.23-1.15 (m, 5H), 1.05 (s, 9H); LCMS (ESI+, m/z): 536.3 (M + H)⁺. |

TABLE 2-continued 7a-n

| Compound No and chirality | R₁ | Analytical Data |
|---|---|---|
| 7d (S) | 2-chlorobenzyl (with CH(CH₃)) | ¹H NMR (400 MHz, DMSO-d₆): δ 10.24 (s, 1H), 8.92 (d, J = 7.2 Hz, 1H), 8.57 (d, J = 8.8 Hz, 1H), 8.19 (d, J = 7.2 Hz, 1H), 8.11 (d, J = 8.0 Hz, 1H), 7.92 (d, J = 7.2 Hz, 2H), 7.80 (s, 1H), 7.69-7.57 (m, 3H), 7.55-7.46 (m, 5H), 7.29-7.28 (m, 2H), 5.09 (q, J = 7.2 Hz, 1H), 3.49-3.30 (m, 2H), 1.04 (s, 9H); LCMS (ESI+, m/z): 564.2 (M + H)⁺. |
| 7e (S) | 4-fluorobenzyl | ¹H NMR (400 MHz, DMSO-d₆): δ 10.30 (s, 1H), 8.83 (d, J = 7.8 Hz, 1H), 8.57 (d, J = 7.8 Hz, 1H), 8.20 (d, J = 7.3 Hz, 1H), 8.16 (d, J = 8.3 Hz, 1H), 7.88 (d, J = 6.9 Hz, 2H), 7.79 (s, 1H), 7.69-7.61 (m, 3H), 7.56-7.45 (m 5H), 7.15 (t, J = 8.8 Hz, 2H), 5.03-4.98 (m, 1H), 3.43-3.21 (m, 2H), 1.05 (s, 9H); LCMS (ESI+, m/z): 548.2 (M + H)⁺. |
| 7f (S) | 4-methoxybenzyl | ¹H NMR (400 MHz, DMSO-d₆): δ 10.31 (s, 1H), 8.81 (d, J = 7.8 Hz, 1H), 8.56 (d, J = 8.3 Hz, 1H), 8.20 (d, J = 6.9 Hz, 1H), 8.12 (d, J = 8.6 Hz, 1H), 7.89 (d, J = 6.9 Hz, 2H), 7.82 (s, 1H), 7.68-7.61 (m, 3H), 7.59-7.46 (m, 3H), 7.37 (d, J = 8.8 Hz, 2H), 6.88 (d, J = 8.8 Hz, 2H), 4.95-4.65 (m, 1H), 3.71 (s, 3H), 3.50-3.30 (m, 2H), 1.05 (s, 9H); LCMS (ESI+, m/z): 560.2 (M + H)⁺. |
| 7g (S) | phenethyl | ¹H NMR (400 MHz, DMSO-d₆): δ 10.24 (s, 1H), 8.80 (d, J = 7.4 Hz, 1H), 8.58 (t, J = 4.9 Hz, 1H), 8.32 (d, J = 8.3 Hz, 1H), 8.19 (d, J = 7.4 Hz, 1H), 7.99 (d, J = 8.0 Hz, 2H), 7.78 (s, 1H), 7.68-7.64 (m, 3H), 7.59-7.49 (m, 3H), 7.32-7.21 (m, 5H), 4.75 (q, J = 7.4 Hz, 1H), 2.89-2.67 (m, 2H), 2.33-2.08 (m, 2H), 1.05 (s, 9H); LCMS (ESI+, m/z): 544.3 (M + H)⁺. |
| 7h (S) | cyclopropylmethyl | ¹H NMR (400 MHz, DMSO-d₆): δ 10.25 (s, 1H), 8.69 (d, J = 7.3 Hz, 1H), 8.57 (d, J = 6.4 Hz, 1H), 8.35 (d, J = 8.3 Hz, 1H), 8.20 (d, J = 7.3 Hz, 1H), 7.97 (d, J = 7.8 Hz, 2H), 7.78 (s, 1H), 7.67 (t, J = 5.8 Hz, 3H), 7.57-7.47 (m, 3H), 4.83 (q, J = 6.4 Hz, 1H), 1.99 (t, J = 14.2 Hz, 1H), 1.75-1.71 (m, 1H), 1.05 (s, 9H), 0.96-0.85 (m, 1H), 0.84-0.28 (m, 2H), 0.27-0.14 (m, 2H); LCMS (ESI+, m/z): 494.2 (M + H)⁺. |
| 7i (S) | imidazolylmethyl | ¹H NMR (400 MHz, DMSO-d₆): δ 14.25-13.91 (brs, 1H), 10.18 (s, 1H), 8.94-8.90 (m, 2H), 8.52 (d, J = 8.4 Hz, 1H), 8.14 (d, J = 7.6 Hz, 2H), 7.87 (d, J = 7.2 Hz, 2H), 7.74 (s 1H), 7.65-7.42 (m, 7H), 5.0 (q, J = 6.8 Hz, 1H), 3.43-3.22 (m, 2H), 0.98 (s, 9H); LCMS (ESI+, m/z): 520.2 (M + H)⁺. |
| 7j (S) | 4-cyanobenzyl | ¹H NMR (400 MHz, DMSO-d₆): δ 10.35 (s, 1H), 8.90 (d, J = 7.8 Hz, 1H), 8.57 (d, J = 7.4 Hz, 1H), 8.21-8.17 (m, 2H), 7.87 (d, J = 7.9 Hz, 2H), 7.81 (d, J = 8.3 Hz, 3H), 7.72-7.6 (m, 5H), 7.55 (d, J = 7.3 Hz, 1H), 7.48 (d, J = 7.4 Hz, 2H), 5.08 (brs, 1H), 2.08 (s, 2H), 1.05 (s, 9H); LCMS (ESI+, m/z): 555.2 (M + H)⁺. |
| 7k (S) | thiophen-2-ylmethyl | ¹H NMR (400 MHz, DMSO-d₆): δ 10.34 (s, 1H), 8.88 (d, J = 7.3 Hz, 1H), 8.57 (d, J = 5.8 Hz, 1H), 8.23-8.19 (m, 2H), 7.92 (d, J = 7.4 Hz, 2H), 7.78 (s, 1H), 7.68-7.62 (m, 3H), 7.55-7.47 (m, 3H), 7.37 (d, J = 4.4 Hz, 1H), 7.08 (s, 1H), 6.98 (brs, 1H), 5.02 (brs, 1H), 3.60-3.30 (m, 2H), 1.05 (s, 9H); LCMS (ESI+, m/z): 536.2 (M + H)⁺. |

TABLE 2-continued 7a-n

[Structure shown at top of table]

| Compound No and chirality | R₁ | Analytical Data |
|---|---|---|
| 7l (S) | 2-methylbenzyl group | $^1$H NMR (400 MHz, DMSO-d$_6$): δ 10.17 (s, 1H), 8.84 (d, J = 7.2 Hz, 1H), 8.56 (d, J = 8.4 Hz, 1H), 8.18 (d, J = 7.2 Hz, 1H), 7.99 (d, J = 8.4 Hz, 1H), 7.93 (d, J = 7.2 Hz, 2H), 7.73 (s, 1H), 7.67 (t, J = 8.0 Hz, 1H), 7.59-7.53 (m, 3H), 7.49 (t, J = 7.2 Hz, 2H), 7.34 (d, J = 6.8 Hz, 1H), 7.21 (d, J = 6.8 Hz, 1H), 7.15-7.11 (m, 2H), 5.03 (q, J = 7.2 Hz, 1H), 3.30-3.21 (m, 2H), 2.42 (s, 3H), 1.04 (s, 9H); LCMS (ESI+, m/z): 544.2 (M + H)$^+$. |
| 7m (S) | 4-methylbenzyl group | $^1$H NMR (400 MHz, DMSO-d$_6$): δ 10.27 (s, 1H), 8.79 (d, J = 7.2 Hz, 1H), 8.56 (d, J = 7.6 Hz, 1H), 8.2 (d, J = 6.8 Hz, 1H), 8.13 (d, J = 8.0 Hz, 1H), 7.90 (d, J = 7.2 Hz, 2H), 7.78 (s, 1H), 7.69-7.59 (m, 3H), 7.54 (d, J = 6.8 Hz, 1H), 7.49 (t, J = 7.6 Hz, 2H), 7.34 (d, J = 8.0 Hz, 2H), 7.13 (d, J = 7.6 Hz, 2H), 4.99 (q, J = 6.4 Hz, 1H), 3.28-3.14 (m, 2H), 2.26 (s, 3H), 1.05 (s, 9H); LCMS (ESI+, m/z): 544.3 (M + H)$^+$. |
| 7n (S) | 4-chlorobenzyl group | $^1$H NMR (400 MHz, DMSO-d$_6$): δ 10.32 (s, 1H), 8.84 (d, J = 7.2 Hz, 1H), 8.57 (d, J = 8.4 Hz, 1H), 8.21 (d, J = 7.21 Hz, 1H), 8.16 (d, J = 8.8 Hz, 1H), 7.89 (d, J = 7.2 Hz, 2H), 7.78 (s, 1H), 7.70-7.62 (m, 3H), 7.56 (d, J = 7.6 Hz, 1H), 7.49 (d, J = 7.6 Hz, 4H), 7.39 (d, J = 8.4 Hz, 2H), 5.02 (q, J = 6 Hz, 1H), 3.39-3.18 (m, 2H), 1.05 (s, 9H); LCMS (ESI+, m/z): 564.2 (M + H)$^+$. |

Example-3

Synthesis of (S)—N-(1-((4-(N-(tert-butyl)sulfamoyl)phenyl)amino)-1-oxo-3-phenylpropan-2-yl)cyclohexanecarboxamide (10b)

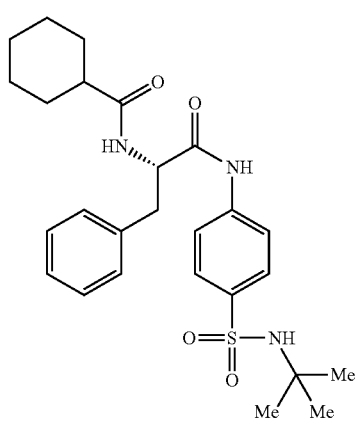 [SMILES: CC(C)(C)NS(=O)(=O)c1ccc(NC(=O)[C@H](Cc2ccccc2)NC(=O)C2CCCCC2)cc1]

Synthesis of 4-acetamidobenzenesulfonyl chloride (I)

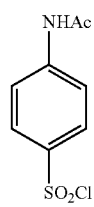

Chlorosulfuric acid (150 mL) was added to N-phenylacetamide (50 g, 370 mmol) at 0° C. and stirred at 60° C. for 4 h. After cooling to rt, water was added and the obtained solid was filtered, dried under vacuum to afford I (71.2 g, 82%) as a pale yellow solid: $^1$H NMR (400 MHz, DMSO-d$_6$): δ 10.04 (s, 1H), 7.53-7.48 (m, 4H), 2.03 (s, 3H); LCMS (ESI+, m/z): 231.9 (M–H)$^+$.

Synthesis of N-(4-(N-(tert-butyl)sulfamoyl)phenyl)acetamide (J)

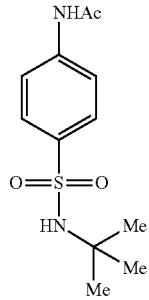 [SMILES: CC(=O)Nc1ccc(S(=O)(=O)NC(C)(C)C)cc1]

The above compound was synthesized according to general procedure-2 described in Example-1 as a pale yellow solid in 80% yield and was characterized by $^1$H NMR & LC-MS analysis. $^1$H NMR (400 MHz, DMSO-d$_6$): δ 10.35 (s, 1H), 7.92-7.73 (m, 5H), 2.07 (s, 3H), 1.06 (s, 9H); LCMS (ESI+, m/z): 269.1 (M–H)$^+$.

Synthesis of 4-amino-N-(tert-butyl)benzenesulfonamide (3ab)

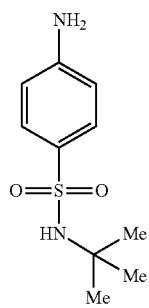 [SMILES: CC(C)(C)NS(=O)(=O)c1ccc(N)cc1]

The above compound was synthesized according to general procedure-3 described in Example-1 as a pale yellow solid in 70% yield and was characterized by $^1$H NMR analysis. $^1$H NMR (400 MHz, DMSO-d$_6$): δ7.42 (d, J=8.3 Hz, 2H), 6.99 (s, 1H), 6.57 (d, J=8.8 Hz, 2H), 5.84 (s, 2H), 1.05 (s, 9H).

Synthesis of (cyclohexanecarbonyl)-L-phenylalanine (3c)

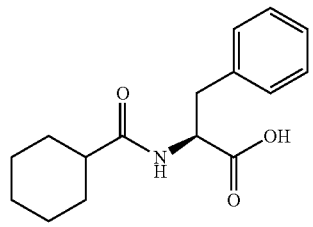 [SMILES: O=C(N[C@@H](Cc1ccccc1)C(=O)O)C1CCCCC1]

The above compound was synthesized in Scheme-5 described in Example-4 as off-white solid in 72% yield and was characterized by $^1$H NMR analysis.

Synthesis of (S)—N-(1-((4-(N-(tert-butyl)sulfamoyl)phenyl)amino)-1-oxo-3-phenylpropan-2-yl)cyclohexanecarboxamide (10b)

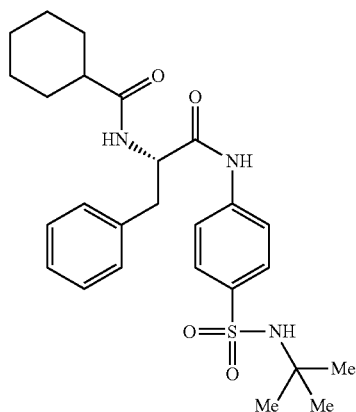 [SMILES: CC(C)(C)NS(=O)(=O)c1ccc(NC(=O)[C@H](Cc2ccccc2)NC(=O)C2CCCCC2)cc1]

The above compound was synthesized according to general procedure-5 described in Example-1 as a pale yellow solid in 12% yield and was characterized by $^1$H NMR & LC-MS analysis.

Synthesis of compounds 10a-j

Compounds 10a, 10c-g were synthesized following same procedure as described for compound 10b (Scheme-3a, Example-3)

Compounds 10h-j were synthesized following same procedure as described for compound 4n (Scheme-1c).

TABLE 3

10a-j

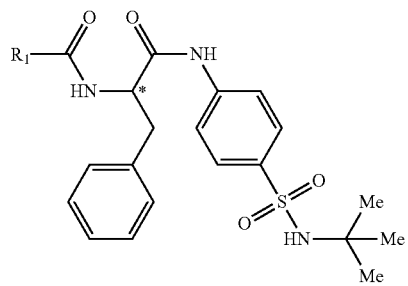

| Compound No and chirality | R$_1$ | Analytical Data |
|---|---|---|
| 10a (S) | 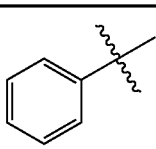 | $^1$H NMR (400 MHz, DMSO-d$_6$): δ 10.60 (s, 1H), 8.83 (d, J = 7.6 Hz, 1H), 7.84-7.78 (m, 6H), 7.55-7.43 (m, 6H), 7.29 (t, J = 7.4 Hz, 2H), 7.20-7.16 (m, 1H), 4.86-4.84 (m, 1H), 3.14-3.12 (m, 2H), 1.05 (s, 9H); LCMS (ESI+, m/z): 480.2 (M + H)$^+$. |

TABLE 3-continued 10a-j

[Structure: R₁-C(=O)-NH-CH(*)-C(=O)-NH-phenyl-SO₂-NH-C(Me)₃, with benzyl side chain on the chiral center]

| Compound No and chirality | R₁ | Analytical Data |
|---|---|---|
| 10b (S) | cyclohexyl-CH(Me)- | ¹H NMR (400 MHz, DMSO-d₆): δ 10.41 (s, 1H), 8.06 (d, J = 7.8 Hz, 1H), 7.73 (s, 4H), 7.37 (s, 1H), 7.28-7.22 (m, 4H), 7.18-7.16 (m, 1H), 4.65-4.61 (m, 1H), 3.04-2.99 (m, 1H), 2.88-2.82 (m, 1H), 2.18-2.15 (m, 1H), 1.66-1.47 (m, 5H), 1.24-1.06 (m, 14H); LCMS (ESI+, m/z): 486.2 (M + H)+. |
| 10c (S) | cyclopentyl-CH(Me)- | ¹H NMR (400 MHz, DMSO-d₆): δ 10.43 (s, 1H), 8.15 (d, J = 8.3 Hz, 1H), 7.74 (t, J = 9.5 Hz, 4H), 7.39 (s, 1H), 7.30-7.16 (m, 5H), 4.67 (q, J = 4.9 Hz, 1H), 3.04 (dd, J = 13.2 & 4.9 Hz, 1H), 2.87 (t, J = 11.7 Hz, 1H), 2.43-2.32 (m, 1H), 1.69-1.41 (m, 8H), 1.08 (s, 9H); LCMS (ESI+, m/z): 472.3 (M + H)⁺. |
| 10d (R) | cyclohexyl-CH(Me)- | ¹H NMR (400 MHz, DMSO-d₆): δ 10.45 (s, 1H), 8.11 (d, J = 8.4 Hz, 1H), 7.75 (s, 4H), 7.41 (s, 1H), 7.28-7.24 (m, 4H) 7.19-7.18 (m, 1H), 4.65-4.60 (m, 1H), 3.05-3.01 (m, 1H), 2.89-2.83 (m, 1H), 2.15-2.14 (m, 1H), 1.64-1.49 (m, 5H), 1.26-1.13 (m, 5H), 1.07 (s, 9H); LCMS (ESI+, m/z): 486.3 (M + H)⁺. |
| 10e (S) | 4-F-C₆H₄-CH(Me)- | ¹H NMR (400 MHz, DMSO-d₆): δ 10.57 (s, 1H), 8.86 (d, J = 8.0 Hz, 1H), 7.91 (t, J = 5.6 Hz, 2H), 7.77 (s, 4H), 7.41-7.39 (m, 3H), 7.31-7.27 (m, 4H), 7.20-7.16 (m, 1H), 4.84-4.81 (m, 1H), 3.30-3.06 (m, 2H), 1.08 (s, 9H); LCMS (ESI+, m/z): 498.2 (M + H)⁺. |
| 10f (S) | 4-HOOC-C₆H₄-CH(Me)- | ¹H NMR (400 MHz, DMSO-d₆): δ 13.23 (brs, 1H), 10.66 (s, 1H), 9.05 (d, J = 7.6 Hz, 1H), 8.00-7.91 (m, 4H), 7.78 (s, 4H), 7.43-7.41 (m, 3H), 7.30-7.28 (m, 2H), 7.20-7.17 (m, 1H), 4.92-4.82 (m, 1H), 3.19-3.08 (m, 2H), 1.08 (s, 9 H); LCMS (ESI+, m/z): 524.2 (M + H)⁺. |
| 10g (S) | 4-MeOOC-C₆H₄-CH(Me)- | ¹H NMR (400 MHz, DMSO-d₆): δ 10.63 (s, 1H), 9.09 (d, J = 8.0 Hz, 1H), 8.04-7.94 (m, 4H), 7.78 (s, 4H), 7.43-7.26 (m, 6H), 4.93-4.82 (m, 1H), 3.88 (s, 3H), 3.19-3.09 (m, 2H), 1.078 (s, 9 H); LCMS (ESI+, m/z): 538.2 (M + H)⁺. |
| 10h (S) | 2-pyridyl-CH(Me)- | ¹H NMR (400 MHz, DMSO-d₆): δ 10.61 (s, 1H), 8.80 (d, J = 8.4 Hz, 1H), 8.67 (d, J = 4.8 Hz, 1H), 8.00-7.99 (m, 2H), 7.79-7.79 (m, 4H), 7.64-7.61 (m, 1H), 7.43 (s, 1H), 7.30-7.23 (m, 4H), 7.19-7.17 (m, 1H), 4.97-4.94 (m, 1H), 3.23-3.19 (m, 2H), 1.08 (s, 9 H); LCMS (ESI+, m/z): 481.2 (M + H)⁺. |
| 10i (S) | pyrrolidin-2-yl-CH(Me)- | ¹H NMR (400 MHz, DMSO-d₆): δ 10.55 (s, 1H), 7.91 (d, J = 8.8 Hz, 1H), 7.78-7.72 (m, 4H), 7.40 (s, 1H), 7.29-7.21 (m, 5H), 4.82-4.76 (m, 1H), 3.29 (s, 1H), 3.15-3.09 (m, 2H), 3.02-2.89 (m, 3H), 2.32-2.21 (m, 1H), 1.87-1.83 (m, 1H), 1.53-1.43 (m, 2H), 1.08 (s, 9H); LCMS (ESI+, m/z): 473.2 (M + H)⁺. |

TABLE 3-continued

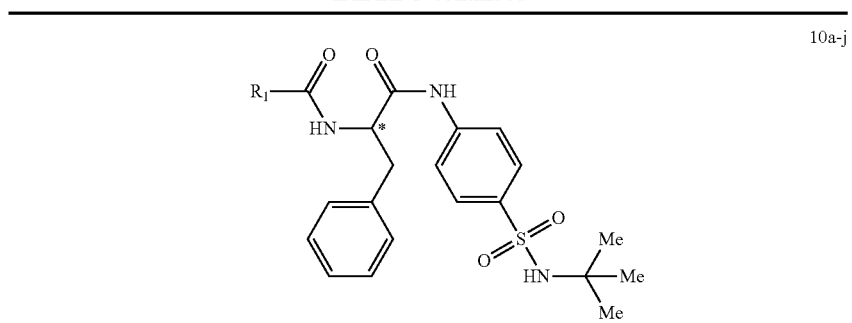

10a-j

| Compound No and chirality | R₁ | Analytical Data |
|---|---|---|
| 10j (S) | 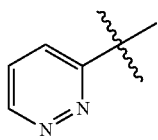 [SMILES: *c1cccnn1] | ¹H NMR (400 MHz, DMSO-d₆): δ 10.55 (s, 1H), 9.42 (d, J = 3.6 Hz, 1H), 9.26 (d, J = 8.0 Hz, 1H), 8.14 (d, J = 8.4 Hz, 1H), 7.92-7.89 (m, 1H), 7.79 (s, 4H), 7.40 (s, 1H), 7.34-7.32 (m, 2H), 7.27-7.23 (m, 2H), 7.19-7.16 (m, 1H), 5.02-4.96 (m, 1H), 3.25 (d, J = 6.8 Hz, 2H), 1.08 (s, 9H); LCMS (ESI+, m/z): 482.0 (M + H)⁺. |

Synthesis of compound 14a-j

Compounds 14a-d were synthesized following same procedure as described for compound 4b (Scheme-1b)

Compounds 14e-j were synthesized following same procedure as described for compound 4n (Scheme-1c).

TABLE 4

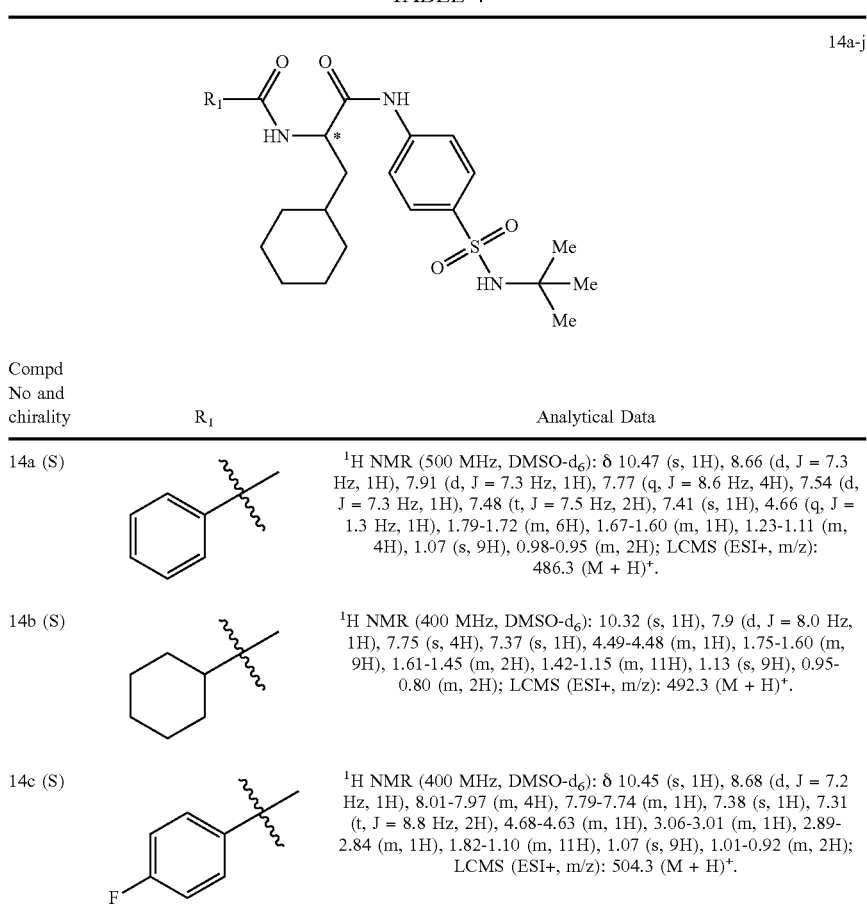

14a-j

| Compd No and chirality | R₁ | Analytical Data |
|---|---|---|
| 14a (S) | 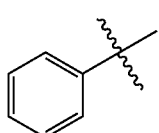 | ¹H NMR (500 MHz, DMSO-d₆): δ 10.47 (s, 1H), 8.66 (d, J = 7.3 Hz, 1H), 7.91 (d, J = 7.3 Hz, 1H), 7.77 (q, J = 8.6 Hz, 4H), 7.54 (d, J = 7.3 Hz, 1H), 7.48 (t, J = 7.5 Hz, 2H), 7.41 (s, 1H), 4.66 (q, J = 1.3 Hz, 1H), 1.79-1.72 (m, 6H), 1.67-1.60 (m, 1H), 1.23-1.11 (m, 4H), 1.07 (s, 9H), 0.98-0.95 (m, 2H); LCMS (ESI+, m/z): 486.3 (M + H)⁺. |
| 14b (S) | 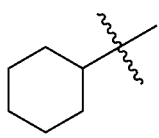 [SMILES: *C1CCCCC1] | ¹H NMR (400 MHz, DMSO-d₆): 10.32 (s, 1H), 7.9 (d, J = 8.0 Hz, 1H), 7.75 (s, 4H), 7.37 (s, 1H), 4.49-4.48 (m, 1H), 1.75-1.60 (m, 9H), 1.61-1.45 (m, 2H), 1.42-1.15 (m, 11H), 1.13 (s, 9H), 0.95-0.80 (m, 2H); LCMS (ESI+, m/z): 492.3 (M + H)⁺. |
| 14c (S) | 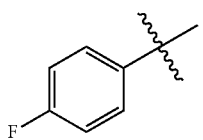 [SMILES: *c1ccc(F)cc1] | ¹H NMR (400 MHz, DMSO-d₆): δ 10.45 (s, 1H), 8.68 (d, J = 7.2 Hz, 1H), 8.01-7.97 (m, 4H), 7.79-7.74 (m, 1H), 7.38 (s, 1H), 7.31 (t, J = 8.8 Hz, 2H), 4.68-4.63 (m, 1H), 3.06-3.01 (m, 1H), 2.89-2.84 (m, 1H), 1.82-1.10 (m, 11H), 1.07 (s, 9H), 1.01-0.92 (m, 2H); LCMS (ESI+, m/z): 504.3 (M + H)⁺. |

TABLE 4-continued 14a-j

| Compd No and chirality | R₁ | Analytical Data |
|---|---|---|
| 14d (S) | 4-(trifluoromethyl)phenyl | ¹H NMR (400 MHz, DMSO-d₆): δ 10.49 (s, 1H), 8.93 (d, J = 7.4 Hz, 1H), 8.09 (d, J = 8.3 Hz, 2H), 7.85 (d, J = 8.4 Hz, 2H), 7.78-7.72 (m, 4H), 7.39 (s, 1H), 4.64 (m, 1 H), 1.77-1.58 (m, 7H), 1.16-1.06 (m, 6H), 1.05 (s, 9H); LCMS (ESI+, m/z): 554.2 (M + H)⁺. |
| 14e (S) | cyclopentylmethyl | ¹H NMR (400 MHz, DMSO-d₆): δ 10.35 (s, 1H), 8.02 (d, J = 8.0 Hz, 1H), 7.78-7.72 (m, 4H), 7.39 (s, 1H), 4.50-4.45 (m, 1H), 2.68-2.63 (m, 1H), 1.77-1.34 (m, 15H), 1.29-1.08 (m, 13H), 1.05 (m, 2 H); LCMS (ESI+, m/z): 478.3 (M + H)⁺. |
| 14f (S) | 2-fluorophenyl | ¹H NMR (400 MHz, DMSO-d₆): δ 10.44 (s, 1H), 8.56 (brs, 1H), 7.81-7.72 (m, 4H), 7.60-7.20 (m, 5H), 4.71-4.60 (m, 1H), 1.77-1.45 (m, 9H), 1.20-1.10 (m, 4H), 1.08 (s, 9H); LCMS (ESI+, m/z): 504.2 (M + H)⁺. |
| 14g (S) | 3-fluorophenyl | ¹H NMR (400 MHz, DMSO-d₆): δ 10.49 (s, 1H), 8.77 (d, J = 7.6 Hz, 1H), 7.79-7.72 (m, 6H), 7.57-7.52 (m, 1H), 7.51-7.41 (m, 2H), 4.70-4.60 (m, 1H), 1.78-1.61 (m, 7H), 1.50-1.39 (m, 1H), 1.17-1.14 (m, 2H), 1.07 (s, 9 H), 1.03-0.90 (m, 3H); LCMS (ESI+, m/z): 504.3 (M + H)⁺. |
| 14h (S) | 3,4-difluorophenyl | ¹H NMR (400 MHz, DMSO-d₆): δ 10.46 (s, 1H), 8.76 (d, J = 7.2 Hz, 1H), 8.01-7.96 (m, 1H), 7.81-7.74 (m, 5H), 7.60-7.53 (m, 1H), 7.38 (s, 1H), 4.68-4.63 (m, 1H), 1.81-1.60 (m, 7H), 1.52-1.39 (m, 1H), 1.29-1.13 (m, 3H), 1.08 (s, 9 H), 1.01-0.95 (m, 2H); LCMS (ESI+, m/z): 522.2 (M + H)⁺. |
| 14i (S) | 3-cyanophenyl | ¹H NMR (400 MHz, DMSO-d₆): δ 10.45 (s, 1H), 8.85 (d, J = 8.0 Hz, 1H), 8.36 (s, 1H), 8.19 (d, 1H, J = 7.6 Hz), 8.01 (d, J = 7.2 Hz, 1H), 7.57-7.67 (m, 5H), 7.37 (s, 1H), 4.70-4.62 (m, 1H), 1.80-1.60 (m, 5H), 1.45-1.38 (m, 5H), 1.22-1.15 (m, 3H), 1.06 (s, 9H); LCMS (ESI+, m/z): 509.2 (M − H)⁺. |
| 14j (S) | pyridin-2-yl | ¹H NMR (400 MHz, DMSO-d₆): δ 10.50 (s, 1H), 8.73-8.69 (m, 2H), 8.06-8.00 (m, 2H), 7.76 (s, 4H), 7.66-7.63 (m, 1H), 7.39 (s, 1H), 4.80-4.76 (m, 1H), 1.84-1.58 (m, 7H), 1.49-1.40 (m, 1H), 1.16-1.11 (m, 3H), 1.07 (s, 9H), 0.97-0.94 (m, 2H); LCMS (ESI+, m/z): 487.3 (M + H)⁺. |

Synthesis of compounds 19a-z and 19aa-ae
Compounds 19a-q were synthesized following same procedure as described for compound 4b (Scheme-1b)

Compounds 19s-z and 19aa-ae were synthesized following same procedure as described for compound 4n (Scheme-1).

TABLE 5

[Structure: R₂-C(=O)-NH-C*H(R₁)-C(=O)-NH-R₃]

19a-z, 19aa-ae

| Compd No and chirality | R₁ | R₂ | R₃ | Analytical Data |
|---|---|---|---|---|
| 19a (S) | 2-thienylmethyl | cyclohexyl | 4-(2-(tert-butylsulfonamido)propan-2-yl)phenyl | $^1$H NMR (400 MHz, DMSO-$d_6$): δ 10.46 (s, 1H), 8.13 (d, J = 7.8 Hz, 1H), 7.77-7.73 (m, 4H), 7.39 (s, 1H), 7.32 (t, J = 3.2 Hz, 1H), 6.94-6.92 (m, 2H), 4.67-4.61 (m, 1H), 3.29-3.24 (m, 1H), 3.17-3.11 (m, 1H), 2.23-2.17 (m, 1H), 1.67-1.58 (m, 5H), 1.33-1.13 (m, 5H), 1.08 (s, 9H); LCMS (ESI+, m/z): 492.2 (M + H)⁺. |
| 19b (S) | 4-fluorobenzyl | phenyl | 4-(2-methylsulfonamido-propan-2-yl)phenyl | $^1$H NMR (400 MHz, DMSO-$d_6$): δ 10.61 (s, 1H), 8.85 (d, J = 7.6 Hz, 1H), 7.84-7.77 (m, 5H), 7.56-7.44 (m, 6H), 7.12 (t, J = 8.8 Hz, 2H), 4.85-4.79 (m, 1H), 3.18-3.06 (m, 2H), 1.08 (s, 9 H); LCMS (ESI+, m/z): 498.2 (M + H)⁺. |
| 19c (S) | cyclopropylmethyl | cyclohexyl | 4-(2-sulfonamido-propan-2-yl)phenyl | $^1$H NMR (400 MHz, DMSO-$d_6$): δ 10.35 (s, 1H), 7.98 (d, J = 8.0 Hz, 1H), 7.74 (s, 4H), 7.37 (s, 1H), 4.48-4.42 (m, 1H), 2.24 (t, J = 11.2 Hz, 1H), 1.70-1.60 (m, 6H), 1.47-1.41 (m, 1H), 1.39-1.12 (m, 5H), 1.08 (s, 9 H), 0.76-0.75 (m, 1H), 0.41-0.32 (m, 4H); LCMS (ESI+, m/z): 450.3 (M + H)⁺. |
| 19d (S) | benzyl | cyclohexyl | 3-methyl-4-(2-sulfonamido-propan-2-yl)phenyl | $^1$H NMR (400 MHz, DMSO-$d_6$): δ 10.37 (s, 1H), 8.11 (d, J = 8.4 Hz, 1H), 7.80 (d, J = 8.8 Hz, 1H), 7.58-7.56 (m, 2H), 7.39 (s, 1H), 7.30-7.24 (m, 4H), 7.20-7.18 (m, 1H), 4.70-4.60 (m, 1H), 3.14-2.94 (m, 1H), 2.89-2.80 (m, 1H), 2.54 (s, 3H), 2.19-2.10 (m, 1H), 1.72-1.58 (m, 4H), 1.52-1.40 (m, 1H), 1.22-1.12 (m, 5H), 1.08 (s, 9 H); LCMS (ESI+, m/z): 500.3 (M + H)⁺. |
| 19e (S) | 3-chlorobenzyl | cyclohexyl | 4-(2-sulfonamido-propan-2-yl)phenyl | $^1$H NMR (400 MHz, DMSO-$d_6$): δ 10.49 (s, 1H), 8.16 (d, J = 8.4 Hz, 1H), 7.78-7.73 (m, 4H), 7.38 (s, 2H), 7.33 (s, 3H), 4.67-4.61 (m, 1H), 3.06-3.02 (m, 1H), 2.85-2.80 (m, 1H), 2.17-1.99 (m, 1H), 1.67-1.49 (m, 5H), 1.26-1.12 (m, 5H), 1.08 (s, 9 H); LCMS (ESI+, m/z): 520.2 (M + H)⁺. |

TABLE 5-continued

| Compd No and chirality | R₁ | R₂ | R₃ | Analytical Data |
|---|---|---|---|---|
| 19f (S) | 4-methoxybenzyl | 4-fluorophenyl | 4-(N-tert-butylsulfamoyl)phenyl | ¹H NMR (400 MHz, DMSO-d₆): δ 10.59 (s, 1H), 8.85 (d, J = 8.0 Hz, 1H), 7.93-7.89 (m, 2H), 7.77 (s, 4H), 7.42 (s, 1H), 7.34-7.29 (m, 4H), 6.85 (d, J = 8.8 Hz, 2H), 4.81-4.72 (m, 1H), 3.69 (s, 3H), 3.07-3.03 (m, 2H), 1.08 (s, 9 H); LCMS (ESI+, m/z): 528.3 (M + H)⁺. |
| 19g (S) | 2-thienylmethyl | 4-fluorophenyl | 4-(N-tert-butylsulfamoyl)phenyl | ¹H NMR (400 MHz, DMSO-d₆): δ 10.64 (s, 1H), 8.95 (d, J = 7.6 Hz, 1H), 7.97-7.94 (m, 2H), 7.78 (s, 4H), 7.43 (s, 1H), 7.34-7.30 (m, 3H), 7.03-7.02 (m, 1H), 6.95-6.93 (m, 1H), 4.84-4.81 (m, 1H), 3.39-3.37 (m, 2H), 1.08 (s, 9 H); LCMS (ESI+, m/z): 504.2 (M + H)⁺. |
| 19h (S) | benzyl | cyclohexyl | 4-(N-tert-butylsulfamoyl)phenyl | ¹H NMR (400 MHz, DMSO-d₆): δ 10.44 (s, 1H), 8.08 (d, J = 7.6 Hz, 1H), 7.75 (s, 4H), 7.44-7.43 (m, 1H), 7.28-7.18 (m, 5H), 4.69-4.61 (m, 1H), 3.21-3.19 (m, 1H), 3.04-3.02 (m, 1H), 2.89-2.87 (m, 1H), 2.19-2.10 (m, 1H), 1.64-1.50 (m, 5H), 1.28-1.16 (m, 5H), 0.93 (d, J = 6.0 Hz, 6H); LCMS (ESI+, m/z): 472.2 (M + H)⁺. |
| 19i (S) | (R)-1-hydroxyethyl | cyclohexyl | 4-(N-tert-butylsulfamoyl)phenyl | ¹H NMR (400 MHz, CDCl₃): δ 9.34 (s, 0.55H), 9.25 (s, 0.45 H), 7.83-7.81 (m, 2H), 7.61-7.60 (m, 2H), 6.66-6.60 (m, 1H), 4.52-4.42 (m, 2.6H), 3.99 (m, 0.5H), 3.76 (m, 0.45H), 3.44 (brs, 0.58H), 2.29-2.19 (m, 1H), 1.91-1.57 (m, 5H), 1.48-1.22 (m, 16H), ; LCMS (ESI+, m/z): 440.3 (M + H)⁺. |
| 19j (S) | hydroxymethyl | cyclohexyl | 4-(N-tert-butylsulfamoyl)phenyl | ¹H NMR (400 MHz, DMSO-d₆): δ 10.30 (s, 1H), 7.82-7.73 (m, 5H), 7.37 (s, 1H), 5.10 (brs, 1H), 4.45-4.40 (m, 1H), 3.63 (d, J = 5.2 Hz, 2H), 2.27-2.22 (m, 1H), 1.71-1.60 (m, 5H), 1.63-1.15 (m, 5H), 1.07 (s, 9H); LCMS (ESI+, m/z): 426.2 (M + H)⁺. |

TABLE 5-continued

| Compd No and chiralityl | R₁ | R₂ | R₃ | Analytical Data |
|---|---|---|---|---|
| 19k (S) | 4-fluorobenzyl | 4-fluorophenyl | 4-(N-tert-butylsulfamoyl)phenyl | ¹H NMR (400 MHz, DMSO-d₆): δ 10.56 (s, 1H), 8.85 (d, J = 7.6 Hz, 1H), 7.92-7.88 (m, 2H), 7.77 (s, 4H), 7.45-7.39 (m, 3H), 7.32-7.27 (m, 2H), 7.13-7.09 (m, 2H), 4.85-4.79 (m, 1H), 3.14-3.09 (m, 2H), 1.08 (s, 9H); LCMS (ESI+, m/z): 516.0 (M + H)⁺. |
| 19l (S) | 4-biphenylmethyl | 4-fluorophenyl | 4-(N-tert-butylsulfamoyl)phenyl | ¹H NMR (400 MHz, DMSO-d₆): δ 10.60 (s, 1H), 8.90 (d, J = 7.6 Hz, 1H), 7.95-7.91 (m, 2H), 7.78-7.76 (m, 4H), 7.64-7.59 (m, 4H), 7.51-7.49 (m, 2H), 7.45-7.39 (m, 3H), 7.35-7.28 (m, 3H), 4.89-4.85 (m, 1H), 3.21-3.12 (m, 2H), 1.08 (s, 9H); LCMS (ESI+, m/z): 574.0 (M + H)⁺. |
| 19m (S) | benzyl | cyclohexyl | 2-fluoro-4-(N-tert-butylsulfamoyl)phenyl | LCMS (ESI⁻, m/z): 502.1 (M − H). |
| 19n (S) | (pyridin-3-yl)methyl | 4-fluorophenyl | 4-(N-tert-butylsulfamoyl)phenyl | ¹H NMR (400 MHz, DMSO-d₆): δ 10.63 (s, 1H), 8.95 (d, J = 8.0 Hz, 1H), 8.60 (brs, 1H), 8.43-8.37 (m, 1H), 7.92-7.88 (m, 2H), 7.80 (s, 4H), 7.44 (s, 1H), 7.33-7.28 (m, 3H), 4.88-4.82 (m, 1H), 1.08 (s, 9H). LCMS (ESI+, m/z): 499.0 (M + H)⁺. |
| 19o (S) | (pyridin-2-yl)methyl | 4-fluorophenyl | 4-(N-tert-butylsulfamoyl)phenyl | ¹H NMR (400 MHz, DMSO-d₆): δ 10.55 (s, 1H), 8.87 (d, J = 8.0 Hz, 1H), 8.55 (d, J = 4.4 Hz, 1H), 7.90-7.86 (m, 2H), 7.79-7.73 (m, 5H), 7.45 (d, J = 7.6 Hz, 1H), 7.38 (s, 1H), 7.29 (t, J = 8.8 Hz, 3H), 5.07-5.05 (m, 1H), 3.45-3.26 (m, 2H), 1.07 (s, 9H); LCMS (ESI+, m/z): 499.0 (M + H)⁺. |

TABLE 5-continued

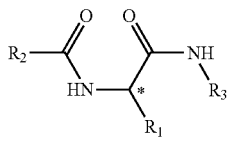

19a-z, 19aa-ae

| Compd No and chiralityl | R₁ | R₂ | R₃ | Analytical Data |
|---|---|---|---|---|
| 19p (S) | cyclohexylmethyl | cyclohexyl | 4-(N-tert-butylsulfamoyl)naphthalen-1-yl | $^1$H NMR (400 MHz, DMSO-$d_6$): δ 10.10 (s, 1H), 8.56 (d, J = 7.8 Hz, 1H), 8.24 (d, J = 8.8 Hz, 1H), 8.20 (d, J = 7.3 Hz, 1H), 8.01 (d, J = 6.8 Hz, 1H), 7.78 (s, 1H), 7.69-7.63 (m, 3H), 4.60 (q, J = 7.4 Hz, 1H), 2.44-2.24 (m, 1H), 1.71-1.63 (m, 10H), 1.41-1.33 (m, 3H), 1.24-1.15 (m, 8H), 1.05 (s, 9H), 0.99-0.85 (m, 2H); LCMS (ESI+, m/z): 542.3 (M + H)⁺. |
| 19q (S) | benzyl | styryl | 4-(N-tert-butylsulfamoyl)naphthalen-1-yl | $^1$H NMR (400 MHz, DMSO-$d_6$): δ 10.27 (s, 1H), 8.61 (d, J = 7.6 Hz, 1H), 8.56 (d, J = 8.0 Hz, 1H), 8.19 (d, J = 7.6 Hz, 1H), 8.00 (d, J = 8.0 Hz, 1H), 7.78 (s, 1H), 7.66 (t, J = 8.0 Hz, 1H), 7.60-7.56 (m, 4H), 7.44-7.38 (m, 6H), 7.31 (t, J = 7.2 Hz, 2H), 7.27-7.25 (m, 1H), 6.79 (d, J = 16 Hz, 1H), 5.02-5.00 (m, 1H), 3.20-3.18 (m, 1H), 3.10-3.08 (m, 1H), 1.05 (s, 9H); LCMS (ESI+, m/z): 556.2 (M + H)⁺. |
| 19s (S) | thiophen-2-ylmethyl | pyridin-2-yl | 4-(N-tert-butylsulfamoyl)phenyl | $^1$H NMR (400 MHz, DMSO-$d_6$): δ 10.62 (s, 1H), 8.88 (d, J = 8.4 Hz, 1H), 8.69 (d, J = 4.4 Hz, 1H), 8.04-7.99 (m, 2H), 7.79-7.73 (m, 4H), 7.65-7.62 (m, 1H), 7.40 (s, 1H), 7.32 (t, J = 3.6 Hz, 1H), 6.91 (d, J = 3.2 Hz, 2H), 4.97-4.92 (m, 1H), 3.48-3.46 (m, 2H), 1.08 (s, 9H); LCMS (ESI+, m/z): 487.2 (M + H)⁺. |
| 19t (S) | thiophen-2-ylmethyl | 5-methoxypyridin-2-yl | 4-(N-tert-butylsulfamoyl)phenyl | $^1$H NMR (400 MHz, DMSO-$d_6$): δ 10.61 (s, 1H), 8.67 (d, J = 7.6 Hz, 1H), 8.36 (d, J = 3.2 Hz, 1H), 7.99 (d, J = 8.8 Hz, 1H), 7.79-7.73 (m, 4H), 7.56-7.53 (m, 1H), 7.40 (s, 1H), 7.32 (d, J = 4.4 Hz, 1H), 6.92-6.90 (m, 2H), 4.94-4.90 (m, 1H), 3.90 (s, 3H), 3.50-3.46 (m, 2H), 1.08 (s, 9H); LCMS (ESI+, m/z): 517.2 (M + H)⁺. |
| 19u (S) | 4-methoxybenzyl | pyridin-2-yl | 4-(N-tert-butylsulfamoyl)phenyl | $^1$H NMR (400 MHz, DMSO-$d_6$): δ 10.58 (s, 1H), 8.75-8.67 (m, 2H), 8.0-7.99 (m, 2H), 7.78-7.33 (m, 4H), 7.63-7.62 (m, 1H), 7.40 (s, 1H), 7.18 (d, J = 8.4 Hz, 2H), 6.81 (d, 2H, J = 8.0 Hz), 4.91-4.88 (m, 1H), 3.68 (s, 3H), 3.14-3.12 (m, 2H), 1.08 (s, 9H); LCMS (ESI+, m/z): 511.2 (M + H)⁺. |

TABLE 5-continued

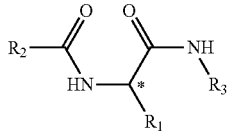

19a-z, 19aa-ae

| Compd No and chirality | R₁ | R₂ | R₃ | Analytical Data |
|---|---|---|---|---|
| 19v (S) | 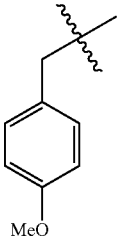 [SMILES: *Cc1ccc(OC)cc1] | 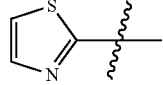 | 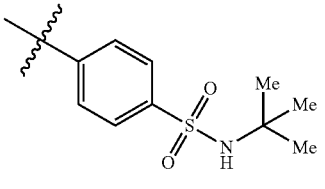 [SMILES: *c1ccc(S(=O)(=O)NC(C)(C)C)cc1] | ¹H NMR (400 MHz, DMSO-d₆): δ 10.54 (s, 1H), 8.77 (d, J = 8.4 Hz, 1H), 8.04 (s, 2H), 7.76-7.75 (m, 4H), 7.40 (s, 1H), 7.23 (d, J = 8.4 Hz, 2H), 6.82 (d, J = 8.4 Hz, 2H), 4.83-4.81 (m, 1H), 3.68 (s, 3H), 3.19-3.10 (m, 2H), 1.08 (s, 9H); LCMS (ESI+, m/z): 517.2 (M + H)⁺. |
| 19w (S) | 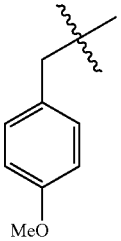 [SMILES: *Cc1ccc(OC)cc1] | 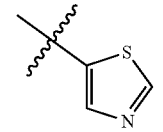 | 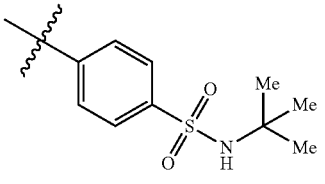 [SMILES: *c1ccc(S(=O)(=O)NC(C)(C)C)cc1] | ¹H NMR (400 MHz, DMSO-d₆): δ 10.58 (s, 1H), 9.22 (s, 1H), 9.08 (d, J = 7.8 Hz, 1H), 8.58 (s, 1H), 7.76 (s, 4H), 7.39 (s, 1H), 7.30 (d, J = 8.3 Hz, 2H), 6.84 (d, J = 8.8 Hz, 2H), 4.82-4.70 (m, 1H), 3.68 (s, 3H), 3.08-2.99 (m, 2H), 1.09 (s, 9H); LCMS (ESI+, m/z): 516.9 (M + H)⁺. |
| 19x (S) | 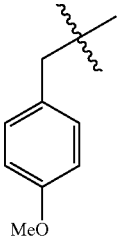 [SMILES: *Cc1ccc(OC)cc1] | 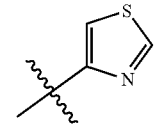 [SMILES: *c1cscn1] | 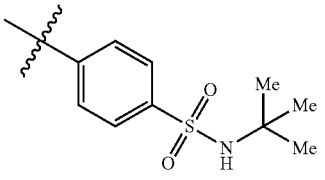 [SMILES: *c1ccc(S(=O)(=O)NC(C)(C)C)cc1] | ¹H NMR (400 MHz, DMSO-d₆): δ 10.55 (s, 1H), 9.19 (d, J = 1.6 Hz, 1H), 8.36 (d, J = 8.4 Hz, 1H), 8.32 (d, J = 2.0 Hz, 1H), 7.79-7.73 (m, 4H), 7.39 (s, 1H), 7.20 (d, J = 8.4 Hz, 2H), 6.82 (d, J = 8.8 Hz, 2H), 4.87-4.85 (m, 1H), 3.69 (s, 3H), 3.12-3.10 (m, 2H), 1.08 (s, 9 H); LCMS (ESI+, m/z): 517.0 (M + H)⁺. |
| 19y (S) | 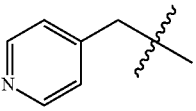 | 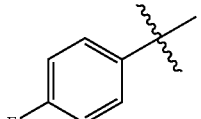 | 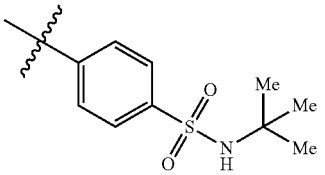 [SMILES: *c1ccc(S(=O)(=O)NC(C)(C)C)cc1] | ¹H NMR (400 MHz, DMSO-d₆): δ 10.60 (s, 1H), 8.91 (d, J = 7.6 Hz, 1H), 8.47 (d, J = 6.0 Hz, 2H), 7.91-7.88 (m, 2H), 7.77 (s, 4H), 7.40-7.38 (m, 3H), 7.30 (t, J = 8.8 Hz, 2H), 4.93-4.88 (m, 1H), 3.39-3.12 (m, 2H), 1.08 (s, 9H); LCMS (ESI+, m/z): 499.0 (M + H)⁺. |
| 19z (S) | 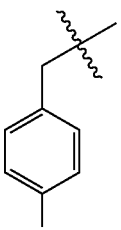 | 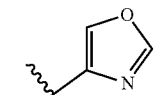 | 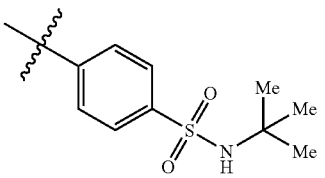 [SMILES: *c1ccc(S(=O)(=O)NC(C)(C)C)cc1] | ¹H NMR (400 MHz, DMSO-d₆): δ 10.53 (s, 1H), 8.63 (s, 1H), 8.52 (s, 1H), 8.20 (d, J = 8.0 Hz, 1H), 7.78-7.73 (m, 4H), 7.40 (s, 1H), 7.20 (d, J = 8.8 Hz, 2H), 6.82 (d, J = 8.8 Hz, 2H), 4.83-4.81 (m, 1H), 3.69 (s, 3H), 3.09-3.07 (m, 2H), 1.08 (s, 9H); LCMS (ESI+, m/z): 501.0 (M + H)⁺. |

TABLE 5-continued

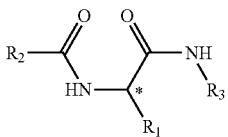

19a-z, 19aa-ae

| Compd No and chiralityl | R₁ | R₂ | R₃ | Analytical Data |
|---|---|---|---|---|
| 19aa (S) | 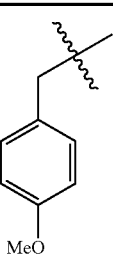 | 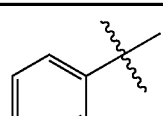 | 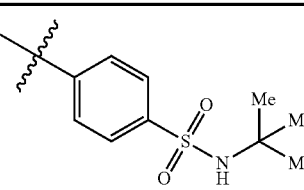 | $^1$H NMR (400 MHz, DMSO-d₆): δ 10.62 (s, 1H), 9.06 (d, J = 7.6 Hz, 1H), 8.96 (s, 1H), 8.72-8.70 (m, 1H), 7.78 (s, 4H), 7.52-7.49 (m, 1H), 7.43 (s, 1H), 7.33 (d, J = 8.8 Hz, 2H), 6.85 (d, J = 8.8 Hz, 2H), 4.83-4.78 (m, 1H), 3.69 (s, 3H), 3.13-2.99 (m, 2H), 1.08 (s, 9H); LCMS (ESI+, m/z): 511.0 (M + H)⁺. |
| 19ab (S) | 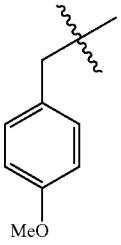 [SMILES: *Cc1ccc(OC)cc1] | 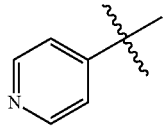 [SMILES: *c1ccncc1] | 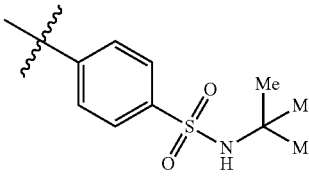 | $^1$H NMR (400 MHz, DMSO-d₆): δ 10.63 (s, 1H), 9.16 (d, J = 8.0 Hz, 1H), 8.74 (d, J = 5.6 Hz, 2H), 7.78-7.74 (m, 5H), 7.44 (s, 1H), 7.32 (d, J = 8.4 Hz, 1H), 7.11-7.08 (m, 2H), 6.85 (d, J = 8.8 Hz, 2H), 4.86-4.79 (m, 1H), 3.69 (s, 3H), 3.12-3.02 (m, 2H), 1.08 (s, 9H); LCMS (ESI+, m/z): 511.0 (M + H)⁺. |
| 19ac (S) | 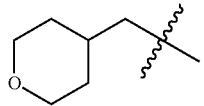 [SMILES: *CC1CCOCC1] | 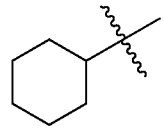 | 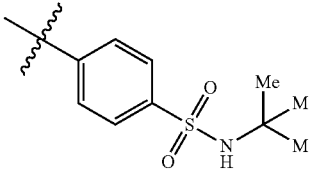 | $^1$H NMR (400 MHz, DMSO-d₆): δ 10.37 (s, 1H), 8.03 (d, J = 8.0 Hz, 1H), 7.73 (s, 4H), 7.40 (s, 1H), 4.47-4.42 (m, 1H), 3.81-3.37 (m, 3H), 1.68-1.63 (m, 8H), 1.33-1.11 (m, 10H), 1.07 (s, 9H); ); LCMS (ESI+, m/z): 494.1 (M + H)⁺. |
| 19ad (S) | 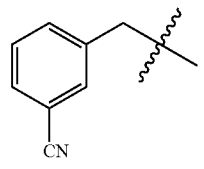 [SMILES: *Cc1cccc(C#N)c1] | 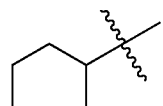 | 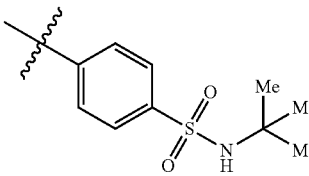 | $^1$H NMR (400 MHz, DMSO-d₆): δ 10.43 (s, 1H), 8.14 (d, J = 8.0 Hz, 1H), 7.78-7.74 (m, 5H), 7.71-7.62 (m, 2H), 7.50 (t, J = 7.6 Hz, 1H), 7.40 (s, 1H), 4.70-4.64 (m, 1H), 3.13-2.95 (m, 1H), 2.92-2.88 (m, 1H), 2.17-2.12 (m, 1H), 1.63-1.56 (m, 5H), 1.30-1.23 (m, 5H), 1.08 (s, 9 H); LCMS (ESI+, m/z): 511.3 (M + H)⁺. |
| 19ae (S) | 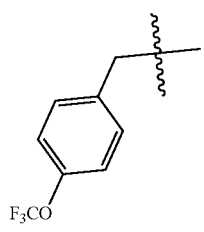 | 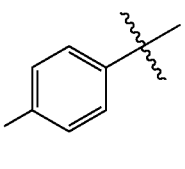 | 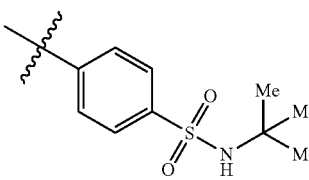 | $^1$H NMR (400 MHz, DMSO-d₆): δ 10.56 (s, 1H), 8.88 (d, J = 8.0 Hz, 1H), 7.92-7.88 (m, 2H), 7.79 (s, 4H), 7.51 (d, J = 8.8 Hz, 2H), 7.32-7.27 (m, 4H), 4.87-4.82 (m, 1H), 3.22-3.10 (m, 2H), 1.37 (s, 1H), 1.08 (s, 9H); LCMS (ESI+, m/z): 582.0 (M + H)⁺. |

Example-4

In vitro biochemical assay for USP30 enzyme

The in vitro assay for USP30 evaluates the ability of a test compound to inhibit the activity of the enzyme to cleave ubiquitin from a substrate. Ubiquitin-rhodamine 110 is a quenched, fluorescent substrate for USP30. Cleavage of the amide bond between the C-terminal glycine of ubiquitin and rhodamine results in an increase in rhodamine fluorescence at 535 nm (Exc. 485 nm). While the di-substituted rhodamine moiety in Ub-Rho110-G is essentially non-fluorescent, cleavage results in a monosubstituted rhodamine, Rho110-G, which exhibits intense fluorescence when excited at 485 nm.

The activity of USP30 was validated by determining the increase in fluorescence measured as a result of the enzyme catalyzed cleavage of the fluorogenic substrate Ubiquitin-Rhodamine110-Glycine generating Ubiquitin and Rhodamine110-Glycine. Incubation of the substrate in the presence or absence of USP30 was compared to confirm the deubiquitylating activity of USP30. The USP30 enzyme assay was performed by pre-incubating 20 nM of USP30 with varying concentration of a test compound in the assay buffer [PBS (pH 7.4), 1 mM DTT, 0.01% Tween 20, 0.01% BSA, DMSO final concentration is 1%] for 15 mins at room temperature, following which 100 nM of substrate Ub rhodamine was added and incubated at room temperature for 2 hrs and the plate was read for fluorescence intensity at Ex. 485 nm/535 nm in VICTOR X5 plate reader. The percent inhibition of activity of the enzyme is calculated by comparing counts in the presence and absence of compounds.

Test compounds were screened at various concentrations (10-12 tested concentrations) and dose response curves were generated was generated using GraphPad Prism software Version 7 (San Diego, Calif., USA) with non-linear regression curve fit for sigmoidal dose response (variable slope).

TABLE 10

| | USP30 IC$_{50}$ Values | | |
|---|---|---|---|
| ID # | Structure | Name | IC$_{50}$ (nM) |
| 4a | | (R)-N-(1-((5-(N-(tert-butyl)sulfamoyl)naphthalen-1-yl)amino)-1-oxo-3-phenylpropan-2-yl)benzamide | 248 |
| 4b | | (S)-N-(1-((5-(N-(tert-butyl)sulfamoyl)naphthalen-1-yl)amino)-1-oxo-3-phenylpropan-2-yl)benzamide | 273 |
| 4c | | (S)-N-(1-((5-(N-(tert-butyl)sulfamoyl)naphthalen-1-yl)amino)-1-oxo-3-phenylpropan-2-yl)cyclohexanecarboxamide | 125 |

TABLE 10-continued

USP30 IC$_{50}$ Values

| ID # | Structure | Name | IC$_{50}$ (nM) |
|---|---|---|---|
| 4d | 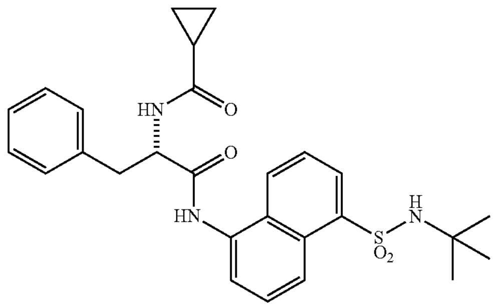 [SMILES: CC(C)(C)NS(=O)(=O)c1cccc2c(NC(=O)[C@H](Cc3ccccc3)NC(=O)C3CC3)cccc12] | (S)-N-(1-((5-(N-(tert-butyl)sulfamoyl)naphthalen-1-yl)amino)-1-oxo-3-phenylpropan-2-yl)cyclopropanecarboxamide | >10,000 |
| 4e | 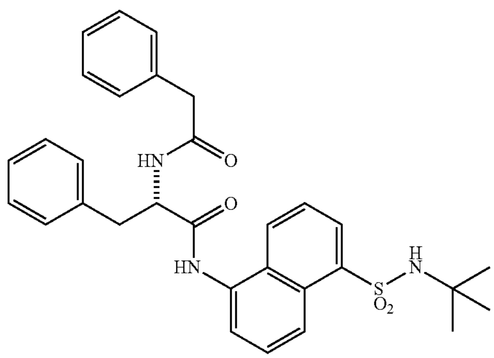 [SMILES: CC(C)(C)NS(=O)(=O)c1cccc2c(NC(=O)[C@H](Cc3ccccc3)NC(=O)Cc3ccccc3)cccc12] | (S)-N-(5-(N-(tert-butyl)sulfamoyl)naphthalen-1-yl)-3-phenyl-2-(2-phenylacetamido)propanamide | >10,000 |
| 4f | 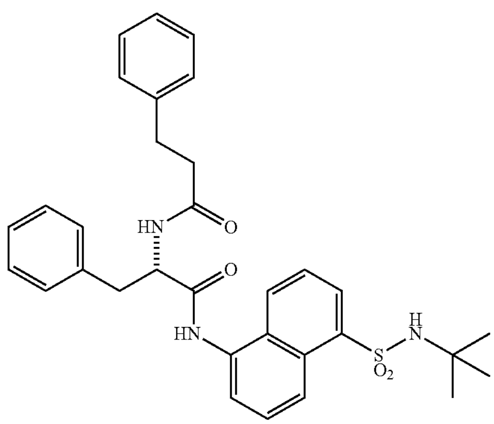 [SMILES: CC(C)(C)NS(=O)(=O)c1cccc2c(NC(=O)[C@H](Cc3ccccc3)NC(=O)CCc3ccccc3)cccc12] | (S)-N-(5-(N-(tert-butyl)sulfamoyl)naphthalen-1-yl)-3-phenyl-2-(3-phenylpropanamido)propanamide | >10,000 |
| 4g | 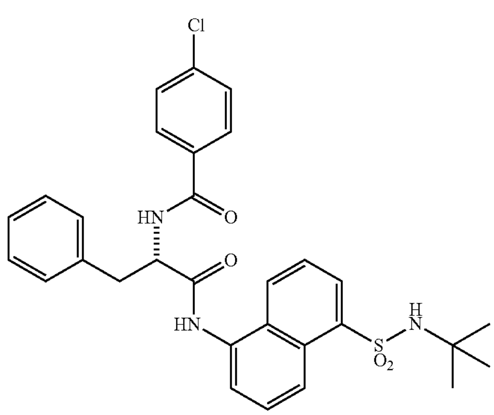 [SMILES: CC(C)(C)NS(=O)(=O)c1cccc2c(NC(=O)[C@H](Cc3ccccc3)NC(=O)c3ccc(Cl)cc3)cccc12] | (S)-N-(1-((5-(N-(tert-butyl)sulfamoyl)naphthalen-1-yl)amino)-1-oxo-3-phenylpropan-2-yl)-4-chlorobenzamide | 833 |

TABLE 10-continued

USP30 IC$_{50}$ Values

| ID # | Structure | Name | IC$_{50}$ (nM) |
|---|---|---|---|
| 4h | 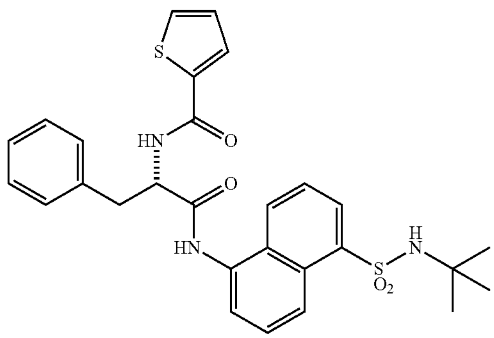 [SMILES: CC(C)(C)NS(=O)(=O)c1cccc2c(NC(=O)[C@H](Cc3ccccc3)NC(=O)c3cccs3)cccc12] | (S)-N-(1-((5-(N-(tert-butyl)sulfamoyl)naphthalen-1-yl)amino)-1-oxo-3-phenylpropan-2-yl)thiophene-2-carboxamide | 1,800 |
| 4i | 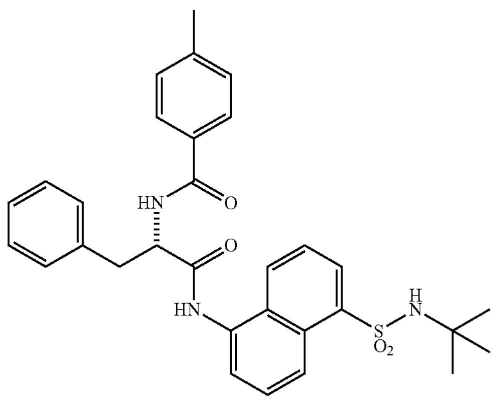 [SMILES: Cc1ccc(C(=O)N[C@@H](Cc2ccccc2)C(=O)Nc2cccc3c(S(=O)(=O)NC(C)(C)C)cccc23)cc1] | (S)-N-(1-((5-(N-(tert-butyl)sulfamoyl)naphthalen-1-yl)amino)-1-oxo-3-phenylpropan-2-yl)-4-methylbenzamide | 2500 |
| 4j | 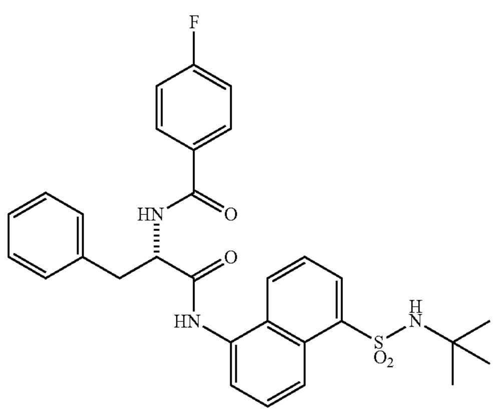 [SMILES: CC(C)(C)NS(=O)(=O)c1cccc2c(NC(=O)[C@H](Cc3ccccc3)NC(=O)c3ccc(F)cc3)cccc12] | (S)-N-(1-((5-(N-(tert-butyl)sulfamoyl)naphthalen-1-yl)amino)-1-oxo-3-phenylpropan-2-yl)-4-fluorobenzamide | 49 |
| 4k | 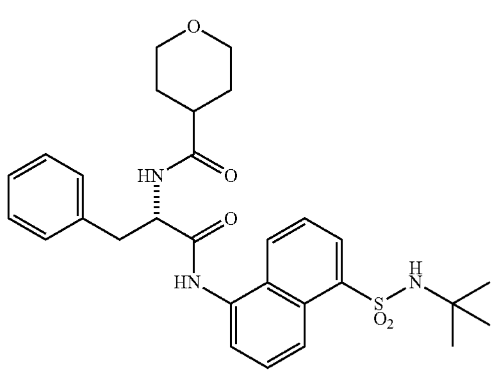 [SMILES: CC(C)(C)NS(=O)(=O)c1cccc2c(NC(=O)[C@H](Cc3ccccc3)NC(=O)C3CCOCC3)cccc12] | (S)-N-(1-((5-(N-(tert-butyl)sulfamoyl)naphthalen-1-yl)amino)-1-oxo-3-phenylpropan-2-yl)tetrahydro-2H-pyran-4-carboxamide | >10,000 |

TABLE 10-continued

| | USP30 IC$_{50}$ Values | | |
|---|---|---|---|
| ID # | Structure | Name | IC$_{50}$ (nM) |
| 4l | | (S)-N-(1-((5-(N-(tert-butyl)sulfamoyl)naphthalen-1-yl)amino)-1-oxo-3-phenylpropan-2-yl)cyclopentanecarboxamide | 366 |
| 4m | | (S)-N-(1-((5-(N-(tert-butyl)sulfamoyl)naphthalen-1-yl)amino)-1-oxo-3-phenylpropan-2-yl)-6-methylpicolinamide | >10,000 |
| 4n | | (S)-N-(1-((5-(N-(tert-butyl)sulfamoyl)naphthalen-1-yl)amino)-1-oxo-3-phenylpropan-2-yl)-4,4-difluorocyclohexane-1-carboxamide | 98 |
| 4o | | (S)-N-(1-((5-(N-(tert-butyl)sulfamoyl)naphthalen-1-yl)amino)-1-oxo-3-phenylpropan-2-yl)pyrimidine-2-carboxamide | >10,000 |

TABLE 10-continued

USP30 IC$_{50}$ Values

| ID # | Structure | Name | IC$_{50}$ (nM) |
|---|---|---|---|
| 4p | 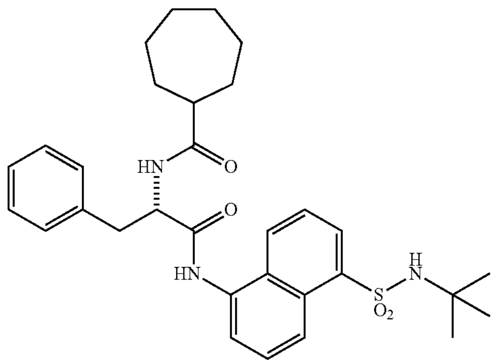 [SMILES: CC(C)(C)NS(=O)(=O)c1cccc2c(NC(=O)[C@H](Cc3ccccc3)NC(=O)C3CCCCCC3)cccc12] | (S)-N-(1-((5-(N-(tert-butyl)sulfamoyl)naphthalen-1-yl)amino)-1-oxo-3-phenylpropan-2-yl)cycloheptanecarboxamide | 4,300 |
| 4q | 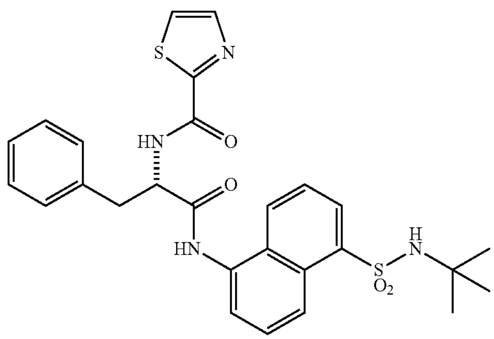 [SMILES: CC(C)(C)NS(=O)(=O)c1cccc2c(NC(=O)[C@H](Cc3ccccc3)NC(=O)c3nccs3)cccc12] | (S)-N-(1-((5-(N-(tert-butyl)sulfamoyl)naphthalen-1-yl)amino)-1-oxo-3-phenylpropan-2-yl)thiazole-2-carboxamide | 180 |
| 4r | 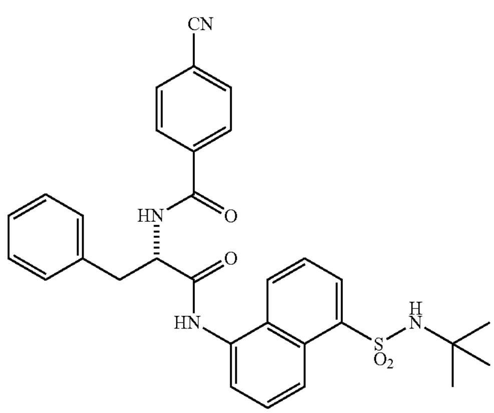 [SMILES: CC(C)(C)NS(=O)(=O)c1cccc2c(NC(=O)[C@H](Cc3ccccc3)NC(=O)c3ccc(C#N)cc3)cccc12] | (S)-N-(1-((5-(N-(tert-butyl)sulfamoyl)naphthalen-1-yl)amino)-1-oxo-3-phenylpropan-2-yl)-4-cyanobenzamide | 269 |
| 4s | 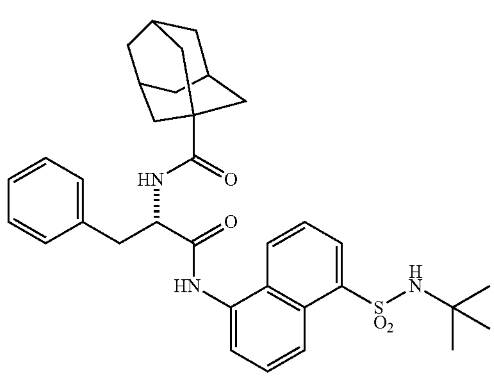 [SMILES: CC(C)(C)NS(=O)(=O)c1cccc2c(NC(=O)[C@H](Cc3ccccc3)NC(=O)C34CC5CC(CC(C5)C3)C4)cccc12] | (S)-N-1-((5-(N-(tert-butyl)sulfamoyl)naphthalen-1-yl)amino)-1-oxo-3-phenylpropan-2-yl)adamantane-1-carboxamide | >10,000 |

TABLE 10-continued

USP30 IC$_{50}$ Values

| ID # | Structure | Name | IC$_{50}$ (nM) |
|---|---|---|---|
| 4t | 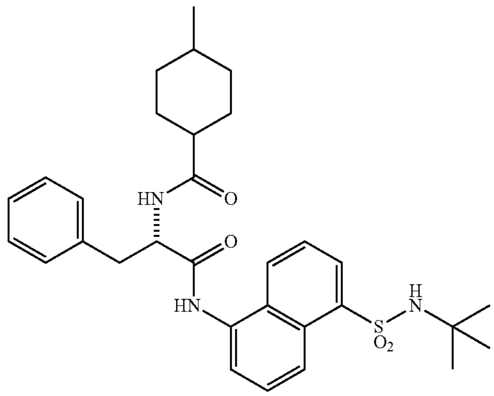 [SMILES: CC1CCC(C(=O)N[C@@H](Cc2ccccc2)C(=O)Nc2cccc3c(S(=O)(=O)NC(C)(C)C)cccc23)CC1] | (S)-N-(1-((5-(N-(tert-butyl)sulfamoyl)naphthalen-1-yl)amino)-1-oxo-3-phenylpropan-2-yl)-4-methylcyclohexane-1-carboxamide | >10,000 |
| 4u | 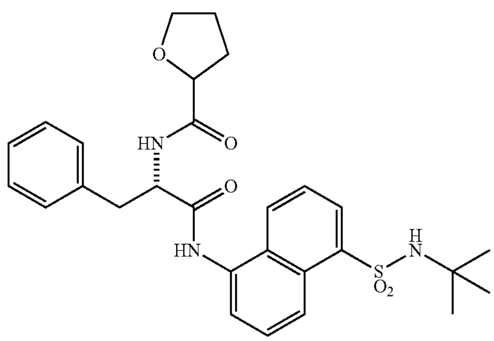 [SMILES: CC(C)(C)NS(=O)(=O)c1cccc2c(NC(=O)[C@H](Cc3ccccc3)NC(=O)C3CCCO3)cccc12] | N-((S)-1-((5-(N-(tert-butyl)sulfamoyl)naphthalen-1-yl)amino)-1-oxo-3-phenylpropan-2-yl)tetrahydrofuran-2-carboxamide | >10,000 |
| 4v | 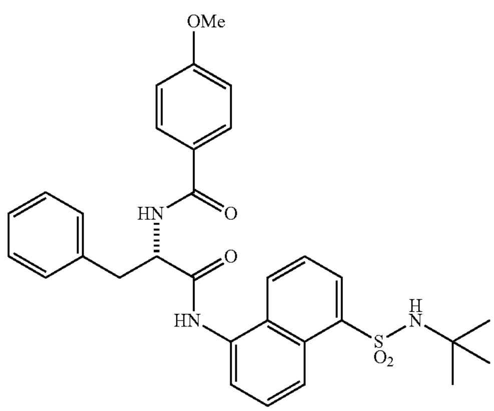 | (S)-N-(1-((5-(N-(tert-butyl)sulfamoyl)naphthalen-1-yl)amino)-1-oxo-3-phenylpropan-2-yl)-4-methoxybenzamide | 9,000 |
| 4w | 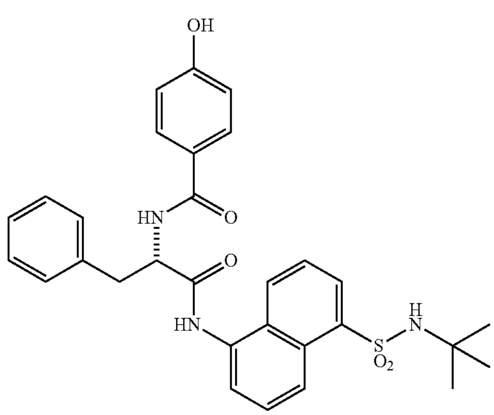 | (S)-N-(1-((5-(N-(tert-butyl)sulfamoyl)naphthalen-1-yl)amino)-1-oxo-3-phenylpropan-2-yl)-4-hydroxybenzamide | >10,000 |

TABLE 10-continued

USP30 IC$_{50}$ Values

| ID # | Structure | Name | IC$_{50}$ (nM) |
|---|---|---|---|
| 4x | 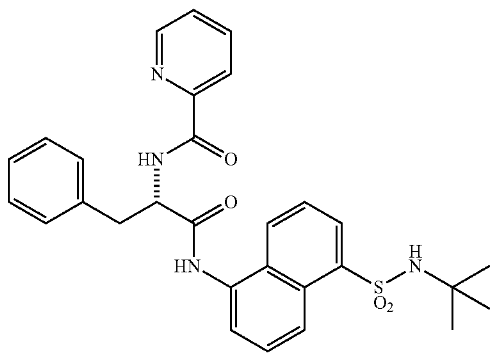 [SMILES: CC(C)(C)NS(=O)(=O)c1cccc2c(NC(=O)[C@H](Cc3ccccc3)NC(=O)c3ccccn3)cccc12] | (S)-N-(1-((5-(N-(tert-butyl)sulfamoyl)naphthalen-1-yl)amino)-1-oxo-3-phenylpropan-2-yl)picolinamide | 170 |
| 4y | 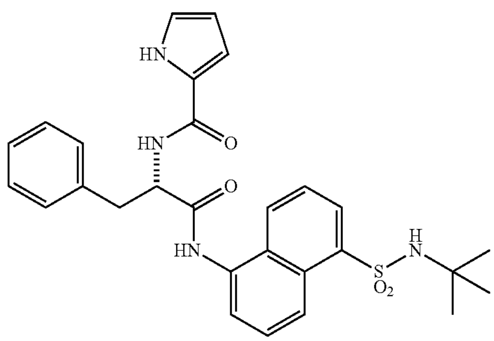 | (S)-N-(1-((5-(N-(tert-butyl)sulfamoyl)naphthalen-1-yl)amino)-1-oxo-3-phenylpropan-2-yl)-1H-pyrrole-2-carboxamide | 1,900 |
| 4z | 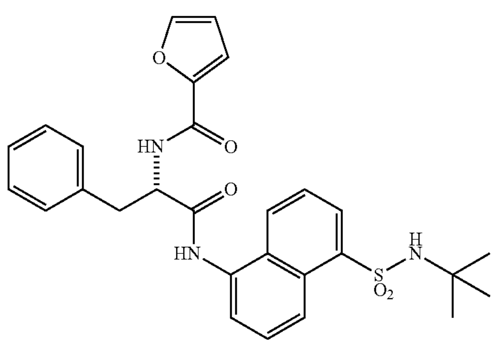 [SMILES: CC(C)(C)NS(=O)(=O)c1cccc2c(NC(=O)[C@H](Cc3ccccc3)NC(=O)c3ccco3)cccc12] | (S)-N-(1-((5-(N-(tert-butyl)sulfamoyl)naphthalen-1-yl)amino)-1-oxo-3-phenylpropan-2-yl)furan-2-carboxamide | >10,000 |
| 7a | 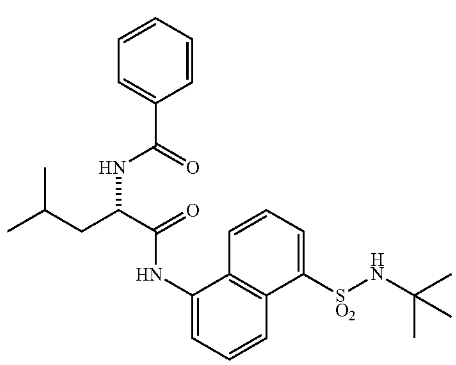 [SMILES: CC(C)C[C@H](NC(=O)c1ccccc1)C(=O)Nc1cccc2c(S(=O)(=O)NC(C)(C)C)cccc12] | (S)-N-(1-((5-(N-(tert-butyl)sulfamoyl)naphthalen-1-yl)amino)-4-methyl-1-oxopentan-2-yl)benzamide | 4,300 |

TABLE 10-continued

USP30 IC$_{50}$ Values

| ID # | Structure | Name | IC$_{50}$ (nM) |
|---|---|---|---|
| 7b | 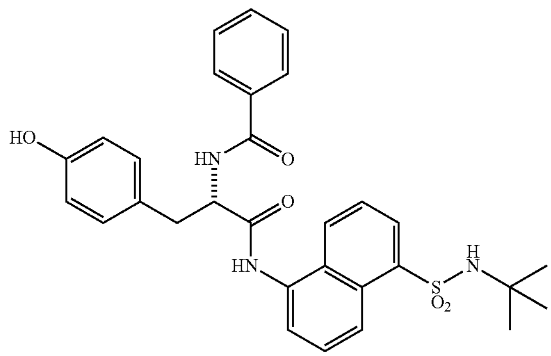 [SMILES: CC(C)(C)NS(=O)(=O)c1cccc2c(NC(=O)[C@H](Cc3ccc(O)cc3)NC(=O)c3ccccc3)cccc12] | (S)-N-(1-((5-(N-(tert-butyl)sulfamoyl)naphthalen-1-yl)amino)-3-(4-hydroxyphenyl)-1-oxopropan-2-yl)benzamide | 520 |
| 7c | 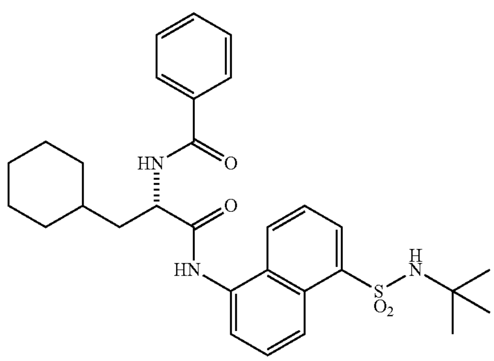 [SMILES: CC(C)(C)NS(=O)(=O)c1cccc2c(NC(=O)[C@H](CC3CCCCC3)NC(=O)c3ccccc3)cccc12] | (S)-N-(1-((5-(N-(tert-butyl)sulfamoyl)naphthalen-1-yl)amino)-3-cyclohexyl-1-oxopropan-2-yl)benzamide | 666 |
| 7d | 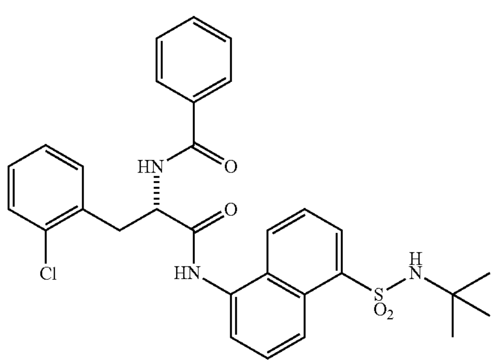 [SMILES: CC(C)(C)NS(=O)(=O)c1cccc2c(NC(=O)[C@H](Cc3ccccc3Cl)NC(=O)c3ccccc3)cccc12] | (S)-N-(1-((5-(N-(tert-butyl)sulfamoyl)naphthalen-1-yl)amino)-3-(2-chlorophenyl)-1-oxopropan-2-yl)benzamide | >10,000 |
| 7e | 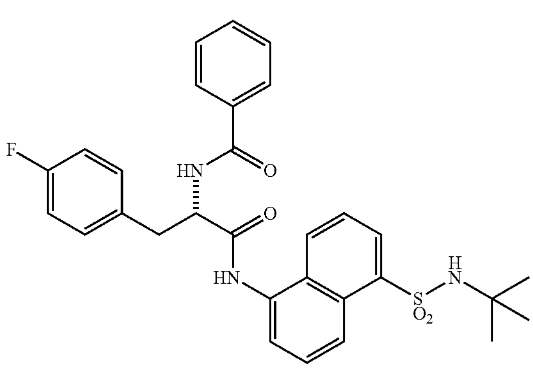 [SMILES: CC(C)(C)NS(=O)(=O)c1cccc2c(NC(=O)[C@H](Cc3ccc(F)cc3)NC(=O)c3ccccc3)cccc12] | (S)-N-(1-((5-(N-(tert-butyl)sulfamoyl)naphthalen-1-yl)amino)-3-(4-fluorophenyl)-1-oxopropan-2-yl)benzamide | 153 |

TABLE 10-continued

USP30 IC$_{50}$ Values

| ID # | Structure | Name | IC$_{50}$ (nM) |
|---|---|---|---|
| 7f | 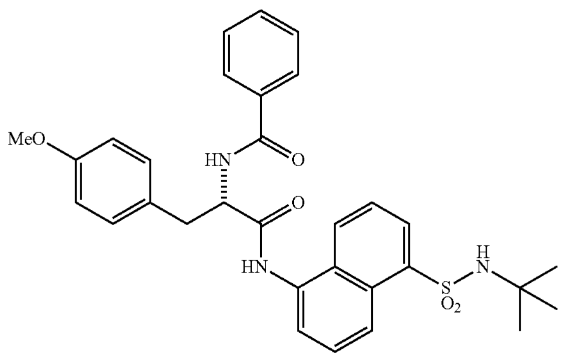 [SMILES: COc1ccc(C[C@H](NC(=O)c2ccccc2)C(=O)Nc2cccc3c(S(=O)(=O)NC(C)(C)C)cccc23)cc1] | (S)-N-(1-((5-(N-(tert-butyl)sulfamoyl)naphthalen-1-yl)amino)-3-(4-methoxyphenyl)-1-oxopropan-2-yl)benzamide | 89 |
| 7g | 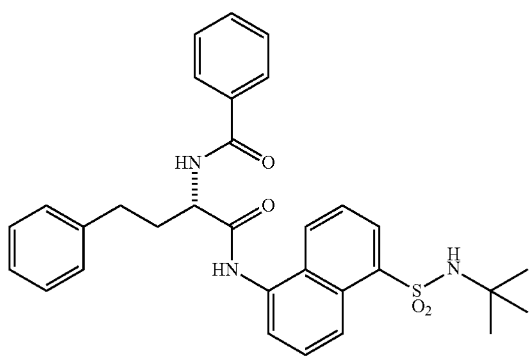 [SMILES: CC(C)(C)NS(=O)(=O)c1cccc2c(NC(=O)[C@H](CCc3ccccc3)NC(=O)c3ccccc3)cccc12] | (S)-N-(1-((5-(N-(tert-butyl)sulfamoyl)naphthalen-1-yl)amino)-1-oxo-4-phenylbutan-2-yl)benzamide | 2,270 |
| 7h | 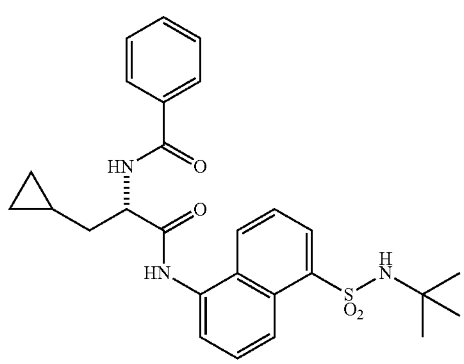 [SMILES: CC(C)(C)NS(=O)(=O)c1cccc2c(NC(=O)[C@H](CC3CC3)NC(=O)c3ccccc3)cccc12] | (S)-N-(1-((5-(N-(tert-butyl)sulfamoyl)naphthalen-1-yl)amino)-3-cyclopropyl-1-oxopropan-2-yl)benzamide | 2,200 |
| 7i | 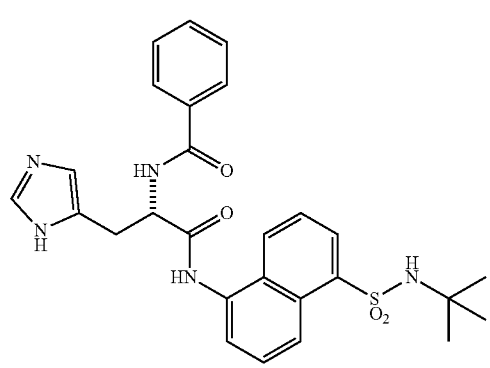 [SMILES: CC(C)(C)NS(=O)(=O)c1cccc2c(NC(=O)[C@H](Cc3cnc[nH]3)NC(=O)c3ccccc3)cccc12] | (S)-N-(1-((5-(N-(tert-butyl)sulfamoyl)naphthalen-1-yl)amino)-3-(1H-imidazol-5-yl)-1-oxopropan-2-yl)benzamide | >10,000 |

TABLE 10-continued

USP30 IC$_{50}$ Values

| ID # | Structure | Name | IC$_{50}$ (nM) |
|---|---|---|---|
| 7j | 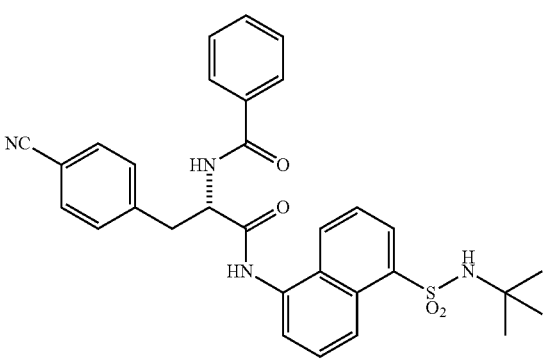 [SMILES: CC(C)(C)NS(=O)(=O)c1cccc2c(NC(=O)[C@H](Cc3ccc(C#N)cc3)NC(=O)c3ccccc3)cccc12] | (S)-N-(1-((5-(N-(tert-butyl)sulfamoyl)naphthalen-1-yl)amino)-3-(4-cyanophenyl)-1-oxopropan-2-yl)benzamide | 273 |
| 7k | 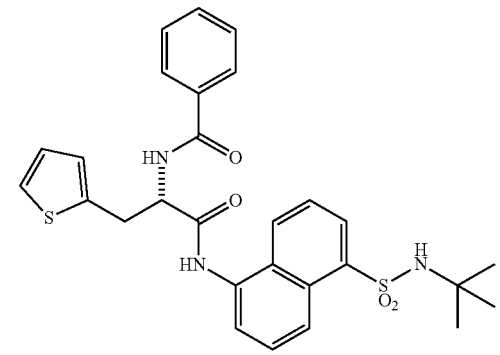 [SMILES: CC(C)(C)NS(=O)(=O)c1cccc2c(NC(=O)[C@H](Cc3cccs3)NC(=O)c3ccccc3)cccc12] | (S)-N-(1-((5-(N-(tert-butyl)sulfamoyl)naphthalen-1-yl)amino)-1-oxo-3-(thiophen-2-yl)propan-2-yl)benzamide | 230 |
| 7l | 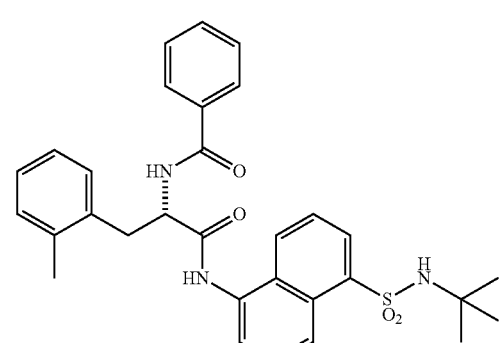 | (S)-N-(1-((5-(N-(tert-butyl)sulfamoyl)naphthalen-1-yl)amino)-1-oxo-3-(o-tolyl)propan-2-yl)benzamide | >10,000 |
| 7m | 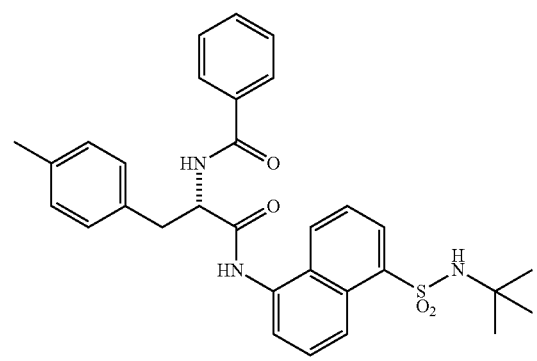 [SMILES: Cc1ccc(C[C@H](NC(=O)c2ccccc2)C(=O)Nc2cccc3c(S(=O)(=O)NC(C)(C)C)cccc23)cc1] | (S)-N-(1-((5-(N-(tert-butyl)sulfamoyl)naphthalen-1-yl)amino)-1-oxo-3-(p-tolyl)propan-2-yl)benzamide | >10,000 |

TABLE 10-continued

USP30 IC$_{50}$ Values

| ID # | Structure | Name | IC$_{50}$ (nM) |
|---|---|---|---|
| 7n | 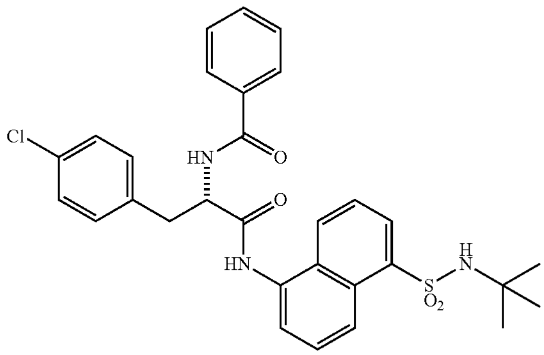 [SMILES: CC(C)(C)NS(=O)(=O)c1cccc2c(NC(=O)[C@H](Cc3ccc(Cl)cc3)NC(=O)c3ccccc3)cccc12] | (S)-N-(1-((5-(N-(tert-butyl)sulfamoyl)naphthalen-1-yl)amino)-3-(4-chlorophenyl)-1-oxopropan-2-yl)benzamide | 446 |
| 10a | 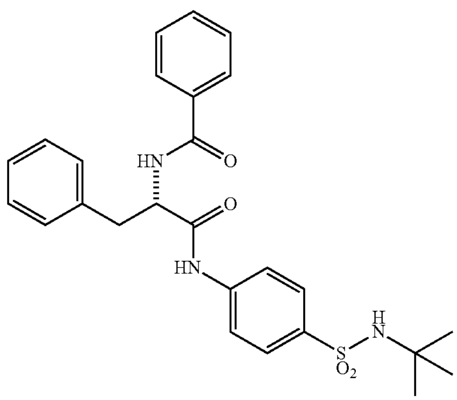 [SMILES: CC(C)(C)NS(=O)(=O)c1ccc(NC(=O)[C@H](Cc2ccccc2)NC(=O)c2ccccc2)cc1] | (S)-N-(1-((4-(N-(tert-butyl)sulfamoyl)phenyl)amino)-1-oxo-3-phenylpropan-2-yl)benzamide | >10,000 |
| 10b | 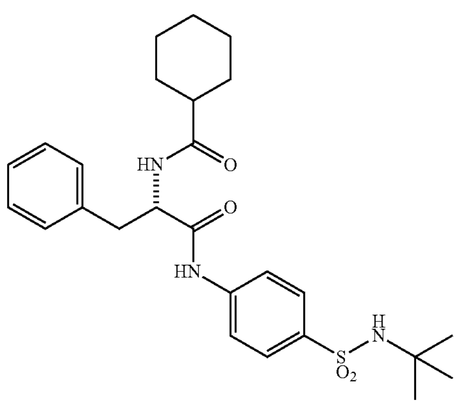 [SMILES: CC(C)(C)NS(=O)(=O)c1ccc(NC(=O)[C@H](Cc2ccccc2)NC(=O)C2CCCCC2)cc1] | (S)-N-(1-((4-(N-(tert-butyl)sulfamoyl)phenyl)amino)-1-oxo-3-phenylpropan-2-yl)cyclohexanecarboxamide | 59 |
| 10c | 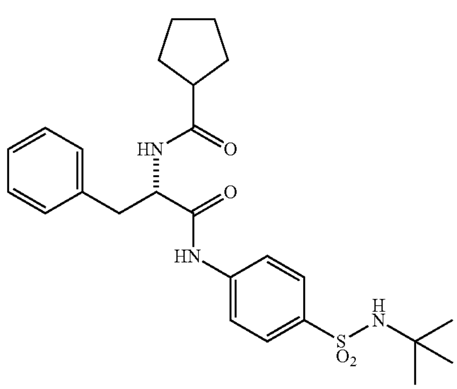 [SMILES: CC(C)(C)NS(=O)(=O)c1ccc(NC(=O)[C@H](Cc2ccccc2)NC(=O)C2CCCC2)cc1] | (S)-N-(1-((4-(N-(tert-butyl)sulfamoyl)phenyl)amino)-1-oxo-3-phenylpropan-2-yl)cyclopentanecarboxamide | 71 |

TABLE 10-continued

USP30 IC$_{50}$ Values

| ID # | Structure | Name | IC$_{50}$ (nM) |
|---|---|---|---|
| 10d | 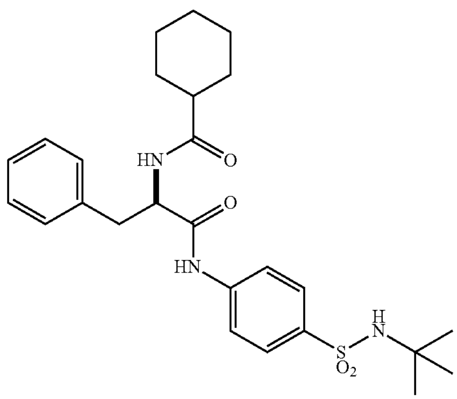 [SMILES: CC(C)(C)NS(=O)(=O)c1ccc(NC(=O)[C@@H](Cc2ccccc2)NC(=O)C2CCCCC2)cc1] | (R)-N-(1-((4-(N-(tert-butyl)sulfamoyl)phenyl)amino)-1-oxo-3-phenylpropan-2-yl)cyclohexanecarboxamide | 28 |
| 10e | 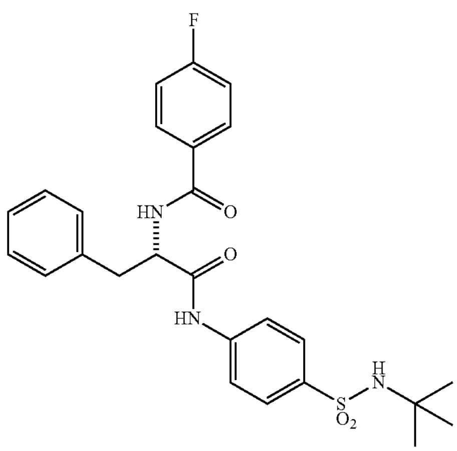 [SMILES: CC(C)(C)NS(=O)(=O)c1ccc(NC(=O)[C@H](Cc2ccccc2)NC(=O)c2ccc(F)cc2)cc1] | (S)-N-(1-((4-(tert-butyl)sulfamoyl)phenyl)amino)-1-oxo-3-phenylpropan-2-yl)-4-fluorobenzamide | 17 |
| 10f | 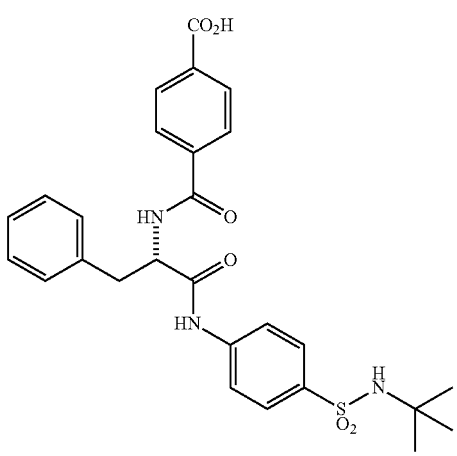 [SMILES: CC(C)(C)NS(=O)(=O)c1ccc(NC(=O)[C@H](Cc2ccccc2)NC(=O)c2ccc(C(=O)O)cc2)cc1] | (S)-4-((1-((4-(N-(tert-butyl)sulfamoyl)phenyl)amino)-1-oxo-3-phenylpropan-2-yl)carbamoyl)benzoic acid | >10,000 |

TABLE 10-continued

| | USP30 IC$_{50}$ Values | | |
|---|---|---|---|
| ID # | Structure | Name | IC$_{50}$ (nM) |
| 10g | | methyl (S)-4-((1-((4-(N-(tert-butyl)sulfamoyl)phenyl)amino)-1-oxo-3-phenylpropan-2-yl)carbamoyl)benzoate | >10,000 |
| 10h | | (S)-N-(1-((4-(N-(tert-butyl)sulfamoyl)phenyl)amino)-1-oxo-3-phenylpropan-2-yl)picolinamide | 250 |
| 10i | | (S)-N-((S)-1-((4-(N-(tert-butyl)sulfamoyl)phenyl)amino)-1-oxo-3-phenylpropan-2-yl)pyrrolidine-2-carboxamide | >10,000 |

TABLE 10-continued

USP30 IC$_{50}$ Values

| ID # | Structure | Name | IC$_{50}$ (nM) |
|---|---|---|---|
| 10j | 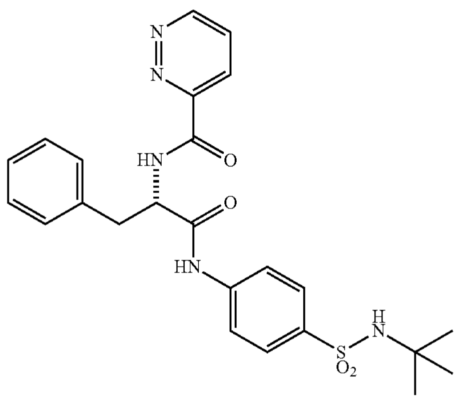 [SMILES: CC(C)(C)NS(=O)(=O)c1ccc(NC(=O)[C@H](Cc2ccccc2)NC(=O)c2cccnn2)cc1] | (S)-N-(1-((4-(N-(tert-butyl)sulfamoyl)phenyl)amino)-1-oxo-3-phenylpropan-2-yl)pyridazine-3-carboxamide | 148 |
| 14a | 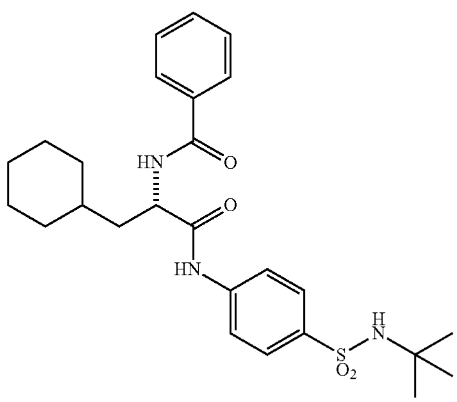 [SMILES: CC(C)(C)NS(=O)(=O)c1ccc(NC(=O)[C@H](CC2CCCCC2)NC(=O)c2ccccc2)cc1] | (S)-N-(1-((4-(N-(tert-butyl)sulfamoyl)phenyl)amino)-3-cyclohexyl-1-oxopropan-2-yl)benzamide | 225 |
| 14b | 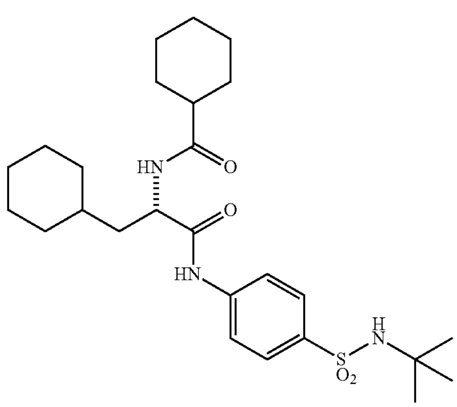 [SMILES: CC(C)(C)NS(=O)(=O)c1ccc(NC(=O)[C@H](CC2CCCCC2)NC(=O)C2CCCCC2)cc1] | (S)-N-(1-((4-(N-(tert-butyl)sulfamoyl)phenyl)amino)-3-cyclohexyl-1-oxopropan-2-yl)cyclohexanecarboxamide | 83 |

TABLE 10-continued

USP30 IC$_{50}$ Values

| ID # | Structure | Name | IC$_{50}$ (nM) |
|---|---|---|---|
| 14c | 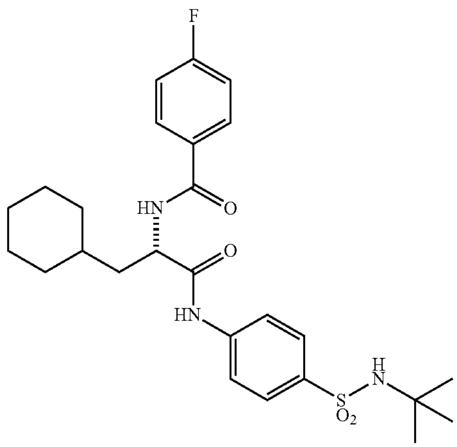 [SMILES: CC(C)(C)NS(=O)(=O)c1ccc(NC(=O)[C@H](CC2CCCCC2)NC(=O)c2ccc(F)cc2)cc1] | (S)-N-(1-((4-(N-(tert-butyl)sulfamoyl)phenyl)amino)-3-cyclohexyl-1-oxopropan-2-yl)-4-fluorobenzamide | 23 |
| 14d | 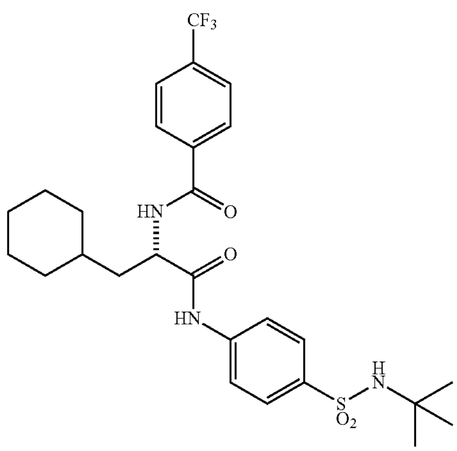 [SMILES: CC(C)(C)NS(=O)(=O)c1ccc(NC(=O)[C@H](CC2CCCCC2)NC(=O)c2ccc(C(F)(F)F)cc2)cc1] | (S)-N-(1-((4-(N-(tert-butyl)sulfamoyl)phenyl)amino)-3-cyclohexyl-1-oxopropan-2-yl)-4-(trifluoromethyl)benzamide | >10,000 |
| 14e | 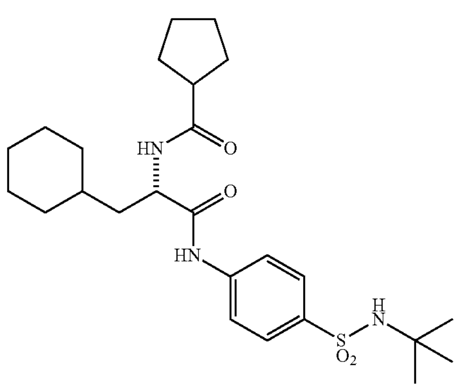 [SMILES: CC(C)(C)NS(=O)(=O)c1ccc(NC(=O)[C@H](CC2CCCCC2)NC(=O)C2CCCC2)cc1] | (S)-N-(1-((4-(N-(tert-butyl)sulfamoyl)phenyl)amino)-3-cyclohexyl-1-oxopropan-2-yl)cyclopentanecarboxamide | 120 |

TABLE 10-continued

USP30 IC$_{50}$ Values

| ID # | Structure | Name | IC$_{50}$ (nM) |
|---|---|---|---|
| 14f | 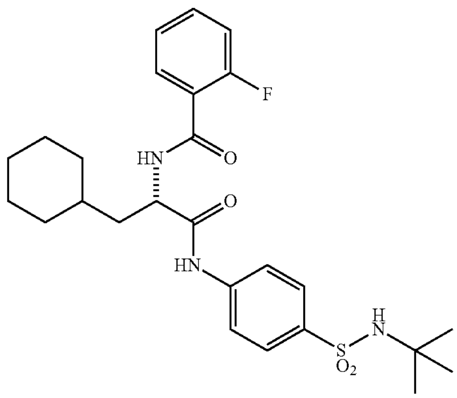 [SMILES: CC(C)(C)NS(=O)(=O)c1ccc(NC(=O)[C@H](CC2CCCCC2)NC(=O)c2ccccc2F)cc1] | (S)-N-(1-((4-(N-(tert-butyl)sulfamoyl)phenyl)amino)-3-cyclohexyl-1-oxopropan-2-yl)-2-fluorobenzamide | 461 |
| 14g | 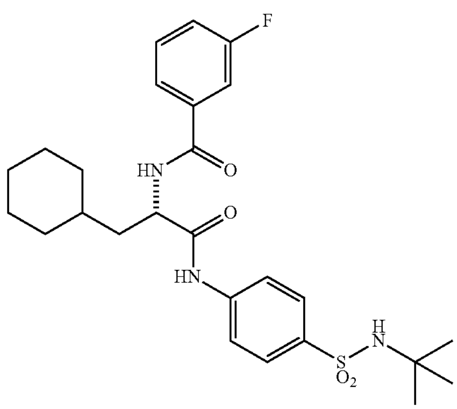 [SMILES: CC(C)(C)NS(=O)(=O)c1ccc(NC(=O)[C@H](CC2CCCCC2)NC(=O)c2cccc(F)c2)cc1] | (S)-N-(1-((4-(N-(tert-butyl)sulfamoyl)phenyl)amino)-3-cyclohexyl-1-oxopropan-2-yl)-3-fluorobenzamide | 57 |
| 14h | 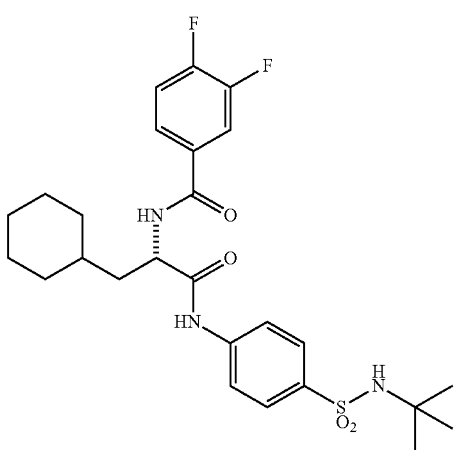 [SMILES: CC(C)(C)NS(=O)(=O)c1ccc(NC(=O)[C@H](CC2CCCCC2)NC(=O)c2ccc(F)c(F)c2)cc1] | (S)-N-(1-((4-(N-(tert-butyl)sulfamoyl)phenyl)amino)-3-cyclohexyl-1-oxopropan-2-yl)-3,4-difluorobenzamide | 31 |

TABLE 10-continued

USP30 IC$_{50}$ Values

| ID # | Structure | Name | IC$_{50}$ (nM) |
| --- | --- | --- | --- |
| 14i | 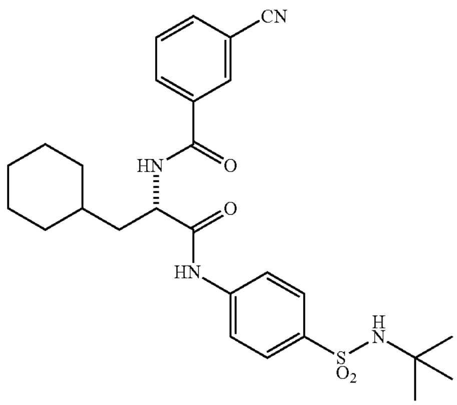 [SMILES: CC(C)(C)NS(=O)(=O)c1ccc(NC(=O)[C@H](CC2CCCCC2)NC(=O)c2cccc(C#N)c2)cc1] | (S)-N-(1-((4-(N-(tert-butyl)sulfamoyl)phenyl)amino)-3-cyclohexyl-1-oxopropan-2-yl)-3-cyanobenzamide | >10,000 |
| 14j | 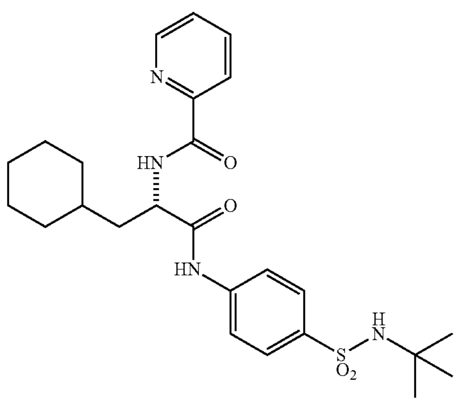 [SMILES: CC(C)(C)NS(=O)(=O)c1ccc(NC(=O)[C@H](CC2CCCCC2)NC(=O)c2ccccn2)cc1] | (S)-N-(1-((4-(N-(tert-butyl)sulfamoyl)phenyl)amino)-3-cyclohexyl-1-oxopropan-2-yl)picolinamide | 123 |
| 19a | 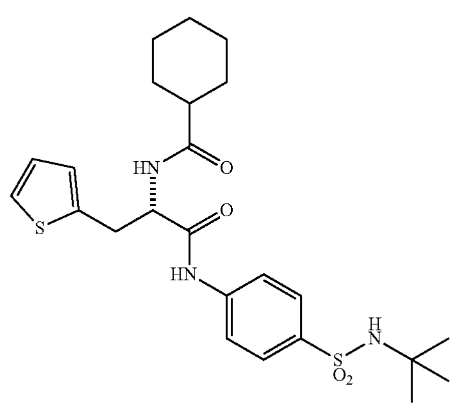 [SMILES: CC(C)(C)NS(=O)(=O)c1ccc(NC(=O)[C@H](Cc2cccs2)NC(=O)C2CCCCC2)cc1] | (S)-N-(1-((4-(N-(tert-butyl)sulfamoyl)phenyl)amino)-1-oxo-3-(thiophen-2-yl)propan-2-yl)cyclohexanecarboxamide | 28 |

TABLE 10-continued

| | USP30 IC$_{50}$ Values | | |
|---|---|---|---|
| ID # | Structure | Name | IC$_{50}$ (nM) |
| 19b | | (S)-N-(1-((4-(N-(tert-butyl)sulfamoyl)phenyl)amino)-3-(4-fluorophenyl)-1-oxopropan-2-yl)benzamide | 133 |
| 19c | | (S)-N-(1-((4-(N-(tert-butyl)sulfamoyl)phenyl)amino)-3-cyclopropyl-1-oxopropan-2-yl)cyclohexanecarboxamide | 810 |
| 19d | | (S)-N-(1-((4-(N-(tert-butyl)sulfamoyl)-3-methylphenyl)amino)-1-oxo-3-phenylpropan-2-yl)cyclohexanecarboxamide | >10,000 |

TABLE 10-continued

USP30 IC$_{50}$ Values

| ID # | Structure | Name | IC$_{50}$ (nM) |
|---|---|---|---|
| 19e | 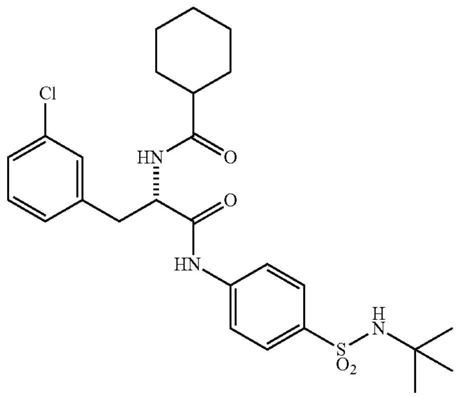 [SMILES: CC(C)(C)NS(=O)(=O)c1ccc(NC(=O)[C@H](Cc2cccc(Cl)c2)NC(=O)C2CCCCC2)cc1] | (S)-N-(1-((4-(N-(tert-butyl)sulfamoyl)phenyl)amino)-3-(3-chlorophenyl)-1-oxopropan-2-yl)cyclohexanecarboxamide | >10,000 |
| 19f | 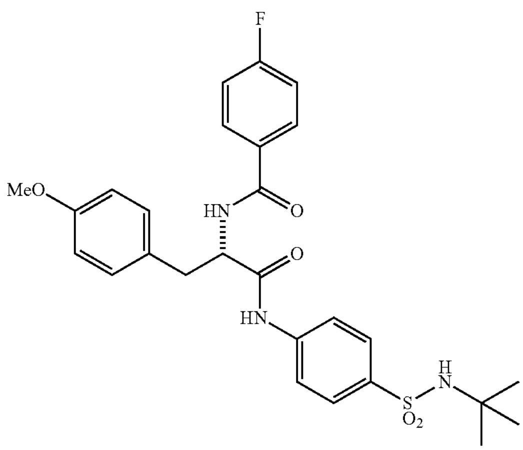 [SMILES: COc1ccc(C[C@H](NC(=O)c2ccc(F)cc2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)-4-fluorobenzamide | 22 |
| 19g | 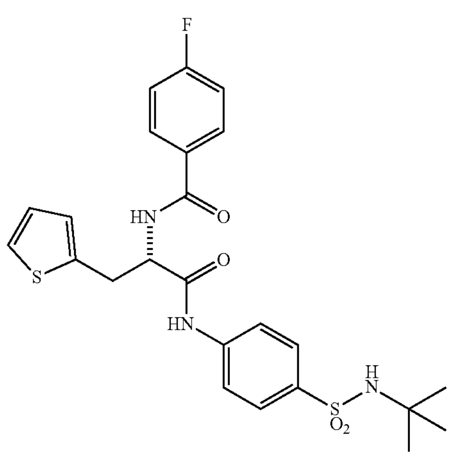 [SMILES: CC(C)(C)NS(=O)(=O)c1ccc(NC(=O)[C@H](Cc2cccs2)NC(=O)c2ccc(F)cc2)cc1] | (S)-N-(1-((4-(N-(tert-butyl)sulfamoyl)phenyl)amino)-1-oxo-3-(thiophen-2-yl)propan-2-yl)-4-fluorobenzamide | 19 |

TABLE 10-continued
USP30 IC$_{50}$ Values
| ID # | Structure | Name | IC$_{50}$ (nM) |
|---|---|---|---|
| 19h | 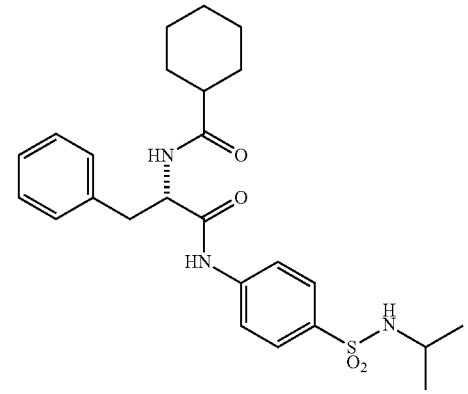 | (S)-N-(1-((4-(N-isopropylsulfamoyl)phenyl)amino)-1-oxo-3-phenylpropan-2-yl)cyclohexanecarboxamide | 179 |
| 19i | 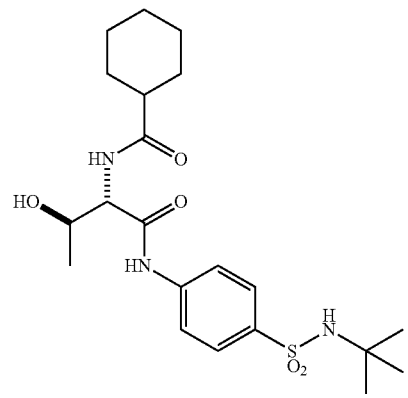 [SMILES: C[C@@H](O)[C@H](NC(=O)C1CCCCC1)C(=O)Nc1ccc(S(=O)(=O)NC(C)(C)C)cc1] | N-((2S,3R)-1-((4-(N-(tert-butyl)sulfamoyl)phenyl)amino)-3-hydroxy-1-oxobutan-2-yl)cyclohexanecarboxamide | >10,000 |
| 19j | 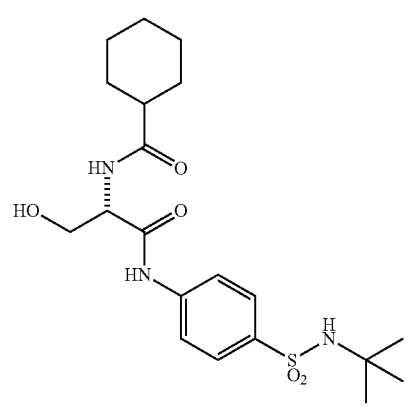 [SMILES: CC(C)(C)NS(=O)(=O)c1ccc(NC(=O)[C@H](CO)NC(=O)C2CCCCC2)cc1] | (S)-N-(1-((4-(N-(tert-butyl)sulfamoyl)phenyl)amino)-3-hydroxy-1-oxopropan-2-yl)cyclohexanecarboxamide | >10,000 |

TABLE 10-continued

USP30 IC$_{50}$ Values

| ID # | Structure | Name | IC$_{50}$ (nM) |
|---|---|---|---|
| 19k | 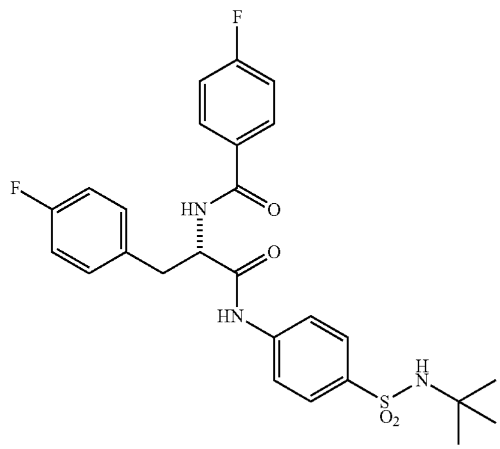 [SMILES: CC(C)(C)NS(=O)(=O)c1ccc(NC(=O)[C@H](Cc2ccc(F)cc2)NC(=O)c2ccc(F)cc2)cc1] | (S)-N-(1-((4-(N-(tert-butyl)sulfamoyl)phenyl)amino)-3-(4-fluorophenyl)-1-oxopropan-2-yl)-4-fluorobenzamide | 26 |
| 19l | 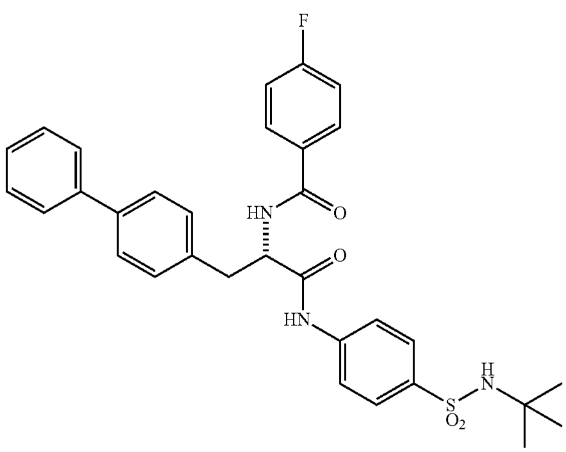 [SMILES: CC(C)(C)NS(=O)(=O)c1ccc(NC(=O)[C@H](Cc2ccc(-c3ccccc3)cc2)NC(=O)c2ccc(F)cc2)cc1] | (S)-N-(3-([1,1'-biphenyl]-4-yl)-1-((4-(N-(tert-butyl)sulfamoyl)phenyl)amino)-1-oxopropan-2-yl)-4-fluorobenzamide | 169 |
| 19m | 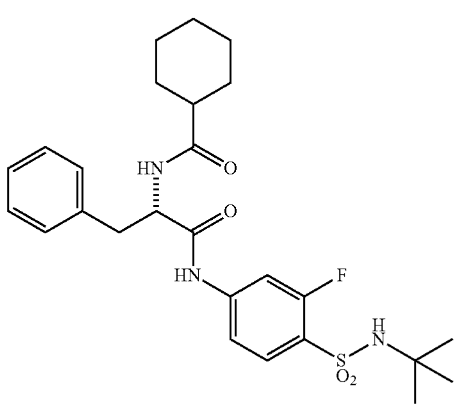 | (S)-N-(1-((4-(N-(tert-butyl)sulfamoyl)-3-fluorophenyl)amino)-1-oxo-3-phenylpropan-2-yl)cyclohexanecarboxamide | 275 |

TABLE 10-continued

USP30 IC$_{50}$ Values

| ID # | Structure | Name | IC$_{50}$ (nM) |
|---|---|---|---|
| 19n | 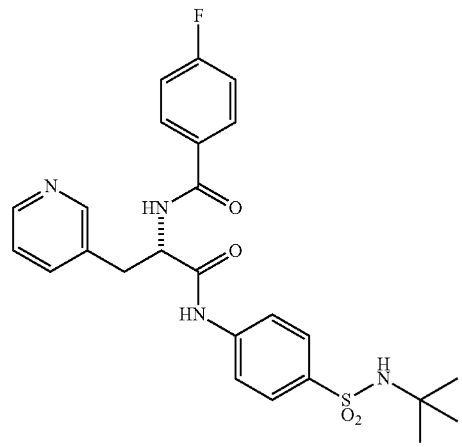 [SMILES: CC(C)(C)NS(=O)(=O)c1ccc(NC(=O)[C@H](Cc2cccnc2)NC(=O)c2ccc(F)cc2)cc1] | (S)-N-(1-((4-(N-(tert-butyl)sulfamoyl)phenyl)amino)-1-oxo-3-(pyridin-3-yl)propan-2-yl)-4-fluorobenzamide | 16 |
| 19o | 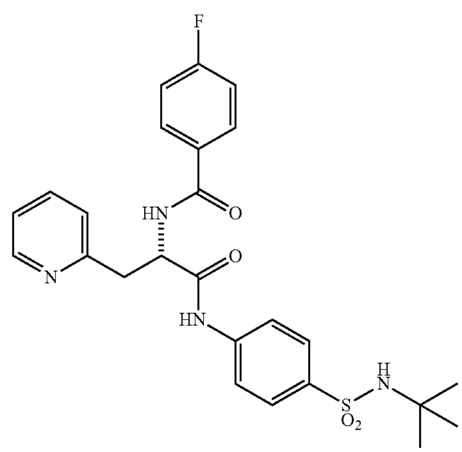 [SMILES: CC(C)(C)NS(=O)(=O)c1ccc(NC(=O)[C@H](Cc2ccccn2)NC(=O)c2ccc(F)cc2)cc1] | (S)-N-(1-((4-(N-(tert-butyl)sulfamoyl)phenyl)amino)-1-oxo-3-(pyridin-2-yl)propan-2-yl)-4-fluorobenzamide | 48 |
| 19p | 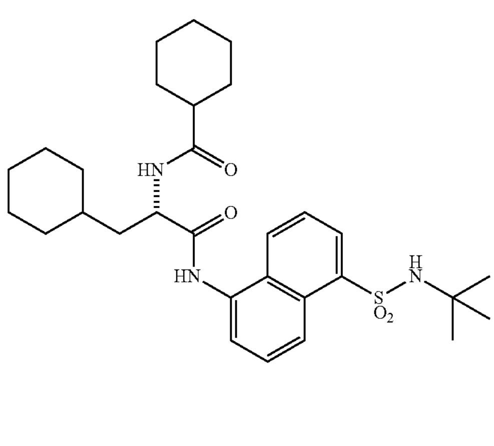 [SMILES: CC(C)(C)NS(=O)(=O)c1cccc2c(NC(=O)[C@H](CC3CCCCC3)NC(=O)C3CCCCC3)cccc12] | (S)-N-(1-((5-(N-(tert-butyl)sulfamoyl)naphthalen-1-yl)amino)-3-cyclohexyl-1-oxopropan-2-yl)cyclohexanecarboxamide | 195 |

TABLE 10-continued

USP30 IC$_{50}$ Values

| ID # | Structure | Name | IC$_{50}$ (nM) |
|---|---|---|---|
| 19q | 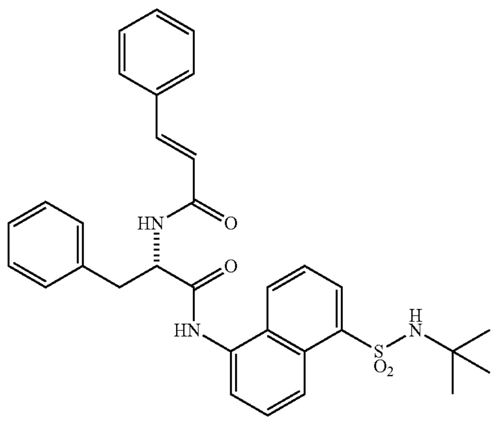 [SMILES: CC(C)(C)NS(=O)(=O)c1cccc2c(NC(=O)[C@H](Cc3ccccc3)NC(=O)/C=C/c3ccccc3)cccc12] | (S)-N-(1-((5-(N-(tert-butyl)sulfamoyl)naphthalen-1-yl)amino)-1-oxo-3-phenylpropan-2-yl)cinnamamide | >10,000 |
| 19s | 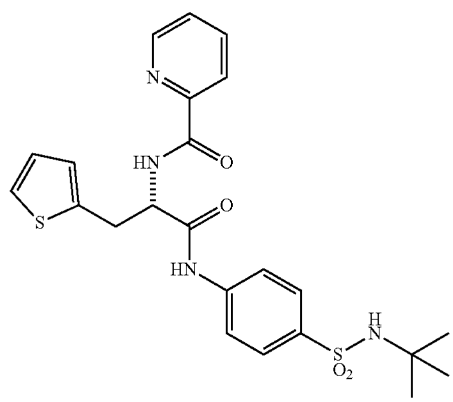 [SMILES: CC(C)(C)NS(=O)(=O)c1ccc(NC(=O)[C@H](Cc2cccs2)NC(=O)c2ccccn2)cc1] | (S)-N-(1-((4-(N-(tert-butyl)sulfamoyl)phenyl)amino)-1-oxo-3-(thiophen-2-yl)propan-2-yl)picolinamide | 200 |
| 19t | 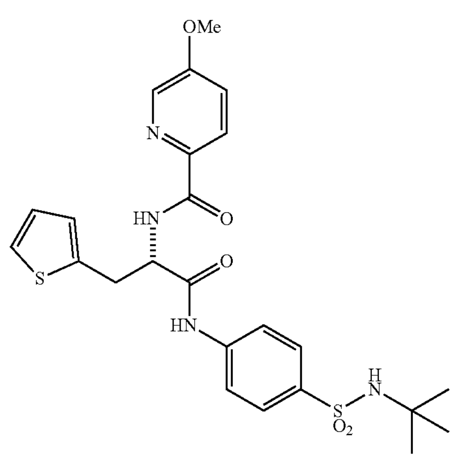 [SMILES: COc1ccc(C(=O)N[C@@H](Cc2cccs2)C(=O)Nc2ccc(S(=O)(=O)NC(C)(C)C)cc2)nc1] | (S)-N-(1-((4-(N-(tert-butyl)sulfamoyl)phenyl)amino)-1-oxo-3-(thiophen-2-yl)propan-2-yl)-5-methoxypicolinamide | 1,040 |

TABLE 10-continued

USP30 IC$_{50}$ Values

| ID # | Structure | Name | IC$_{50}$ (nM) |
|---|---|---|---|
| 19u | 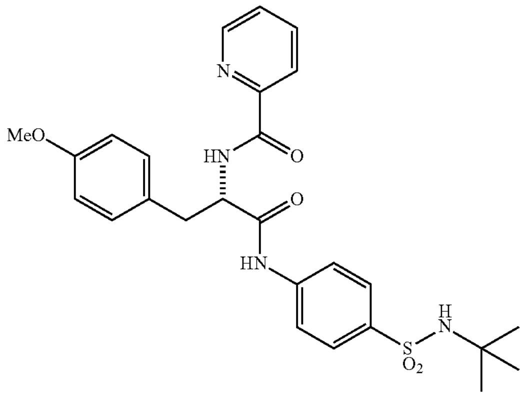 [SMILES: COc1ccc(C[C@H](NC(=O)c2ccccn2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)picolinamide | 195 |
| 19v | 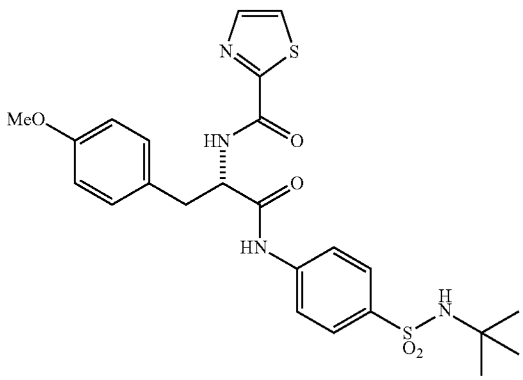 [SMILES: COc1ccc(C[C@H](NC(=O)c2nccs2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)thiazole-2-carboxamide | >10,000 |
| 19w | 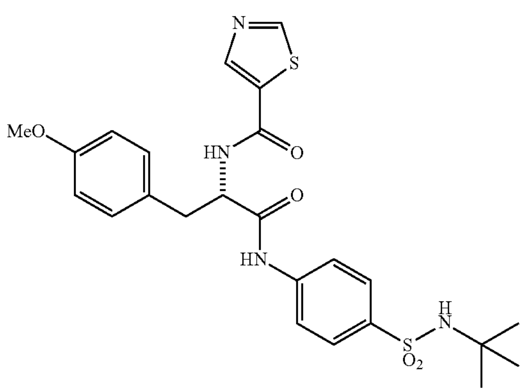 [SMILES: COc1ccc(C[C@H](NC(=O)c2cncs2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)thiazole-5-carboxamide | >10,000 |
| 19x | 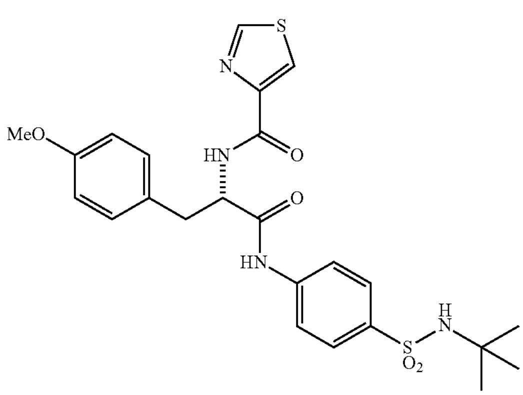 [SMILES: COc1ccc(C[C@H](NC(=O)c2cscn2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)thiazole-4-carboxamide | >10,000 |

TABLE 10-continued

USP30 IC$_{50}$ Values

| ID # | Structure | Name | IC$_{50}$ (nM) |
|---|---|---|---|
| 19y | 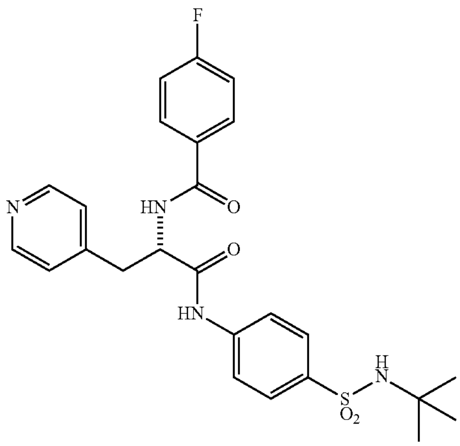 [SMILES: CC(C)(C)NS(=O)(=O)c1ccc(NC(=O)[C@H](Cc2ccncc2)NC(=O)c2ccc(F)cc2)cc1] | (S)-N-(1-((4-(N-(tert-butyl)sulfamoyl)phenyl)amino)-1-oxo-3-(pyridin-4-yl)propan-2-yl)-4-fluorobenzamide | 20 |
| 19z | 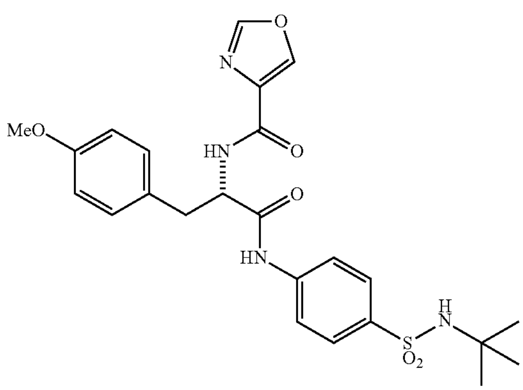 [SMILES: COc1ccc(C[C@H](NC(=O)c2cocn2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)oxazole-4-carboxamide | >10,000 |
| 19aa | 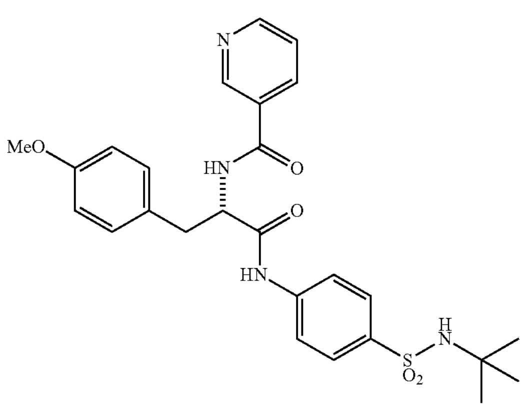 [SMILES: COc1ccc(C[C@H](NC(=O)c2cccnc2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)nicotinamide | 208 |

TABLE 10-continued

USP30 IC$_{50}$ Values

| ID # | Structure | Name | IC$_{50}$ (nM) |
|---|---|---|---|
| 19ab | 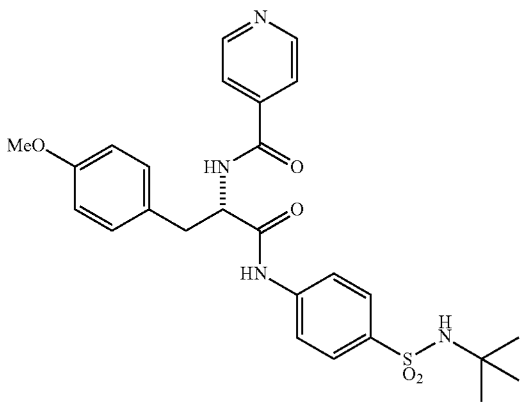 [SMILES: COc1ccc(C[C@H](NC(=O)c2ccncc2)C(=O)Nc2ccc(S(=O)(=O)NC(C)(C)C)cc2)cc1] | (S)-N-(1-((4-(N-(tert-butyl)sulfamoyl)phenyl)amino)-3-(4-methoxyphenyl)-1-oxopropan-2-yl)isonicotinamide | 2,400 |
| 19ac | 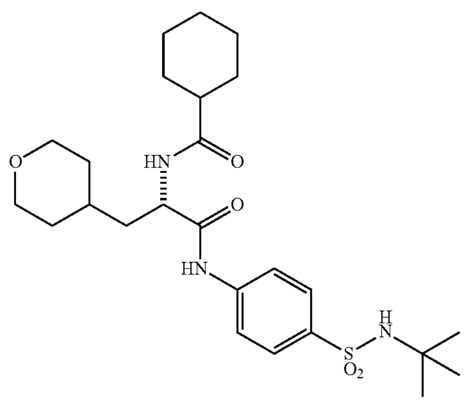 [SMILES: CC(C)(C)NS(=O)(=O)c1ccc(NC(=O)[C@H](CC2CCOCC2)NC(=O)C2CCCCC2)cc1] | (S)-N-(1-((4-(N-(tert-butyl)sulfamoyl)phenyl)amino)-1-oxo-3-(tetrahydro-2H-pyran-4-yl)propan-2-yl)cyclohexanecarboxamide | 71 |
| 19ad | 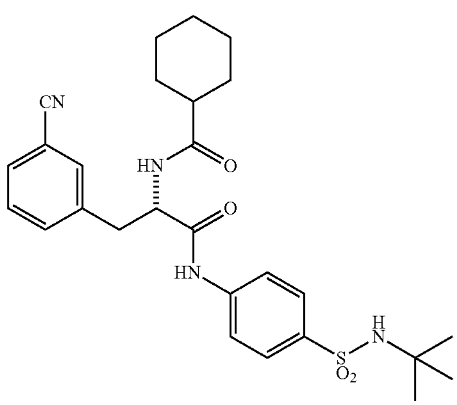 [SMILES: CC(C)(C)NS(=O)(=O)c1ccc(NC(=O)[C@H](Cc2cccc(C#N)c2)NC(=O)C2CCCCC2)cc1] | (S)-N-(1-((4-(N-(tert-butyl)sulfamoyl)phenyl)amino)-3-(3-cyanophenyl)-1-oxopropan-2-yl)cyclohexanecarboxamide | 41 |

TABLE 10-continued

USP30 IC50 Values

| ID # | Structure | Name | IC50 (nM) |
|---|---|---|---|
| 19ae | 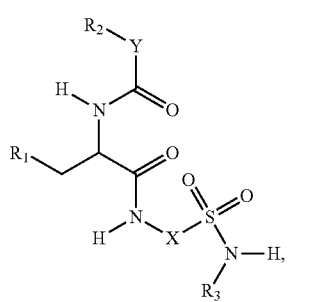 | (S)-N-(1-((4-(N-(tert-butyl)sulfamoyl)phenyl)amino)-1-oxo-3-(4-(trifluoromethoxy)phenyl)propan-2-yl)-4-fluorobenzamide | 3,600 |

What is claimed is:

1. A compound represented by structural formula (I):

(I)

or a pharmaceutically acceptable salt thereof, wherein:

X is phenyl or naphthyl;

Y is absent, a methylene group, an ethylene group, or an ethenylene group;

$R_1$ is $(C_1\text{-}C_4)$alkyl, 3-7 membered cycloalkyl, 5-6 membered heterocyclyl, 6-10 membered aryl, or 5-6 membered heteroaryl, each of which is independently optionally substituted with one or more substituents selected from the group consisting of halogen, CN, —$CO_2H$, hydroxyl, $(C_1\text{-}C_4)$alkyl, halo$(C_1\text{-}C_4)$alkyl, $(C_1\text{-}C_4)$alkoxy, halo$(C_1\text{-}C_4)$alkoxy, methylenedioxy, phenyl, —$NO_2$, —$OR^c$, $NR^aR^b$, —$S(O)_iR^a$, —$NR^aS(O)_iR^b$, —$S(O)_iNR^aR^b$, —$C(=O)OR^a$, —$OC(=O)OR^a$, —$C(=S)OR^a$, —$O(C=S)R^a$, —$C(=O)NR^aR^b$, —$NR^aC(=O)R^b$, —$C(=S)NR^aR^b$, —$NR^aC(=S)R^b$, —$NR^a(C=O)OR^b$, —$O(C=O)NR^aR^b$, —$NR^a(C=S)OR^b$, —$O(C=S)NR^aR^b$, —$NR^a(C=O)NR^aR^b$, —$NR^a(C=S)NR^aR^b$, —$C(=S)R^a$, and —$C(=O)R^a$;

$R_2$ is 3-7 membered cycloalkyl, 5-6 membered heterocyclyl, 6-10 membered aryl, 5-6 membered heteroaryl, or bridged 5-10 membered cycloalkyl; each of which is independently optionally substituted with one or more substituents selected from the group consisting of halogen, CN, —$CO_2H$, hydroxyl, $(C_1\text{-}C_4)$alkyl, halo$(C_1\text{-}C_4)$alkyl, $(C_1\text{-}C_4)$alkoxy, halo$(C_1\text{-}C_4)$alkoxy, $(C_1\text{-}C_4)$alkylthio, —$NO_2$, —$NR^aR^b$, —$S(O)_iR^a$, —$NR^aS(O)_iR^b$, —$S(O)_iNR^aR^b$, —$C(=O)OR^a$, —$OC(=O)OR^a$, —$C(=S)OR^a$, —$O(C=S)R^a$, —$C(=O)NR^aR^b$, —$NR^aC(=O)R^b$, —$C(=S)NR^aR^b$, —$NR^aC(=S)R^b$, —$NR^a(C=O)OR^b$, —$O(C=O)NR^aR^b$, —$NR^a(C=S)OR^b$, —$O(C=S)NR^aR^b$, —$NR^a(C=O)NR^aR^b$, —$NR^a(C=S)NR^aR^b$, —$C(=S)R^a$, and —$C(=O)R^a$;

$R_3$ is isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl;

each $R^a$ and each $R^b$ are independently selected from —H and $(C_1\text{-}C_5)$alkyl, optionally substituted with hydroxyl or $(C_1\text{-}C_3)$alkoxy;

$R^c$ is —H, $(C_1\text{-}C_5)$haloalkyl or $(C_1\text{-}C_5)$alkyl, wherein the $(C_1\text{-}C_5)$alkyl is optionally substituted with hydroxyl or $(C_1\text{-}C_3)$alkoxy; and i is 0,1 or 2.

2. The compound of claim 1, wherein the compound is represented by structural formula (Ia):

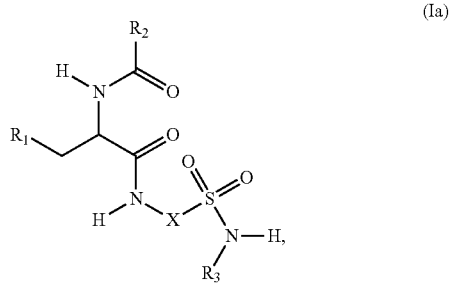

(Ia)

or a pharmaceutically acceptable salt thereof.

3. The compound of claim 2, wherein the compound is represented by structural formula (Ib):

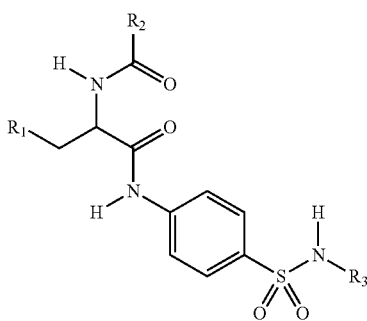

(Ib)

or a pharmaceutically acceptable salt thereof.

4. The compound of claim 2, wherein the compound is represented by structural formula (Ic):

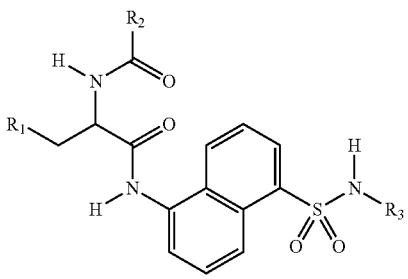

(Ic)

or a pharmaceutically acceptable salt thereof.

5. The compound of claim 2, or a pharmaceutically acceptable salt thereof, wherein $R_2$ is 3-7 membered cycloalkyl optionally substituted with one or more substituents selected from the group consisting of $(C_1-C_4)$alkyl, $(C_1-C_4)$alkoxy, $(C_1-C_4)$alkylthio, hydroxyl, halogen, and halo$(C_1-C_4)$alkyl; phenyl optionally substituted with one or more substituents selected from the group consisting of halogen, CN, —$CO_2H$, —$CO_2Me$, $(C_1-C_4)$alkyl, halo$(C_1-C_4)$alkyl, $(C_1-C_4)$alkoxy, and hydroxyl; 5-6 membered heterocyclyl optionally substituted with one or more substituents selected from the group consisting of $(C_1-C_4)$alkyl, halo$(C_1-C_4)$alkyl, and $(C_1-C_4)$alkoxy; 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy; or adamantyl.

6. The compound of claim 5, or a pharmaceutically acceptable salt thereof, wherein $R_1$ is $(C_1-C_4)$alkyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 3-7 membered cycloalkyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 5-6 membered heterocyclyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; phenyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, methylenedioxy, and phenyl; or 5-6 membered heteroaryl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio.

7. The compound of claim 2, or a pharmaceutically acceptable salt thereof, wherein $R_2$ is 3-7 membered cycloalkyl optionally substituted with one or more substituents selected from the group consisting of halogen and $(C_1-C_4)$alkyl; phenyl optionally substituted with one or more substituents selected from the group consisting of halogen, CN, —$CO_2H$, —$CO_2Me$, $(C_1-C_4)$alkyl, halo$(C_1-C_4)$alkyl, $(C_1-C_4)$alkoxy, and hydroxyl; 5-6 membered heterocyclyl selected from tetrahydrofuranyl or tetrahydro-2H-pyranyl; 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy, wherein the heteroaryl is pyridyl, pyridazinyl, pyrimidinyl, thiazolyl, oxazolyl, furanyl, pyrrolyl, or thiophenyl.

8. The compound of claim 7, or a pharmaceutically acceptable salt thereof, wherein $R_1$ is $(C_1-C_4)$alkyl; 3-7 membered cycloalkyl; tetrahydro-2H-pyranyl; phenyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and phenyl; 5-6 membered heteroaryl selected from pyridyl, imidazolyl, and thiophenyl.

9. The compound of claim 8, or a pharmaceutically acceptable salt thereof, wherein $R_3$ is t-butyl.

10. The compound of claim 2, or a pharmaceutically acceptable salt thereof, wherein $R_1$ is $(C_1-C_4)$alkyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; a 3-7 membered cycloalkyl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 5-6 membered heterocyclyl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; 6-10 membered aryl optionally substituted with one or more substituents selected from the group consisting of halogen, CN, hydroxyl, $(C_1-C_4)$alkyl, halo$(C_1-C_4)$alkyl, $(C_1-C_4)$alkoxy, halo$(C_1-C_4)$alkoxy, methylenedioxy, and phenyl; 5-6 membered heteroaryl optionally substituted with one or more substituents selected from the group consisting of halogen, —CN, hydroxyl, $(C_1-C_4)$alkyl, halo$(C_1-C_4)$alkyl, $(C_1-C_4)$alkoxy, halo$(C_1-C_4)$alkoxy, and $(C_1-C_4)$alkylthio; or a 5-10 membered bicycloalkyl selected from the group consisting of bicyclo[2.2.2]oct-1-yl, bicyclo[2.2.2]oct-2-yl, bicyclo[2.2.1]hept-1-yl, bicyclo[2.2.1]hept-2-yl; bicyclo[1.1.1]pentan-1-yl;

$R_2$ is a 3-7 membered cycloalkyl optionally substituted with one or more substituents selected from the group consisting of $(C_1-C_4)$alkyl, $(C_1-C_4)$alkoxy, $(C_1-C_4)$alkylthio, hydroxyl, halogen, and halo$(C_1-C_4)$alkyl; a 6-10 membered aryl optionally substituted with one or more substituents selected from the group consisting of halogen, CN, —$CO_2H$, —$CO_2Me$, $(C_1-C_4)$alkyl, halo$(C_1-C_4)$alkyl, $(C_1-C_4)$alkoxy, and hydroxyl; a 5-6 membered heterocyclyl optionally substituted with one or more substituents selected from the group consisting of $(C_1-C_4)$alkyl, halo$(C_1-C_4)$alkyl, $(C_1-C_4)$alkoxy; or a 5-6 membered heteroaryl optionally substituted with one or more substituents selected from the group consisting of halogen, $(C_1-C_4)$alkyl, halo$(C_1-C_4)$alkyl, and $(C_1-C_4)$alkoxy.

11. A pharmaceutical composition comprising a pharmaceutically acceptable carrier or diluent and the compound of claim 1.

12. A method of treating a ubiquitin specific peptidase 30 (USP30) mediated disorder in a subject comprising administering to the subject an effective amount of the compound of claim 1.

13. The method of claim 12, wherein the USP30 mediated disorder involves a mitochondrial defect is selected from the group consisting of a condition involving a mitophagy defect, a condition involving a mutation in mitochondrial DNA, a condition involving mitochondrial oxidative stress, a condition involving a defect in mitochondrial shape or morphology, a condition involving a defect in mitochondrial membrane potential, and a condition involving a lysosomal storage defect.

14. The method of claim 12, wherein the mitochondrial defect is selected from the group consisting of a neurodegenerative disease; mitochondrial myopathy, encephalopathy, lactic acidosis, and stroke-like episodes (MELAS) syndrome; Leber's hereditary optic neuropathy (LHON); neuropathy, ataxia, retinitis pigmentosa-maternally inherited Leigh syndrome (NARP-MILS); Danon disease; ischemic heart disease leading to myocardial infarction; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; coenzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrongenase deficiency (LCHAD); Leigh disease or syndrome; lethal infantile cardiomyopathy (LIC); Luft disease; glutaric aciduria type II; medium-chain acyl-CoA dehydrongenase deficiency (MCAD); myoclonic epilepsy and ragged-red fiber (MERRF) syndrome; mitochondrial recessive ataxia syndrome; mitochondrial cytopathy; mitochondrial DNA depletion syndrome; myoneurogastointestinal disorder and encephalopathy; Pearson syndrome; pyruvate carboxylase deficiency; pyruvate dehydrogenase deficiency; POLG mutations; medium/short-chain 3-hydroxyacyl-CoA dehydrogenase (M/SCHAD) deficiency; and very long-chain acyl-CoA dehydrongenase (VLCAD) deficiency.

15. The method of claim 14, wherein the neurodegenerative disease is selected from Alzheimer's disease, Parkinson's disease, amyotrophic lateral sclerosis (ALS), Huntington's disease, ischemia, stroke, dementia with Lewy bodies, and frontotemporal dementia.

16. The method of claim 15, wherein the neurodegenerative disease is Parkinson's disease, or amyotrophic lateral sclerosis (ALS).

17. The method of claim 12, wherein the USP30 mediated disorder is a neoplastic disease selected from metastatic carcinoma, multiple myeloma, osteosarcoma, chondosarcoma, Ewing's sarcoma, nasopharyngeal carcinoma, and leukemia.

18. A method of administering to the subject an effective amount of the compound of claim 1 to promote apoptosis in cells.

19. The method of claim 18, wherein the cells are cancer cells.

20. The method of claim 19, wherein the cancer cells are melanoma.

* * * * *

UNITED STATES PATENT AND TRADEMARK OFFICE
CERTIFICATE OF CORRECTION

PATENT NO. : 10,968,172 B2  
APPLICATION NO. : 16/606817  
DATED : April 6, 2021  
INVENTOR(S) : Art Kluge et al.

Page 1 of 1

It is certified that error appears in the above-identified patent and that said Letters Patent is hereby corrected as shown below:

In the Claims

At Column 116, Claim number 1, Line 25, replace "–$NO_2$, –$NR^aR^b$, –S(O),$R^a$", with -- –$NO_2$, –$OR^c$, –$NR^aR^b$, –S(O)$_i$$R^a$ --;

At Column 120, Claim number 14, Lines 3-4, replace "dehydrongenase", with -- dehydrogenase --;

At Column 120, Claim number 14, Line 6, replace "dehydrongenase", with -- dehydrogenase --; and At Column 120, Claim number 14, Line 15, replace "dehydrongenase", with -- dehydrogenase --.

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*